(12) United States Patent
Bethune et al.

(10) Patent No.: US 12,577,283 B2
(45) Date of Patent: Mar. 17, 2026

(54) KNOCKDOWN OR KNOCKOUT OF ONE OR MORE OF TAP2, NLRC5, B2m, TRAC, RFX5, RFXAP AND RFXANK TO MITIGATE T CELL RECOGNITION OF ALLOGENEIC CELL PRODUCTS

(71) Applicant: Allogene Therapeutics, Inc., South San Francisco, CA (US)

(72) Inventors: Michael Thomas Bethune, Castro Valley, CA (US); Eric Hans Gschweng, Oak Park, CA (US); Thomas John Van Blarcom, Oakland, CA (US); Cesar Adolfo Sommer, San Mateo, CA (US); Michael C Yi, Foster City, CA (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 333 days.

(21) Appl. No.: 17/649,305

(22) Filed: Jan. 28, 2022

(65) Prior Publication Data

US 2022/0251505 A1     Aug. 11, 2022

Related U.S. Application Data

(60) Provisional application No. 63/267,041, filed on Jan. 21, 2022, provisional application No. 63/176,818, filed on Apr. 19, 2021, provisional application No. 63/143,748, filed on Jan. 29, 2021.

(51) Int. Cl.
| | |
|---|---|
| *C07K 14/705* | (2006.01) |
| *A61K 38/00* | (2006.01) |
| *A61K 40/11* | (2025.01) |
| *A61K 40/31* | (2025.01) |
| *A61K 40/42* | (2025.01) |
| *A61K 40/50* | (2025.01) |
| *A61P 35/00* | (2006.01) |
| *C07K 14/725* | (2006.01) |
| *C07K 16/18* | (2006.01) |
| *C12N 5/0783* | (2010.01) |
| *C12N 15/90* | (2006.01) |

(52) U.S. Cl.
CPC ............ *C07K 14/705* (2013.01); *A61K 40/11* (2025.01); *A61K 40/31* (2025.01); *A61K 40/4202* (2025.01); *A61K 40/4211* (2025.01); *A61K 40/4272* (2025.01); *A61P 35/00* (2018.01); *C07K 14/7051* (2013.01); *C07K 16/18* (2013.01); *C12N 5/0636* (2013.01); *C12N 5/0638* (2013.01); *C12N 15/907* (2013.01); *A61K 38/00* (2013.01); *A61K 40/50* (2025.01); *A61K 2239/31* (2023.05); *A61K 2239/38* (2023.05); *A61K 2239/48* (2023.05);

*C07K 2319/30* (2013.01); *C07K 2319/33* (2013.01); *C12N 2510/00* (2013.01)

(58) Field of Classification Search
CPC ...................................................... C12N 5/0636
See application file for complete search history.

(56) References Cited

U.S. PATENT DOCUMENTS

| | | | |
|---|---|---|---|
| 5,037,743 A | 8/1991 | Welch et al. |
| 5,143,830 A | 9/1992 | Holland et al. |
| 5,858,358 A | 1/1999 | June et al. |
| 5,883,223 A | 3/1999 | Gray et al. |
| 6,011,138 A | 1/2000 | Reff et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Brenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |

(Continued)

FOREIGN PATENT DOCUMENTS

| | | |
|---|---|---|
| AU | 2020230334 A1 | 10/2020 |
| CN | 1568198 A | 1/2005 |

(Continued)

OTHER PUBLICATIONS

Ludigs et al. NLRC5 Exclusively Transactivates MHC Class I and Related Genes through a Distinctive SXY Module. PLoS Genetics 2015, 11;3:e1005088. (Year: 2015).*

(Continued)

*Primary Examiner* — Christopher M Babic
*Assistant Examiner* — Jennifer S Spence
(74) *Attorney, Agent, or Firm* — Allogene Therapeutics, Inc.

(57) ABSTRACT

Provided herein are engineered immune cells and populations thereof for administration to patients to treat cancer (e.g., solid tumors or liquid tumors) and other conditions. The cells are engineered to functionally express a reduced level of one or more of RFX5, NLRC5, TAP2, β2m, TRAC, RFXAP, CIITA and RFXANK. The cells optionally are further engineered to express one or more than one additional protein such as an antigen binding protein (e.g., a chimeric antigen receptor (CAR) or T cell receptor) to target tumor cells or other damaged cells in the patient and/or to express other genes at a reduced level. Also provided are methods of making and using the engineered cells, compositions and kits comprising them, and methods of treating by administering the cells and the compositions.

39 Claims, 28 Drawing Sheets
Specification includes a Sequence Listing.

(56)                  References Cited

U.S. PATENT DOCUMENTS

| | | | |
|---|---|---|---|
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 7,622,119 | B2 | 11/2009 | Sugiyama |
| 7,709,226 | B2 | 5/2010 | Foote |
| 9,169,328 | B2 | 10/2015 | Springgs et al. |
| 10,724,052 | B2 | 7/2020 | Rezania et al. |
| 10,808,035 | B2 | 10/2020 | Chmielewsk et al. |
| 10,815,301 | B2 | 10/2020 | Kochenderfer et al. |
| 11,077,144 | B2 | 8/2021 | Galetto et al. |
| 2006/0121005 | A1 | 6/2006 | Berenson et al. |
| 2016/0152725 | A1 | 6/2016 | Cheung |
| 2018/0002435 | A1 | 1/2018 | Sasu et al. |
| 2018/0148503 | A1 | 5/2018 | Scheinberg et al. |
| 2018/0325955 | A1* | 11/2018 | Terrett ........... A61K 39/464411 |
| 2020/0231699 | A1 | 7/2020 | Terrett et al. |
| 2020/0246383 | A1 | 8/2020 | Lebeau et al. |
| 2020/0347411 | A1 | 11/2020 | Razania et al. |
| 2021/0005859 | A1 | 1/2021 | Valamehr et al. |
| 2021/0062151 | A1 | 3/2021 | Valamehr et al. |
| 2021/0077530 | A1 | 3/2021 | Mamokin et al. |
| 2021/0115102 | A1 | 4/2021 | Winston et al. |
| 2021/0269501 | A1 | 9/2021 | Powell et al. |
| 2021/0277141 | A1 | 9/2021 | Zhao et al. |

FOREIGN PATENT DOCUMENTS

| | | | | |
|---|---|---|---|---|
| CN | 109628492 | A | 4/2019 | |
| CN | 109680002 | A | 4/2019 | |
| WO | 2002077029 | A2 | 10/2002 | |
| WO | 2016014565 | A2 | 1/2016 | |
| WO | 2016014576 | A1 | 1/2016 | |
| WO | 2016016341 | A1 | 2/2016 | |
| WO | 2016115559 | A1 | 7/2016 | |
| WO | 2016142532 | A1 | 9/2016 | |
| WO | 2016149368 | A1 | 9/2016 | |
| WO | 2016166630 | A1 | 10/2016 | |
| WO | 2017025038 | A1 | 2/2017 | |
| WO | 2017025323 | A1 | 2/2017 | |
| WO | 2017125830 | A1 | 7/2017 | |
| WO | 2017173410 | A1 | 10/2017 | |
| WO | 2018006882 | A1 | 1/2018 | |
| WO | 2018072025 | A1 | 4/2018 | |
| WO | 2018145649 | A1 | 8/2018 | |
| WO | 2018152181 | A1 | 8/2018 | |
| WO | 2018222935 | A1 | 12/2018 | |
| WO | 2019030240 | A1 | 2/2019 | |
| WO | 2020150339 | A1 | 4/2019 | |
| WO | 2019196713 | A1 | 10/2019 | |
| WO | 2019237035 | A1 | 12/2019 | |
| WO | 2020010235 | A1 | 1/2020 | |
| WO | 2020010284 | A1 | 1/2020 | |
| WO | 2020023888 | A2 | 1/2020 | |
| WO | 2020108646 | A1 | 6/2020 | |
| WO | 2020123691 | A2 | 6/2020 | |
| WO | WO-2020117526 | A1 * | 6/2020 | ............ A61K 35/17 |
| WO | 2020150534 | A2 | 7/2020 | |
| WO | 2020180591 | A1 | 9/2020 | |
| WO | 2020186204 | A1 | 9/2020 | |
| WO | 2020210398 | A1 | 10/2020 | |
| WO | 2021008463 | A1 | 1/2021 | |
| WO | 2021011919 | A1 | 1/2021 | |
| WO | 2019152742 | A1 | 8/2021 | |
| WO | 2021179353 | A1 | 9/2021 | |

OTHER PUBLICATIONS

Meissner et al. NLRC5 Cooperates with the RFX Transcription Factor Complex To Induce MHC Class I Gene Expression. Journal of Immunology 2012, 188;10:4951-4958. (Year: 2012).*

Pinello et al. Analyzing CRISPR genome-editing experiments with CRISPResso. Nature Biotechnology 2016, 34;7:695-687. (Year: 2016).*

Makabe, Koki, et al., "Thermodynamic Consequences of Mutations in Vernier Zone Residues of a Humanized Anti-human Epidermal Growth Factor Receptor Murine Antibody, 528", The Journal of Biological Chemistry vol. 283, No. 2, pp. 1156-1166, Jan. 11, 2008.

Mather, Jennie P., et al., "Introduction to Cell and Tissue Culture: Theory and Techique", Plem Press, New Yord, NY, 1998, (TOC).

Maude, S. L., et al., "Tisagenlecleucel in Children and Young Adults with B-Cell Lymphoblastic Leukemia", n engl j med 378;5 nejm.org Feb. 1, 2018.

Meissner, Torsten B., et al., "NLR family member NLRC5 is a transcriptional regulator of MHC class I genes", Proc Natl Acad Sci U S A; Aug. 3, 2010;107(31):13794-9. doi: 10.1073/pnas. 1008684107.

Miller, Jeffrey H., et al., "Gene Transfer Vectors for Mammalian Cells", Current Communications in Molecular Biology, Cold Spring Harbor Laboratory, 1987 (TOC).

Mo, Feiyan, et al., "Engineered off-the-shelf therapeutic T cells resist host immune rejection", Nat Biotechnol. Jan. 2021 ; 39(1): 56-63. doi:10.1038/s41587-020-0601-5.

Mullis, et al., "PCR: The Polymerase Chain Reaction", Birkauswer Press, Boston, 1994 (Table of Contents).

Myers, E. W., et al., "Optimal Alignments in Linear Space", 1988, CABIOS 4:11-17.

Park, Boyoun, et al., "Human cytomegalovirus inhibits tapasin-dependent peptide loading and optimization of the MHC class I peptide cargo for immune evasion", Immunity; Jan. 2004;20(1):71-85. doi: 10.1016/s1074-7613(03) 00355-8.

Remington, "The Science and Practice of Pharmacy", 21st Ed. Mack Publishing, 2005, Table of Contents.

Robinson, E. D., "Comparison of Labeled Trees with Valency Three", 1971, Comb. Theor. 11:105-119.

Rosenberg, Steven A., et al., "Adoptive cell transfer: a clinical path to effective cancer immunotherapy", Nat Rev Cancer. Apr. 2008 ; 8(4): 299-308. doi:10.1038/nrc2355.

Saitou, Naruya, et al., "The neighbor-joining method: a new method for reconstructing phylogenetic trees", Molecular Biology and Evolution, vol. 4, Issue 4, Jul. 1987, pp. 406-425, https://doi.org/10.1093/oxfordjournals.molbev.a040454.

Sambrook, J., et al., "Molecular Cloning: A Laboratory Manual", Second Ed., Cold Spring Harbor Laboratory Press, 1989 (TOC).

Shepherd, Philip, et al., "Monoclonal Antibodies: A Practical Approach", Oxford University Press, 2000 (TOC).

Shi, Yan, et al., "TAP-independent MHC class I peptide antigen presentation to alloreactive CTL is enhanced by target cell incubation at subphysiologic temperatures", J Immunol; May 1, 1998;160(9):4305-12.

Sneath, Peter H.A., et al., "Numerical Taxonomy—The Principles and Practice of Numerical Classification", Nature 193, 855-860 (1962) W. H. Freeman and Co. (TOC).

Sridharan, Kannan, et al., "Therapeutic nucleic acids: current clinical status", Br J Clin Pharmacol (2016) 82 659-672.

Steimle, V., et al., "Complementation cloning of an MHC class II transactivator mutated in hereditary MHC class II deficiency (or bare lymphocyte syndrome)", Cell; Oct. 8, 1993;75(1):135-46.

Tortorella, Domenico, et al., "Viral subversion of the immune system", Annual Review of Immunology; vol. 18:861-926 (Volume publication date Apr. 2000) https://doi.org/10.1146/annurev.immunol. 18.1.861.

Tramontano, Anna, et al., "Framework Residue 71 is a Major Determinant of the Position and Conformation of the Second Hypervariable Region in the V H Domains of Immunoglobulins", J. Mol. Biol. (1990) 215, 175-182.

UNIPROTKB, "P08560 (UL18_HCMVA)", accessed at https://www.uniprot.org/uniprot/P08560.

Vijayan, Saptha, et al., "Class I transactivator, NLRC5: a central player in the MHC class I pathway and cancer immune surveillance", Immunogenetics; . Mar. 2019;71(3):273-282. doi: 10.1007/s00251-019-01106-z.

Ward, E. Sally, et al., "Binding activities of a repertoire of single immunoglobulin variable domains secreted from *Escherichia coli*", Letter to Nature, Nature • vol. 341 • Oct. 12, 1989.

(56)　　　　　References Cited

OTHER PUBLICATIONS

Wei, Maria L., "HLA-A2 molecules in an antigen-processing mutant cell contain signal sequence-derived peptides", Nature; Apr. 2, 1992;356(6368):443-6. doi: 10.1038/356443a0.

Wilbur, W. J., et al., "Rapid Similarity Searches of Nucleic Acid and Protein Data Banks", 1983, Proc. Natl. Acad. Sci. USA vol. 80, pp. 726-730.

York, Ian , et al., "A cytosolic herpes simplex virus protein inhibits antigen presentation to CD8+ T lymphocytes", Cell; May 20, 1994;77(4):525-35. doi: 10.1016/0092-8674(94)90215-1.

Yoshihama, Sayuri , et al., "NLRC5/MHC class I transactivator is a target for immune evasion in cancer", Proc Natl Acad Sci U S A; May 24, 2016;113(21):5999-6004. doi: 10.1073/pnas.1602069113.

Zanetti, Maurizio , et al., "The Antibodies", vol. 1, Harwood Academic Publisher, 1995, Luxembourg (TOC).

Al-Lazikani, Bissan , et al., "Standard Conformations for the Canonical Structures of Immunoglobulins", J. Mol. Biol. (1997) 273, 927-948.

Atkins, J. F., et al., "A case for "StopGo": Reprogramming translation to augment codon meaning of GGN by promoting unconventional termination (Stop) after addition of glycine and then allowing continued translation (Go)", RNA (2007), 13:803-810., Cold Spring Harbor Laboratory Press.

Ausubel, Frederick M., et al., "Short Protocols in Molecular Biology", A Compendium of Methods from Current Protocols in Molecular Biology; 4th ED.; Wiley and Sons, 1999; (TOC).

Barel, Martine T, et al., "Human cytomegalovirus-encoded US2 differentially affects surface expression of MHC class I locus products and targets membrane-bound, but not soluble HLA-G1 for degradation", J Immunol Dec. 15, 2003, 171 (12) 6757-6765; DOI: https://doi.org/10.4049/jimmunol.171.12.6757.

Basu, Sreemanti , et al., "Purification of Specific Cell Population by Fluorescence Activated Cell Sorting (FACS)", Journal of Visualized Experiments, (41), e1546, doi:10.3791/1546 (2010).

Bierer, B. , et al., "Cyclosporin A and FK506: molecular mechanisms of immunosuppression and probes for transplantation biology", Current Opinion in Immunology; 1993; 5:763-773.

Bird, Robert E., et al., "Single Chain Antigen-Binding Proteins", Science, vol. 242, Issue 4877, Oct. 21, 1988; DOI: 10.1126/science.3140379.

Brenner, Malcom K., et al., "Adoptive T Cell Therapy of Cancer", Curr Opin Immunol. Apr. 2010 ; 22(2): 251-257. doi:10.1016/j.coi.2010.01.020.

Bubenik, Jan , "Tumour MHC class I downregulation and immunotherapy (Review)", Oncology reports, 2003, vol. 10 6), Aug. 2005.

Catty, D. , "Antibodies: a practical approach", IRL Press Ltd. 1988, Oxford England (TOC).

Celis, Julio E., "Cell Biology: A Laboratory Hnadbook", Academic Press, 1998 (TOC).

Chang, Cheong-Hee , et al., "Class II transactivator (CIITA) is sufficient for the inducible expression of major histocompatibility complex class II genes", J Exp Med; Oct. 1, 1994;180(4):1367-74. doi: 10.1084/jem.180.4.1367.

Chothia, Cyrus , et al., "Canonical structures for the hypervariable regions of immunoglobulins", J Mol Biol; Aug. 20, 1987;196(4):901-17. doi: 10.1016/0022-2836(87)90412-8.

Chothia, Cyrus , et al., "Conformations of immunoglobulin hypervariable regions", Nature. vol. 342 . 21/ Dec. 28, 1989.

Coligan, John E., et al., "Current Protocols in Immunology", vol. 1, 1991, John Wiley & Sons, Inc.(TOC).

Dayhoff, M. O., "A model of evolutionary change in proteins— Matrices for detecting distant relationships", Atlas of Protein sequence and structure, pp. 345-352, 1978.

De La Salle, Henri , et al., "Homozygous Human TAP Peptide Transporter Mutation in HLA Class I Deficiency", Science; Jul. 8, 1994;265(5169):237-41. doi: 10.1126/science.7517574.

Dembic, Zlatko , et al., "Transfer of specificity by murine alpha and beta T-cell receptor genes", Nature; vol. 320, 1986, pp. 232-238.

Deuse , "Hypoimmunogenic derivatives of induced pluripotent stem cells evade immune rejection in fully immunocompetent allogeneic recipients", Nat Biotechnol; Mar. 2019;37(3):252-258. doi: 10.1038/s41587-019-0016-3. Epub Feb. 18, 2019.

Donnelly, Michelle , et al., "Fluorescent Tagging of Herpes Simplex Virus Tegument Protein VP13/14 in Virus Infection", Journal of Virology, vol. 75, No. 6, Mar. 2001, p. 2575-2583.

Donnelly, Michelle , et al., "Nuclear Localization and Shuttling of Herpes Simplex Virus Tegument Protein VP13/14", Journal of Virology, vol. 75, No. 6, Mar. 2001, p. 2566-2574.

Doronina, Victoria A., et al., "Site-Specific Release of Nascent Chains from Ribosomes at a Sense Codon", Molecular and Cellular Biology, vol. 28, No. 13, Jul. 2008, p. 4227-4239.

Doyle, Alan , et al., "Cell and Tissue Culture: Laboratory Procedures in Biotechnology", John Wiley & Sons, Ltd., West Sussex, England, 1998 (TOC).

Eshhar, Zelig , et al., "Specific activation and targeting of cytotoxic lymphocytes through chimeric single chains consisting of antibody-binding domains and the gamma or zeta subunits of the immunoglobulin and T-cell receptors.", Immunology; Proc Natl Acad Sci U S A. Jan. 15, 1993; 90(2): 720-724.

Fellouse, F. A., "High-throughput Generation of Synthetic Antibodies from Highly Functional Minimalist Phage-displayed Libraries", J. Mol. Biol.; 2007; 373; 924-940.

Finch, Peter , "Antibodies", 1st Ed., Stride Publications, 1997 (TOC).

Fruh, Klaus , "A viral inhibitor of peptide transporters for antigen presentation", Nature; Jun. 1, 1995;375 (6530):415-8. doi: 10.1038/375415a0.

Gait, M. J., "Oligonucleotide Synthesis: A Practical Approach", IRL Press Ltd., Oxford, England, 1984 (TOC).

Gaj, Thomas , et al., "Genome-Editing Technologies: Principles and Applications", Cold Spring Harbor Perspective in Biology; 2016;8:a023754.

Gornalusse , "HLA-E-expressing pluripotent stem cells escape allogeneic responses and lysis by NK cells", Nat Biotechnol; Aug. 2017;35(8):765-772. doi: 10.1038/nbt.3860. Epub May 15, 2017.

Graham, Charlotte , et al., "Allogeneic CAR-T Cells: More than Ease of Access?", Cells 2018, 7, 155; doi:10.3390/cells7100155.

Harlow, Ed , et al., "Epitope Mapping", Using Antibodies: A Laboratory Manual, Chapter 11, Cold Spring Harbor Laboratory Press, NY, 1998.

Hein, J. , et al., "Unified Approach to Alignment and Phylogenies", Methods in Enzymology, vol. 183, 1990.

Henderson, D. J., et al., "Comparison of the effects of FK-506, cyclosporin A and rapamycin on IL-2 production", Immunology. Jul. 1991; 73(3):316-21.

Henderson, Robert A., et al., "HLA-A2.1-Associated Peptides from a Mutant Cell Line: A Second Pathway of Antigen Presentation", Science; Mar. 6, 1992;255(5049):1264-6. doi: 10.1126/science.1546329.

Higgins, Desmond G., et al., "Fast and sensitive multiple sequence alignments on a microcomputer", 1989, CABIOS 5:151-153.

Hill, Ann , et al., "Herpes simplex virus turns off the TAP to evade host immunity", Nature; Jun. 1, 1995;375 (6530):411-5. doi: 10.1038/375411a0.

Honegger, Annemarie , et al., "Yet Another Numbering Scheme for Immunoglobulin Variable Domains: An Automatic Modeling and Analysis Tool", J. Mol. Biol. (2001) 309, pp. 657-670; doi:10.1006/jmbi.2001.4662.

Ishido, Satoshi , et al., "Downregulation of Major Histocompatibility Complex Class I Molecules by Kaposi's Sarcoma-Associated Herpesvirus K3 and K5 Proteins", Journal of Virology; Jun. 2000;74(11):5300-9. doi: 10.1128/ivi.74.11.5300-5309.2000.

Janeway, Charles A., et al., "Immunobiology", Churchill Livingstone; 2nd Edition, Sep. 1, 1997, (TOC).

Jayasena, S. D., et al., "Aptamers: an emerging class of molecules that rival antibodies in diagnostics", Clin Chem. Sep. 1999;45(9):1628-50.

Jonjic, Stipan , et al., "Immune evasion of natural killer cells by viruses", Curr Opin Immunol. Feb. 2008 ; 20 (1): 30-38. doi:10.1016/j.coi.2007.11.002.

(56)　　　　　　　References Cited

OTHER PUBLICATIONS

Kabat, Elvin A., et al., "Sequences of Proteins of Immunological Interest", 5th Ed. NIH publication, No. 91-3242; 1992 (TOC).

Karre, Klas , et al., "Selective rejection of H-2-deficient lymphoma variants suggests alternative immune defence strategy", Nature vol. 319, 1986; pp. 675-678.

Lam, Jenny KW, et al., "siRNA Versus miRNA as Therapeutics for Gene Silencing", Molecular Therapy-Nucleic Acids (2015) 4, e252; doi:10.1038/mtna.2015.23.

Lehner, Paul J., et al., "The human cytomegalovirus US6 glycoprotein inhibits transporter associated with antigen processing-dependent peptide translocation", PANAS; 94 (13) 6904-6909; https://doi.org/10.1073/pnas.94.13.690.

Liu, J. , et al., "Inhibition of T Cell Signaling by Immunophilin-Ligand Complexes Correlates with Loss of Calcineurin Phosphatase Activity", Biochemistry, 1992, 31, 3891-3901.

Llano, Manuel , "Differential effects of US2, US6 and US11 human cytomegalovirus proteins on HLA class Ia and HLA-E expression: impact on target susceptibility to NK cell subsets", Eur J Immunol . Oct. 2003;33(10):2744-54. doi: 10.1002/eji.200324182.

Luft, Christin , et al., "Electroporation Knows No. Boundaries: The Use of Electrostimulation for siRNA Delivery in Cells and Tissues", Journal of Biomolecular Screening; 2015, vol. 20(8) 932-942; DOI: 10.1177/1087057115579638.

Lupfer, Christopher , et al., "NLRC5 regulates MHC-I expression and immunity during viral infection", J Immunol May 1, 2015, 194 (1 Supplement) 113.2.

Burr et al. An Evolutionarily Conserved Function of Polycomb Silences the MHC Class I Antigen Presentation Pathway and Enables Immune Evasion in Cancer. Cancer Cell. Oct. 14, 2019;36(4):385-401.e8. doi: 10.1016/j.ccell.2019.08.008. Epub Sep. 26, 2019.

Hanna et al. MHC class I and II deficiencies. J Allergy Clin Immunol. Aug. 2014;134(2):269-75. doi: 10.1016/j.jaci.2014.06.001. Epub Jul. 4, 2014.

Yoshihama et al. NLRC5/CITA expression correlates with efficient response to checkpoint blockade immunotherapy. Sci Rep. Feb. 5, 2021;11(1):3258. doi: 10.1038/s41598-021-82729-9.

\* cited by examiner

HLA-A2+ donor

HLA-A2- donor

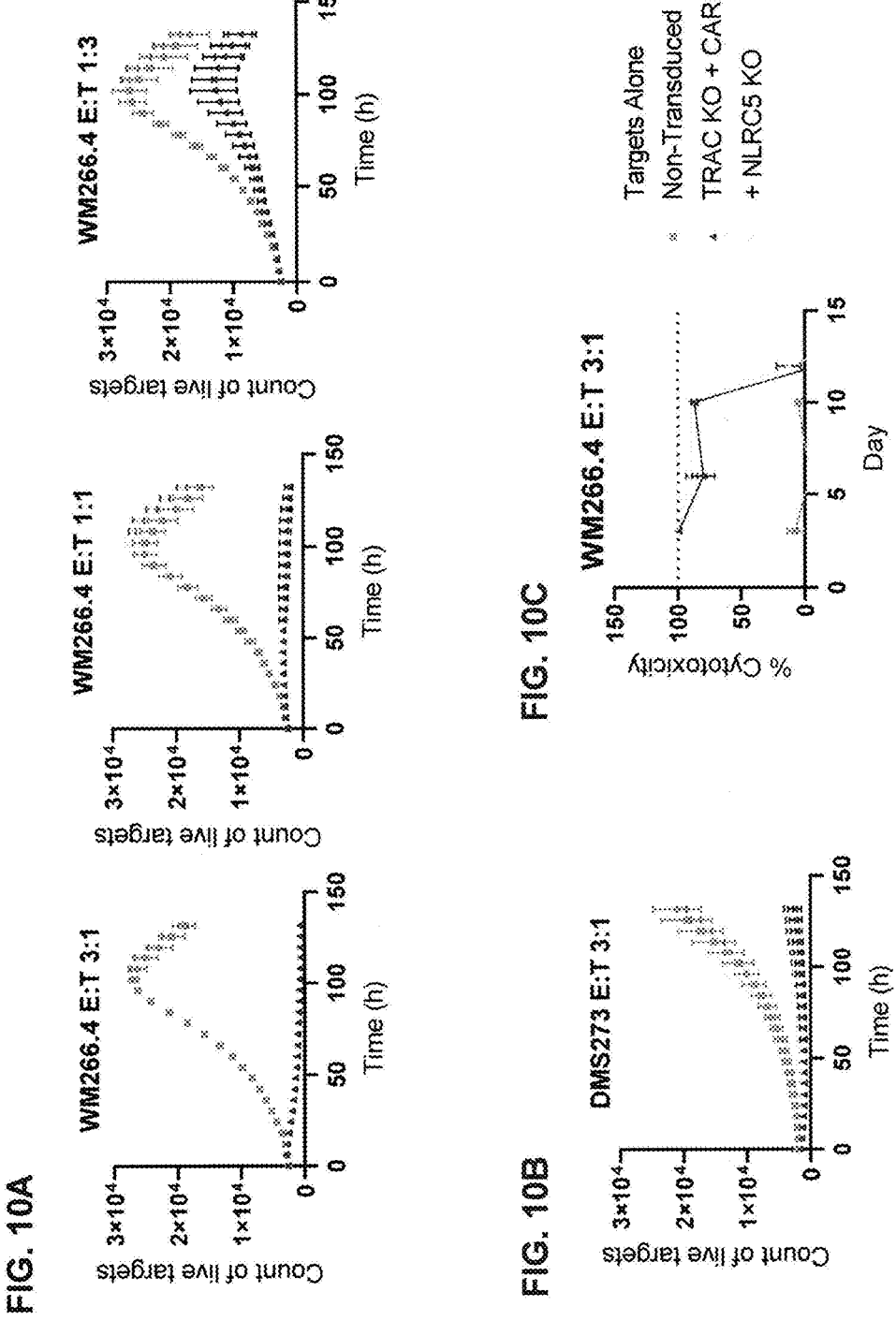

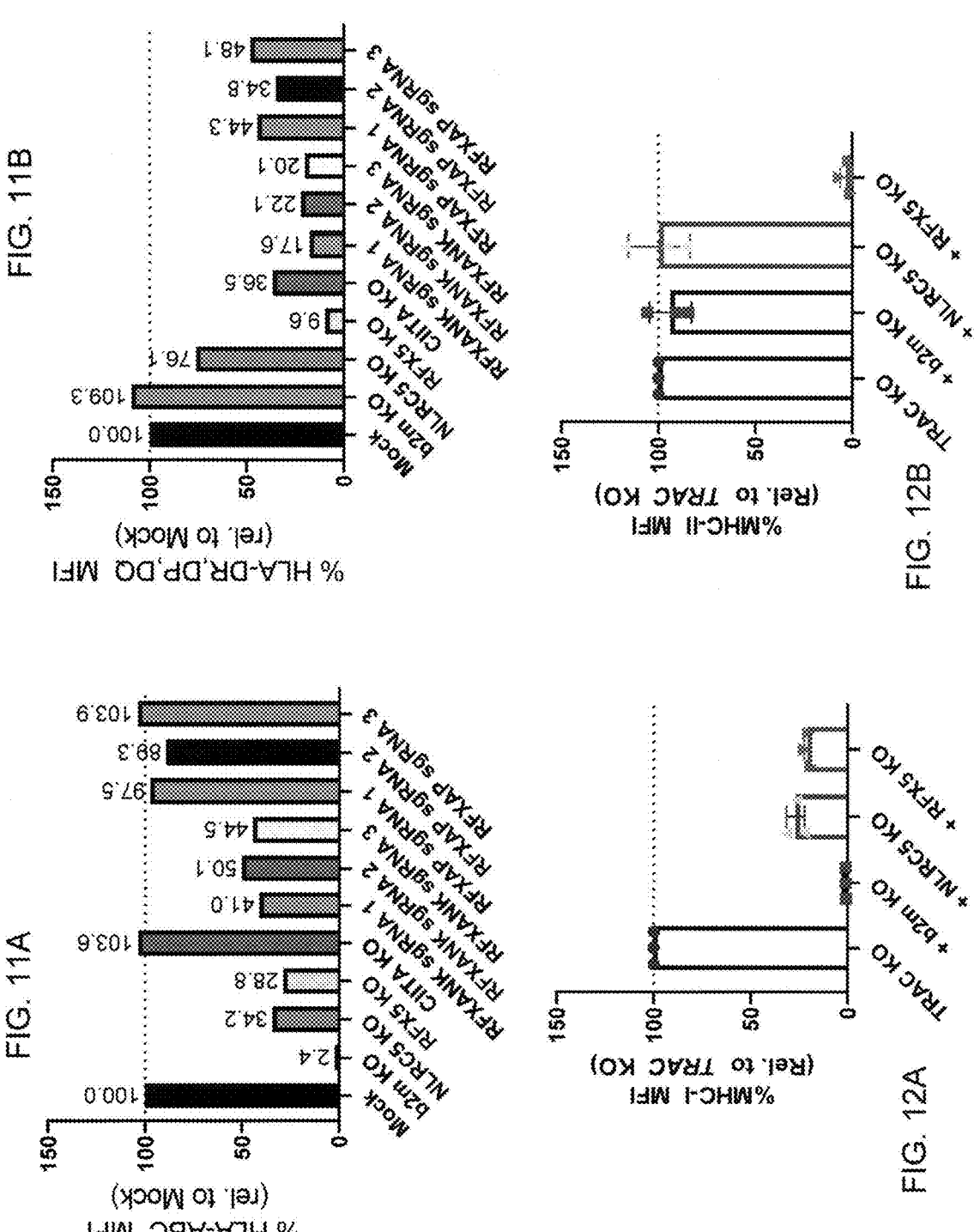

SEQUENCE LISTING

<160> NUMBER OF SEQ ID NOS: 22

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 1
gcugguacac ggcaggguca                            20

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 2
ucacgucauc cagcagagaa                            20

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 3
cagcucugca aggcucuggg                            20

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 4
aguacaugua ugccuaagg                            19

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 5
guggcacacu gugagcugcc                            20

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 6
uuguugacga gguugucacc                            20

```
<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcucgucugg cuuguugacg                                                   20

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gucaacaagc cagacgagcg                                                   20

<210> SEQ ID NO 9
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ucuuagcagc auggaggcgc                                                   20

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cuuagcagca uggaggcgca                                                   20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cauggaggcg cagggguguag                                                  20

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cgcguccacc agcagcaggg                                                   20
```

-continued

```
<210> SEQ ID NO 13
<211> LENGTH: 528
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
tagtccaatt tgttaaagac aggatatcag tggtccaggc tctagttttg actcaacaat      60
atcaccagct gaagcctata gagtacgagc catagataaa ataaaagatt ttatttagtc     120
tccagaaaaa gggggggaatg aaagacccca cctgtaggtt tggcaagcta ggatcaaggt    180
caggaacaga gaaacaggag aatatgggcc aaacaggata tctgtggtaa gcagttcctg     240
ccccgctcag ggccaagaac agttggaaca ggagaatatg ggccaaacag gatatctgtg     300
gtaagcagtt cctgccccgc tcagggccaa gaacagatgg tccccagatg cggtcccgcc     360
ctcagcagtt tctagagaac catcagatgt ttccagggtg ccccaaggac ctgaaatgac     420
cctgtgcctt atttgaacta accaatcagt tcgcttctcg cttctgttcg cgcgcttctg     480
ctccccgagc tcaataaaag agcccacaac ccctcactcg gcgcgatc                  528

<210> SEQ ID NO 14
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgagcgagc tgattaagga gaacatgcac atgaagctgt acatggaggg caccgtggac      60
aaccatcact tcaagtgcac atccgagggc gaaggcaagc cctacgaggg cacccagacc     120
atgagaatca aggtggtcga gggcggccct ctccccttcg ccttcgacat cctggctact     180
agcttcctct acggcagcaa gaccttcatc aaccacaccc agggcatccc cgacttcttc     240
aagcagtcct ccctgaggg cttcacatgg gagagagtca ccacatacga agacgggggc      300
gtgctgaccg ctacccagga caccagcctc caggacggct gcctcatcta caacgtcaag     360
atcagagggg tgaacttcac atccaacggc cctgtgatgc agaagaaaac actcggctgg     420
gaggccttca ccgagacgct gtaccccgct gacggcggcc tggaaggcag aaacgacatg     480
gccctgaagc tcgtgggcgg gagccatctg atcgcaaaca tcaagaccac atatagatcc     540
aagaaacccg ctaagaacct caagatgcct ggcgtctact atgtggacta cagactggaa     600
agaatcaagg aggccaacaa cgagacctac gtcgagcagc acgaggtggc agtggccaga     660
tactgcgacc tccctagcaa actggggcac aagcttaat                            699

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcaacgaatt tcagcctgct gaagcaggcc ggggacgtcg aggagaatcc agggcca        57

<210> SEQ ID NO 16
```

-continued

```
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgaacctgg tcatgctgat cctggccctg tgggcccccg tggcaggcag catgcctgag      60
ctgtccctga ccctgttcga cgagcccct ccactggtgg agacagagcc actgccacct     120
ctgtccgacg tgagcgagta cagagtggag tattctgagg caagatgcgt gctgagaagc     180
ggcggcaggc tggaggccct gtggaccctg cgcggcaatc tgagcgtgcc aaccccaca      240 cctcgggtgt actatcagac cctggaggga tacgcagaca gggtgccaac acccgtggag     300
gacgtgagcg agagcctggt ggccaagaga tactggctga gggactatcg cgtgccacag     360
aggaccaagc tggtgctgtt ctattttcc ccctgccacc agtgtcagac atactatgtg      420
gagtgcgagc tcgctgtct ggtgccttgg gtgccactgt ggagctccct ggaggacatc      480
gagcggctgc tgttcgagga tcggagactg atggcctact atgccctgac catcaagtcc     540
gcccagtaca cactgatgat ggtggccgtg atccaggtgt tttggggcct gtatgtgaag     600
ggctggctgc accggcactt cccatggatg ttttctgatc agtgg                     645

<210> SEQ ID NO 17
<211> LENGTH: 592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
aatcaacctc tggattacaa aatttgtgaa agattgactg gtattcttaa ctatgttgct      60 cctttacgc tatgtggata cgctgcttta atgcctttgt atcatgctat tgcttcccgt      120
atggctttca ttttctcctc cttgtataaa tcctggttgc tgtctcttta tgaggagttg     180
tggcccgttg tcaggcaacg tggcgtggtg tgcactgtgt tgctgacgc aaccccccact     240 ggttggggca ttgccaccac ctgtcagctc ctttccggga ctttcgcttt ccccctccct     300
attgccacgg cggaactcat cgccgcctgc cttgcccgct gctggacagg gctcggctg      360 ttgggcactg acaattccgt ggtgttgtcg gggaagctga cgtcctttcc atggctgctc     420
gcctgtgttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgcc tg             592

<210> SEQ ID NO 18
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30
```

-continued

```
Val Gln Pro Gly Gly Ser Leu Arg Leu Ser Cys Ala Ala Ser Gly Phe
        35              40              45

Thr Phe Ser Ser Tyr Ala Met Asn Trp Val Arg Gln Ala Pro Gly Lys
        50              55              60

Gly Leu Glu Trp Val Ser Thr Ile Ser Gly Ser Gly Gly Ser Thr Tyr
65              70              75              80

Tyr Ala Asp Ser Val Lys Gly Arg Phe Thr Ile Ser Arg Asp Asn Ser
                85              90              95

Lys Asn Thr Leu Tyr Leu Gln Met Asn Ser Leu Arg Ala Glu Asp Thr
            100             105             110

Ala Val Phe Tyr Cys Ala Ile Asp Pro Glu Tyr Tyr Asp Ile Leu Thr
            115             120             125

Gly Gly Asp Tyr Trp Gly Gln Gly Thr Leu Val Thr Val Ser Ser Gly
    130             135             140

Gly Gly Gly Ser Gly Gly Gly Gly Ser Gly Gly Gly Gly Ser Gly Gly
145             150             155             160

Gly Gly Ser Asp Ile Gln Met Thr Gln Ser Pro Ser Ala Met Ser Ala
                165             170             175

Ser Val Gly Asp Arg Val Thr Ile Thr Cys Arg Ala Ser Gln Gly Ile
            180             185             190

Ser Asn Tyr Leu Ala Trp Phe Gln Gln Lys Pro Gly Lys Val Pro Lys
            195             200             205

Arg Leu Ile Tyr Ala Ala Ser Ser Leu Gln Ser Gly Val Pro Ser Arg
    210             215             220

Phe Ser Gly Ser Gly Ser Gly Thr Glu Phe Thr Leu Thr Ile Ser Ser
225             230             235             240

Leu Gln Pro Glu Asp Phe Ala Thr Tyr Phe Cys Leu Gln His Asp Ser
                245             250             255

Phe Pro Leu Thr Phe Gly Gly Gly Thr Lys Val Glu Ile Lys Thr Thr
            260             265             270

Thr Pro Ala Pro Arg Pro Pro Thr Pro Ala Pro Thr Ile Ala Ser Gln
            275             280             285

Pro Leu Ser Leu Arg Pro Glu Ala Cys Arg Pro Ala Ala Gly Gly Ala
    290             295             300

Val His Thr Arg Gly Leu Asp Phe Ala Cys Asp Ile Tyr Ile Trp Ala
305             310             315             320

Pro Leu Ala Gly Thr Cys Gly Val Leu Leu Leu Ser Leu Val Ile Thr
            325             330             335

Leu Tyr Cys Lys Arg Gly Arg Lys Lys Leu Leu Tyr Ile Phe Lys Gln
            340             345             350

Pro Phe Met Arg Pro Val Gln Thr Thr Gln Glu Glu Asp Gly Cys Ser
            355             360             365

Cys Arg Phe Pro Glu Glu Glu Glu Gly Gly Cys Glu Leu Arg Val Lys
    370             375             380

Phe Ser Arg Ser Ala Asp Ala Pro Ala Tyr Gln Gln Gly Gln Asn Gln
385             390             395             400

Leu Tyr Asn Glu Leu Asn Leu Gly Arg Arg Glu Glu Tyr Asp Val Leu
                405             410             415

Asp Lys Arg Arg Gly Arg Asp Pro Glu Met Gly Gly Lys Pro Arg Arg
            420             425             430

Lys Asn Pro Gln Glu Gly Leu Tyr Asn Glu Leu Gln Lys Asp Lys Met
            435             440             445

Ala Glu Ala Tyr Ser Glu Ile Gly Met Lys Gly Glu Arg Arg Arg Gly
```

```
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                    485                 490

<210> SEQ ID NO 19
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Leu Pro Val Thr Ala Leu Leu Leu Pro Leu Ala Leu Leu Leu
1                   5                   10                  15

His Ala Ala Arg Pro Glu Val Lys Leu Gln Glu Ser Gly Pro Gly Leu
                20                  25                  30

Val Ala Pro Ser Gln Ser Leu Ser Val Thr Cys Thr Val Ser Gly Val
            35                  40                  45

Ser Leu Pro Asp Tyr Gly Val Ser Trp Ile Arg Gln Pro Pro Arg Lys
        50                  55                  60

Gly Leu Glu Trp Leu Gly Val Ile Trp Gly Ser Glu Thr Thr Tyr Tyr
65                  70                  75                  80

Asn Ser Ala Leu Lys Ser Arg Leu Thr Ile Ile Lys Asp Asn Ser Lys
                85                  90                  95

Ser Gln Val Phe Leu Lys Met Asn Ser Leu Gln Thr Asp Asp Thr Ala
            100                 105                 110

Ile Tyr Tyr Cys Ala Lys His Tyr Tyr Tyr Gly Gly Ser Tyr Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Thr Thr Ser Ser Leu Ser Ala Ser Leu Gly Asp Arg Val Thr
                165                 170                 175

Ile Ser Cys Arg Ala Ser Gln Asp Ile Ser Lys Tyr Leu Asn Trp Tyr
            180                 185                 190

Gln Gln Lys Pro Asp Gly Thr Val Lys Leu Leu Ile Tyr His Thr Ser
        195                 200                 205

Arg Leu His Ser Gly Val Pro Ser Arg Phe Ser Gly Ser Gly Ser Gly
    210                 215                 220

Thr Asp Tyr Ser Leu Thr Ile Ser Asn Leu Glu Gln Glu Asp Ile Ala
225                 230                 235                 240

Thr Tyr Phe Cys Gln Gln Gly Asn Thr Leu Pro Tyr Thr Phe Gly Gly
                245                 250                 255

Gly Thr Lys Leu Glu Ile Thr Thr Thr Thr Pro Ala Pro Arg Pro Pro
                260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320
```

-continued

```
Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

```
<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ugaguauacu ugaauuugag                                            20

<210> SEQ ID NO 21
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gccucacaag ccaggcccac                                            20

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Gly Ser Gly Gly Gly Gly Ser Gly Gly Gly Gly Ser
1               5                   10                  15
```

KNOCKDOWN OR KNOCKOUT OF ONE OR MORE OF TAP2, NLRC5, B2m, TRAC, RFX5, RFXAP AND RFXANK TO MITIGATE T CELL RECOGNITION OF ALLOGENEIC CELL PRODUCTS

CROSS REFERENCE TO RELATED APPLICATIONS

The present application claims the benefit of priority to U.S. Provisional Application No. 63/143,748, filed Jan. 29, 2021; U.S. Provisional Application No. 63/176,818, filed Apr. 19, 2021; and U.S. Provisional Application No. 63/267,041 filed Jan. 21, 2022, the contents of all of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 27, 2022, is named AT-041_04US_SL.txt and is 16,778 bytes in size.

FIELD

The present disclosure relates generally to the use of engineered immune cells (e.g., T cells) for use in therapeutic applications.

BACKGROUND

Adoptive transfer of immune cells genetically modified to recognize malignancy-associated antigens is showing promise as a new approach to treating cancer (see, e.g., Brenner et al., Current Opinion in Immunology, 22(2): 251-257 (2010); Rosenberg et al., Nature Reviews Cancer, 8(4): 299-308 (2008)). Immune cells can be genetically modified to express chimeric antigen receptors (CARs), fusion proteins comprised of an antigen recognition moiety and T cell activation domains (see, e.g., Eshhar et al., Proc. Natl. Acad. Sci. USA, 90(2): 720-724 (1993)). Immune cells that contain CARs, e.g., CAR-T cells (CAR-Ts), are engineered to endow them with antigen specificity while retaining or enhancing their ability to recognize and kill a target cell.

However, the generation of CAR-modified autologous cell therapies is expensive, requires weeks of process and quality testing, and yields product of variable potency depending on the initial quality and quantity of patient-specific T cells employed. Allogeneic CAR-modified cell therapies—in which cells from a healthy donor are modified with CAR and then administered to multiple patients—promises a cheaper and more robust product than autologous therapies that can be delivered immediately upon need (see, e.g., Graham et al., Cells 2018, 7, 155; doi:10.3390/cells7100155). Additionally, allogeneic therapies enable selection on desirable product characteristics (e.g. gene editing efficiency, site of integration, lack of deleterious off-target gene edits, haplotype, etc.), and facilitate more sophisticated cell engineering (e.g. multiple gene edits improving potency, persistence, homing, etc.). A major hurdle to implementing allogeneic CAR-modified cell therapies is the potential for rejection of the product (donor) by the immune system of the patient (host).

Killer lymphocytes such as CD8+ T cells and natural killer (NK) cells identify and kill cancerous, virally infected, and foreign cells (including allogeneic cells) that deviate from self. The central determinants of self vs non-self-discrimination are the major histocompatibility complex (MHC) molecules expressed on the surface of all nucleated cells. Each MHC class I molecule is a non-covalent trimeric complex of a highly multi-allelic MHC class I heavy chain (the most common of which is HLA-A2), an invariant β2 microglobulin (β2m), and a presented peptide proteolytically-derived from an internally expressed protein. Collectively, MHC class I molecules are loaded with peptides representative of the entire protein diversity expressed within the cell, enabling cancerous and infected cells to 'announce' their distress to the immune system. CD8+ T cells recognize these non-self peptides with a T cell receptor (TCR) unique to each nascent T cell and initiate killing pursuant to recognition of non-self peptide-MHC (see, e.g., Dembić, Z. et al. Nature 320, 232-238 (1986)). The recognition of non-self by T cells is complemented by the recognition of 'missing self' by NK cells: inhibitory receptors on the surface of NK cells enable NK cell-mediated killing in the absence of MHC (see, e.g., K. Kärre et al., Nature 319, 675-678 (1986).) (see FIGS. 1 and 3). Experimental ablation of MHC class I presentation—achieved through CRISPR/Cas9-mediated genomic knockout (KO) of the b2m gene encoding the universal β2m component of MHC class I—results in potent NK activation and selective killing of T cells lacking MHC in both autologous and alloreactive contexts (see FIG. 2).

While allogeneic cell therapies present a number of advantages over autologous cell therapies, allogeneic cells also face rejection by host or recipient immune system cells reactive with T and NK epitope determinants on the surface of the allogeneic cell product that are distinct from host. The present disclosure provides the advantages of improved allogeneic therapies that provide increased persistence of the administered cells despite the recipients' natural defenses.

SUMMARY

Provided herein are immune cells that have been engineered e.g. genetically engineered to mitigate rejection by a host or recipient into which or whom the cells have been introduced, methods of mitigating rejection and/or recognition by a host or recipient's immune system e.g. T cells and/or NK cells, compositions and populations comprising the engineered cells and methods of treating a cancer in a patient using the same. The immune cells of the instant disclosure are engineered to functionally express a reduced level, relative to corresponding cells that have not been so engineered, of one or both of NLRC5 and TAP2, two genes whose products participate in antigen presentation by cells, or of any one or more of TAP2, NLRC5, β2m, TRAC, CIITA, RFX5, RFXAP and RFXANK. The engineered cells can be further engineered to augment resistance to rejection and/or to provide a therapeutic effect, e.g. the cells can be engineered to comprise or express an additional protein, e.g. an antigen binding protein such as a chimeric antigen receptor (CAR) and/or a T cell receptor, wherein the antigen binding protein or T cell receptor targets the engineered immune cell to tumor cells that express a cognate antigen and/or to other undesired e.g. disease state cells. The present disclosure thus provides a method of increasing persistence of allogeneic cells in a recipient, the method comprising engineering the cells to functionally express a reduced level of one or both of NLRC5 and TAP2, one or both of RFX5 and NLRC5, one or both of RFX5 and TAP2, or of any one or more of TAP2, NLRC5, β2m, TRAC, CIITA, RFX5, RFXAP and RFXANK, relative to non-engineered cells.

In an aspect, the present disclosure provides an engineered immune cell that functionally expresses any one or more of TAP2, NLRC5, β2m, TRAC, CIITA, RFX5, RFXAP and RFXANK at a reduced level. In some embodiments, the reduced level of expression, stated relative to the expression level in a corresponding but non-engineered immune cell, is 0%, for example when both chromosomal copies of a gene are knocked out, or 50% (i.e. 50% of the level in a non-engineered control immune cell), for example when one of the two chromosomal copies of a gene is knocked out and there is no compensatory increase in expression of the other chromosomal copy of that gene. In some embodiments, the cell expresses any one or more of TAP2, NLRC5, β2m, TRAC, CIITA, RFX5, RFXAP and RFXANK at a level not greater than 90%, not greater than 75%, not greater than 50%, not greater than 25%, or not greater than 10% of the expression level in a non-engineered immune cell. In some embodiments, the level of expression of any one or more of TAP2, NLRC5, β2m, TRAC, CIITA, RFX5, RFXAP and RFXANK in the engineered immune cell is any value between 0% and 90% of the level in a control cell not correspondingly engineered with respect to the corresponding gene. In some embodiments, the expression level in the engineered cell is, for example, between 10% and 90%, between 25% and 90%, between 25% and 75%, between 10% and 50%, between 25% and 50%, between 50% and 90%, or between 50% and 75% of the level in a control cell. In some embodiments, a reduced level of expression other than 0% or 50% is obtained when, for example, only one chromosomal copy of a gene is knocked out and a compensatory mechanism causes an increase in the level of expression of the remaining chromosomal copy, or reduction in expression is achieved by a method other than gene knockout, such as known knockdown methods e.g. those that employ any of various RNA-based techniques (e.g. antisense RNA, miRNA, siRNA; see, e.g., Lam et al., Mol. Ther.-Nucleic Acids 4:e252 (2015), doi:10.1038/mtna.2015.23; Sridharan and Gogtay, Brit. J. Clin. Pharmacol. 82: 659-72 (2016)) In some embodiments, the engineered immune cell disclosed herein exhibits a reduced level of expression of an MHC class I protein or complex at the cell surface relative to a suitable control. In various embodiments, the cell is a T cell e.g. a human T cell. In some embodiments, the cell comprises a mutation in any one or more of the TAP2, NLRC5, β2m, TRAC, CIITA, RFX5, RFXAP and RFXANK loci or genes and/or a disruption in any one or more of the TAP2, NLRC5, β2m, TRAC, CIITA, RFX5, RFXAP and RFXANK loci or genes that causes a reduction in functional expression of the disrupted locus or gene. In an embodiment, the mutation or disruption is introduced by any one or a combination of gene mutations or gene editing techniques, including but not limited to known homologous recombination techniques and techniques that employ any one or more of meganucleases, TALEN, zinc fingers, shRNA, Cas-CLOVER, and a CRISPR/Cas system (for example, Cas9, Cas12 and MAD7). In some embodiments, the cell is a non-human cell, e.g. a primate cell or a non-primate mammalian cell. In some embodiments, the cell is a human cell. In some embodiments, the mutation or disruption is produced by knocking in a nucleic acid e.g. a nucleic acid that encodes one or more proteins or gene products to be expressed in the cell. In some embodiments, the nucleic acid encodes either or both of membrane glycoprotein UL18 (see, e.g., UniProtKB—P08560 (UL18_HCMVA), accessed at https://www.uniprot.org/uniprot/P08560) and ADR. In various embodiments, the ADR (alloimmune defense receptor) comprises the same components or domains as the ADRs disclosed in Feiyan Mo et al., Nature Biotechnol. (2021) 39(1): 56-63. doi:10.1038/s41587-020-0601-5 ("Mo et al. 2021") and/or in U.S. Patent Publication No. 2021/0077530 (Mar. 18, 2021) ("the '530 Publication"), the contents of both of which are incorporated herein in their entirety. In some embodiments, the ADR is a 4-1BB ADR, OX40 ADR, or a CD40L ADR such as that disclosed in the '530 Publication.

In various embodiments, the engineered immune cell further expresses an antigen binding protein, for example, the engineered immune cell comprises a nucleic acid that encodes an antigen binding protein. In an embodiment, the antigen binding protein is a chimeric antigen receptor (CAR). In an embodiment, a nucleic acid encoding the antigen binding protein e.g. the CAR is inserted into a disrupted TAP2, NLRC5, β2m, TRAC, CIITA, RFX5, RFXAP or RFXANK locus or is inserted into the locus, thereby disrupting it. In various embodiments, the antigen binding protein is a T cell receptor (TCR). In an embodiment, a nucleic acid encoding the TCR is inserted into a disrupted TAP2, NLRC5, β2m, TRAC, CIITA, RFX5, RFXAP or RFXANK locus or is inserted into the locus, thereby disrupting it. In an embodiment, the engineered immune cell further comprises one or more genomic modifications, e.g. a modification of an endogenous genetic locus, for example, of one or more of the following: an endogenous CD70 gene, an endogenous TCRa gene and an endogenous CD52 gene. In various embodiments, the one or more genomic modifications cause a reduction or absence of functional expression of the gene that contains the modification.

The engineered immune cell can be derived from cells from any of various sources. The engineered immune cell can be prepared or derived from cells e.g. stem cells or immune cells from a person other than the person to whom the engineered immune cells will be administered, e.g. a donor (e.g. a healthy volunteer) other than the recipient, or can be prepared or derived from cells e.g. stem cells or immune cells from the person to whom the engineered immune cells will be administered (the recipient), or can be derived from one or more induced pluripotent stem cells (iPSCs). In an embodiment, the immune cell is an immune cell obtained from a healthy volunteer, is obtained from a patient, or is derived from an iPSC.

In another aspect, the present disclosure provides a method of making the engineered immune cell disclosed herein. In an embodiment, the method comprises the use of any gene editing technology, such as TALEN, zinc fingers, Cas-CLOVER, and a CRISPR/Cas system, and/or the use of any known gene knockdown methods e.g. those that employ any of various RNA-based techniques (e.g. shRNA, antisense RNA, miRNA, siRNA; see, e.g., Lam et al., Mol. Ther.-Nucleic Acids 4:e252 (2015), doi:10.1038/mtna.2015.23; Sridharan and Gogtay, Brit. J. Clin. Pharmacol. 82: 659-72 (2016)) to reduce functional expression of one or more of TAP2, NLRC5, β2m, TRAC, CIITA, RFX5, RFXAP and RFXANK. In an embodiment, the method comprises or further comprises the introduction into the engineered immune cell of a nucleic acid encoding an antigen binding protein, e.g. a CAR or TCR. In an embodiment, the method comprises or further comprises introducing into the genome of the engineered immune cell one or more genomic modifications of one or more of an endogenous TCRa gene and an endogenous CD52 gene. In an embodiment, the one or more genomic modifications disrupts and/or prevents, wholly or partly, the functional expression of one or more of an endogenous TCRa gene and an endogenous CD52 gene.

In various embodiments of the present disclosure, the functional expression level of any one or more of TAP2, NLRC5, β2m, TRAC, CIITA, RFX5, RFXAP and RFXANK is measured by determining the surface expression level of one or more HLA proteins, such as an HLA-A or HLA-B protein, or of beta2 microglobulin (B2M), or of both one or more HLA proteins and B2M on the surface of the engineered immune cell, or is measured by flow cytometry. In some embodiments, expression of any one or more of TAP2, NLRC5, β2m, TRAC, CIITA, RFX5, RFXAP and RFXANK in engineered immune cells of the present disclosure is assayed by measuring the degree to which the engineered immune cells survive in the presence of effector cells e.g. T cells, in comparison to the degree to which not correspondingly engineered, but otherwise comparable e.g. identical, immune cells survive under the same conditions.

In some embodiments, an immune cell that has been engineered to functionally express a reduced level, relative to corresponding cells that have not been so engineered, of one or both of NLRC5 and TAP2, is further engineered to express one or more proteins selected from the group consisting of HLA-E, HLA-E single-chain trimer, HLA-G, HLA-G single-chain trimer, UL18, UL18 single-chain trimer, HLA-A2, HLA-A2 single-chain trimer, human cytomegalovirus (HCMV) US11 and/or to express a reduced level of any one or more of β2m, TRAC, CIITA, RFXANK, RFXAP and RFX5 achieved by knockout or knockdown as described herein.

In another aspect, the present disclosure provides a population of engineered immune cells comprising an engineered immune cell provided herein. In an embodiment, the population of engineered immune cells comprises between $10^4$ and $10^{10}$ engineered immune cells provided herein. In various embodiments, the population of engineered immune cells comprises $10^4$, $10^5$, $10^6$, $10^7$, $10^8$, $10^9$, or $10^{10}$ engineered immune cells provided herein.

In another aspect, the present disclosure provides a population of engineered immune cells wherein no more than, for example, 75% of the cells functionally express one or more of TAP2, NLRC5, β2m, TRAC, CIITA, RFX5, RFXAP and RFXANK. In an embodiment, no more than 75% of the cells of the population functionally express TAP2. In an embodiment, no more than 75% of the cells of the population functionally express NLRC5. In an embodiment, no more than 75% of the cells of the population functionally express RFX5.

In another aspect, the present disclosure provides a population of engineered immune cells wherein at least 1%, 5%, 10%, 20%, 30%, 40%, 50%, 75%, 90%, 95% or 100% of the engineered immune cells functionally express any one or more of TAP2, NLRC5, β2m, TRAC, CIITA, RFX5, RFXAP and RFXANK at a reduced level. In some embodiments, the reduced level of expression, stated relative to an appropriate control e.g. the expression level in corresponding immune cells not correspondingly engineered, is 0%, for example when both chromosomal copies of a gene are knocked out (e.g. by methods that employ TALEN, zinc fingers, Cas-CLOVER, and/or CRISPR/Cas system), or 50%, for example when one of the two chromosomal copies of a gene is knocked out and there is no compensatory increase in expression of the other chromosomal copy of that gene. In some embodiments, the reduced level of expression, stated relative to the expression level in non-engineered immune cells, is between 0% and 90% or between any two values intermediate between 0% and 90%, for example between 10% and 90%, between 25% and 90%, between 25% and 75%, between 10% and 50%, between 25% and 50%, between 50% and 90%, and between 50% and 75%. Values within one or more of such intermediate ranges can be obtained when, for example, only one chromosomal copy of a gene is knocked out and a compensatory mechanism causes an increase in the level of expression of the remaining chromosomal copy, or reduction in expression is achieved by a method other than gene knockout, such as known knockdown methods e.g. those that employ any of various RNA-based techniques (e.g., shRNA anti-sense RNA, miRNA, siRNA; see, e.g., Lam et al., Mol. Ther.-Nucleic Acids 4:e252 (2015), doi:10.1038/mtna.2015.23; Sridharan and Gogtay, Brit. J. Clin. Pharmacol. 82: 659-72 (2016)). In some embodiments of the population of engineered immune cells disclosed herein, some or all of the engineered cells, e.g. 5-10%, 10-25%, 25-50%, 50-90%, or 90-100% exhibit a reduced level of expression of an MEW class I protein and/or MEW class II protein or complex at the cell surface relative to a suitable control.

In various embodiments, the population of engineered immune cells or a population of immune cells comprising engineered immune cells as disclosed herein comprises at least 10% engineered T cells, at least 20% engineered T cells, at least 30% engineered T cells, at least 40% engineered T cells, at least 50% engineered T cells, at least 75% engineered T cells, at least 90% engineered T cells or 100% engineered T cells. Also provided herein is a population of cells of which at least 10%, at least 20%, at least 30%, at least 40%, at least 50%, at least 75%, at least 90% or 100% are engineered immune cells e.g. engineered T cells as disclosed herein.

In some embodiments, at least 10%, at least 20%, at least 30%, at least 40%, at least 50%, at least 75%, or at least 90% of the engineered cells of the population further express an antigen binding protein. In some embodiments, the antigen binding protein is a chimeric antigen receptor (CAR). In some embodiments, a nucleic acid encoding the CAR is inserted into a disrupted TAP2, NLRC5, β2m, TRAC, CIITA, RFX5, RFXAP or RFXANK locus and/or such an insertion disrupts the locus. In some embodiments, the antigen binding protein is a T cell receptor (TCR). In some embodiments, a nucleic acid encoding the TCR is inserted into a disrupted TAP2, NLRC5, β2m, TRAC, CIITA, RFX5, RFXAP or RFXANK locus and/or such an insertion disrupts the locus.

In certain embodiments of the population of engineered immune cells disclosed herein, at least 10%, at least 20%, at least 30%, at least 40%, at least 50%, at least 75%, or at least 90% of the engineered cells further comprises one or more genomic modifications of one or more of an endogenous TCRa gene and an endogenous CD52 gene.

In an embodiment, the population of engineered immune cells is derived from one or more immune cells obtained from a person, for example, from a person other than the person to whom they will be administered, e.g. obtained from a donor other than the recipient or from a healthy volunteer, or is derived from one or more immune cells obtained from a patient e.g. the person to whom they will be administered, or is derived from one or more iPSCs.

In another aspect, the present disclosure provides a method of making the population of engineered immune cells described herein, wherein the method comprises the use of a gene editing technology, for example, a gene editing technology selected from the group consisting of TALEN, zinc fingers, Cas-CLOVER, and a CRISPR/Cas system, to reduce functional expression of any one or more of TAP2, NLRC5, β2m, TRAC, CIITA, RFX5, RFXAP and RFXANK.

In another aspect, the present disclosure provides a method of determining or measuring the functional expression level of TAP2, NLRC5, β2m, TRAC, CIITA, RFX5, RFXAP and/or RFXANK in the cells of the population of engineered immune cells disclosed herein, wherein the functional expression level is measured by determining the surface expression level of an HLA protein, beta2 microglobulin (B2M) or both an HLA protein and B2M on the surface of the engineered immune cells, and/or is measured by flow cytometry.

In various embodiments of the engineered immune cell described herein and of the population of engineered immune cells disclosed herein, the engineered immune cell is, or one or more of the engineered immune cells of the population, e.g. at least 10%, 20%, 30%, 40%, 50%, 75%, 90% or 100% of the engineered immune cells of the population, are further engineered (e.g. by any of the methods disclosed herein or by any other method known to the person of ordinary skill in the art) to express one or more proteins selected from the group consisting of HLA-E, HLA-E single-chain trimer, HLA-G, HLA-G single-chain trimer, UL18, UL18 single-chain trimer, HLA-A2, HLA-A2 single-chain trimer, and human cytomegalovirus (HCMV) US11 by any method described herein or by any other method known to the person of ordinary skill in the art.

In another aspect, the present disclosure provides a pharmaceutical composition comprising an engineered immune cell as disclosed herein, wherein the composition further comprises one or more pharmaceutically acceptable carrier or excipient. In another aspect, the present disclosure provides a pharmaceutical composition comprising a population of engineered immune cells as disclosed herein, wherein the composition further comprises one or more pharmaceutically acceptable carrier or excipient. In various embodiments of the composition, the engineered immune cell or one or more of the engineered immune cells of the population, e.g. at least 10%, 20%, 30%, 40%, 50%, 75%, 90% or 100% of the engineered immune cells of the population, express(es) one or more proteins selected from the group consisting of HLA-E, HLA-E single-chain trimer, HLA-G, HLA-G single-chain trimer, UL18, UL18 single-chain trimer, HLA-A2, HLA-A2 single-chain trimer, and human cytomegalovirus (HCMV) US11, and/or do(es) not express or express(es) at a reduced level any one or more of CIITA, RFXANK, RFXAP and RFX5 achieved by knockout or knockdown as described herein.

In another aspect, the present disclosure provides a method of treating a condition in a patient comprising administering to the patient an engineered immune cell as disclosed herein, a population of engineered immune cells as disclosed herein, or a pharmaceutical composition as disclosed herein. In an embodiment, the condition is selected from the group consisting of a solid tumor and a liquid tumor.

In another aspect, the present disclosure provides a method of decreasing the surface expression level of an MHC class I protein in an engineered immune cell, in some embodiments, to about 75% or less of the expression level of the MHC class I protein in non-engineered immune cells, the method comprising reducing the functional expression level of any one or more of TAP2, NLRC5, β2m, TRAC, CIITA, RFX5, RFXAP and RFXANK, e.g. to about 75% or less of the expression level in non-engineered immune cells. In an embodiment, the engineered immune cell functionally expresses TAP2 at a level not greater than 75% of the expression level in non-engineered immune cells. In an embodiment, the engineered immune cell functionally expresses NLRC5 at a level not greater than 75% of the expression level in non-engineered immune cells. In an embodiment, the engineered immune cell disclosed herein exhibits a reduced level of expression of an MHC class I protein or complex at the cell surface relative to a suitable control.

In an embodiment, the engineered immune cell disclosed herein is an engineered T cell. In certain embodiments, the engineered immune cell disclosed herein, e.g. the engineered T cell disclosed herein, further expresses an additional protein e.g. a protein encoded by exogenous DNA or a protein whose expression is brought about by further engineering of the cell. In some embodiments, the additional protein is an antigen binding protein. In some embodiments, the antigen binding protein is a chimeric antigen receptor (CAR). In some embodiments, a nucleic acid encoding the additional protein, e.g. the antigen binding protein e.g. the CAR, is introduced into the cell by methods described herein. In some embodiments, the nucleic acid is introduced into a disrupted TAP2, NLRC5, β2m, TRAC, CIITA, RFX5, RFXAP or RFXANK locus or a TAP2, NLRC5, β2m, TRAC, CIITA, RFX5, RFXAP or RFXANK locus is disrupted by insertion of a nucleic acid encoding the additional protein e.g., the antigen binding protein, e.g. the CAR.

In an embodiment of the method disclosed herein, the antigen binding protein is a T cell receptor (TCR) component, e.g. TCR α (TCR alpha), TCR β (TCR beta), TCR γ (TCR gamma) or TCR δ (TCR delta). In an embodiment, a nucleic acid encoding the TCR component is inserted into a disrupted TAP2, NLRC5, β2m, TRAC, CIITA, RFX5, RFXAP or RFXANK locus or a TAP2, NLRC5, β2m, TRAC, CIITA, RFX5, RFXAP or RFXANK locus is disrupted by insertion of a nucleic acid encoding the TCR component.

In a further embodiment of the method disclosed herein, the engineered immune cell further comprises one or more genomic modifications (e.g. knock-out, deletion, knock-down, insertion) of one or more of an endogenous TCR alpha gene and an endogenous CD52 gene. In some embodiments, the genomic modification partially or wholly eliminates functional expression of the modified gene. In a further embodiment of the method disclosed herein, the immune cell is an immune cell obtained from a person, e.g. from a donor other than the person to whom the cells will be administered, e.g. from a healthy volunteer, or is obtained from a patient e.g. the person to whom the cells will be administered, or is derived from an iPSC.

In another aspect, the present disclosure provides a method of making the population of engineered immune cells disclosed herein, wherein the method comprises the use of a gene editing technology, for example a gene editing technology selected from the group consisting of TALEN, zinc fingers, shRNA, Cas-CLOVER, and a CRISPR/Cas system, to reduce functional expression of any one or more of TAP2, NLRC5, β2m, TRAC, CIITA, RFX5, RFXAP and RFXANK in a cell, e.g. in an immune cell. In an embodiment, the gene editing technology introduces a mutation into one or more than one of a TAP2, NLRC5, β2m, TRAC, CIITA, RFX5, RFXAP and RFXANK genetic locus. In an embodiment, the mutation is any one or more of an insertion, e.g. the insertion of one or more nucleotides or base pairs, e.g. the insertion of a sequence that encodes a protein, a deletion of one or more nucleotides or base pairs, and a substitution of one or more nucleotides or base pairs.

In an embodiment of the method disclosed herein, the functional expression level of any one or more of TAP2, NLRC5, β2m, TRAC, CIITA, RFX5, RFXAP and RFXANK is measured by determining the surface expression level of an HLA protein, of beta2 microglobulin (B2M) or of both HLA and B2M on the surface of the engineered immune cell, or is measured by flow cytometry. In an embodiment, the extent of reduction in the surface expression level of one or more of TAP2, NLRC5, β2m, TRAC, CIITA, RFX5, RFXAP and RFXANK is determined relative to the corresponding expression level in a cell of the same type that has not been gene edited.

In an embodiment of the methods disclosed herein, the engineered immune cell expresses an additional protein, which can be any desired protein including an antigen binding protein. In an embodiment, the antigen binding protein comprises a CAR. In an embodiment, a nucleic acid encoding the CAR is inserted into a disrupted TAP2, NLRC5, β2m, TRAC, CIITA, RFX5, RFXAP or RFXANK locus or such an insertion disrupts the locus. In another embodiment, the antigen binding protein is a T cell receptor (TCR) component. In an embodiment, a nucleic acid encoding the TCR is inserted into a disrupted TAP2, NLRC5, β2m, TRAC, CIITA, RFX5, RFXAP or RFXANK locus or such an insertion disrupts the locus. In an embodiment, the method comprises reducing the functional expression level of the disrupted locus. In an embodiment, the method comprises reducing the functional expression level of TAP2. In an embodiment, the method comprises reducing the functional expression level of NLRC5. In an embodiment, the method comprises reducing the functional expression level of RFX5. In an embodiment, the method comprises reducing the functional expression level of CIITA. In certain embodiments, the method further comprises introducing into the engineered immune cell one or more genomic modifications of one or more of a gene encoding a TCR component e.g., a TCRa gene and a CD52 gene.

In another aspect, the present disclosure provides a method of reducing peptide diversity presented on the cell surface e.g. by MEW class I, the method comprising reducing the functional expression level of any one or more of TAP2, NLRC5, β2m, TRAC, CIITA, RFX5, RFXAP and RFXANK, in some embodiments reducing this level to about 90% or less (in other words, a reduction of at least about 10%, e.g. to a level of about 90 or less compared to a control level of 100) or to about 75% or less of a comparable cell that has not been correspondingly altered. In various embodiments, reducing the functional expression level of one or more of TAP2, NLRC5, β2m, TRAC, CIITA, RFX5, RFXAP and RFXANK comprises the use of a gene editing technology selected from the group consisting of TALEN, zinc fingers, Cas-CLOVER, and a CRISPR/Cas system (including for example, Cas9, Cas12 and MAD7). In an embodiment, the method comprises reducing the functional expression level of TAP2. In an embodiment, the method comprises reducing the functional expression level of NLRC5. In an embodiment, the method comprises reducing the functional expression level of RFX5. In an embodiment, the method comprises reducing the functional expression level of CIITA. In an embodiment, the extent of reduction in the expression level of one or more of TAP2, NLRC5, β2m, TRAC, CIITA, RFX5, RFXAP and RFXANK is determined relative to the corresponding expression level in a cell of the same type that has not been gene edited. In an embodiment, the functional expression level of one or more of TAP2, NLRC5, β2m, TRAC, CIITA, RFX5, RFXAP and RFXANK is measured by determining the surface expression level of HLA, beta2 microglobulin (B2M) or both HLA and B2M on the surface of the engineered immune cell.

In another aspect, the present disclosure provides a method of decreasing T cell-mediated killing of allogeneic cells comprising reducing the functional expression level of any one or more of TAP2, NLRC5, β2m, TRAC, CIITA, RFX5, RFXAP and RFXANK in an engineered immune cell such as an engineered T cell. In some embodiments, the method results in a reduced level of expression, stated relative to the expression level in non-engineered immune cells, that is 0%, for example when both chromosomal copies of a gene are knocked out, or 50%, for example when one of the two chromosomal copies of a gene is knocked out and there is no compensatory increase in expression of the other chromosomal copy of that gene. In some embodiments, the method results in a reduced level of expression, stated relative to the expression level in non-engineered immune cells, that is between 0% and 90% or between any two values intermediate between 0% and 90%, for example between 10% and 90%, between 25% and 90%, between 25% and 75%, between 10% and 50%, between 25% and 50%, between 50% and 90%, and between 50% and 75%. In some embodiments, reducing the functional expression level of one or more of TAP2, NLRC5, β2m, TRAC, CIITA, RFX5, RFXAP and RFXANK comprises the use of a gene editing technology, for example, any one or more of TALEN, zinc fingers, Cas-CLOVER, and/or CRISPR/Cas system, and/or any one or more known knockdown methods e.g. those that employ any of various RNA-based techniques (e.g., shRNA, anti-sense RNA, miRNA, siRNA). In an embodiment, the method comprises reducing the functional expression level of TAP2. In an embodiment, the method comprises reducing the functional expression level of NLRC5. In an embodiment, the method comprises reducing the functional expression level of RFX5. In an embodiment, the method comprises reducing the functional expression level of CIITA. In an embodiment, the extent of reduction in the expression level of one or more of TAP2, NLRC5, β2m, TRAC, CIITA, RFX5, RFXAP and RFXANK is determined relative to the corresponding expression level in a cell of the same type that has not been so altered and/or manipulated.

In an embodiment of the method of decreasing T cell-mediated killing of allogeneic cells disclosed herein, the functional expression level of one or more of TAP2, NLRC5, β2m, TRAC, CIITA, RFX5, RFXAP and RFXANK is measured by determining the surface expression level of HLA, beta2 microglobulin (B2M) or both HLA and B2M on the surface of the engineered immune cell. In an embodiment, the surface expression level of one or more of TAP2, NLRC5, β2m, TRAC, CIITA, RFX5, RFXAP and RFXANK is measured by flow cytometry. In an embodiment, the method comprises introducing one or more genomic modifications of one or more of a gene encoding a TCR component e.g. a TCRa gene and a CD52 gene.

In some embodiments of the method of decreasing T cell-mediated killing of allogeneic cells disclosed herein, the functional expression level of any one or more of TAP2, NLRC5, β2m, TRAC, CIITA, RFX5, RFXAP and RFXANK in engineered immune cells of the present disclosure is assayed by measuring the degree to which the engineered immune cells survive in the presence of effector cells e.g. T cells, in comparison to the degree to which non-engineered, but otherwise comparable e.g. identical, immune cells survive under the same conditions.

In an aspect, the present disclosure provides an engineered immune cell that functionally expresses one or more of TAP2, NLRC5, β2m, TRAC, RFX5, RFXAP, CIITA and RFXANK at a reduced level. In various embodiments, TRAC and RFX5 are functionally expressed at a reduced level. In various embodiments, the cell exhibits a reduced level of expression of an MEW class I protein or complex at the cell surface, a reduced level of expression of an MHC class II protein or complex at the cell surface, or a reduced level of expression of an MEW class I protein or complex at the cell surface and a reduced level of expression of an MHC class II protein or complex at the cell surface. In various embodiments, the cell is a T cell.

In various embodiments, the engineered immune cell disclosed herein further expresses an additional protein. In some embodiments, the additional protein is an antigen binding protein. In some embodiments, the antigen binding protein is a chimeric antigen receptor (CAR). In some embodiments, the antigen binding protein is a T cell receptor (TCR). In certain embodiments, the engineered immune cell comprises a nucleic acid encoding the additional protein. In some embodiments, the nucleic acid encoding the additional protein is located within a disrupted TAP2, NLRC5, CIITA, RFX5, RFXANK, β2m or RFXAP locus and/or causes or creates a disruption in such a locus.

In various embodiments, the engineered immune cell disclosed herein comprises or further comprises one or more genomic modifications of one or more of an endogenous TCRα (TCRα or TCR alpha) gene and an endogenous CD52 gene.

In various embodiments, the engineered immune cell disclosed herein is or is derived from an immune cell obtained from a healthy volunteer or a patient, or is derived from an iPSC.

In an aspect, the present disclosure provides a method of making an engineered immune cell disclosed herein comprising the use of a gene editing technology selected from the group consisting of TALENs, zinc fingers, Cas-CLOVER, and a CRISPR/Cas system to reduce functional expression of one or more of TAP2, NLRC5, β2m, TRAC, RFX5, RFXAP, CIITA and RFXANK.

BRIEF DESCRIPTION OF THE DRAWINGS

In FIG. 1, T cell killing is activated because the allogeneic cell's HLA complex presents a foreign antigen (narrow rectangle) and the T cell's TCR/CD3 complex recognizes the antigen as foreign. NK cell killing is not activated because there is no "missing self" because, as illustrated, the allogeneic cell presents the HLA complexes Classical HLA, HLA-E, and HLA-G (each of which displays a peptide).

FIG. 2A: Quantification of flow cytometry data measuring degranulation of NK cells after 3 h incubation alone or with autologous or allogeneic T cells±b2m KO in the presence of monensin (GolgiStop) and anti-CD107a antibody. FIG. 2B. Target composition over time of surface MHC+ (b2m WT) and surface MHC$^{neg}$ (b2m KO) incubated with NK cells. The composition of b2m WT:b2m KO was 1:1 (50%:50%) at the start of the incubation. Mean+SD is shown for 3 experiments. WT, wild-type. KO, knockout.

FIG. 6A. Primary T cells from an HLA-A2+ donor (left bar of each pair) or from an HLA-A2⁻ donor (right bar of each pair) were edited via CRISPR with mock, TAP2, or b2m sgRNAs and then transduced with BFP-P2A− MART1 antigen. Unpurified edited cells were then incubated for 72 h alone (no effectors) or with autologous effector T cells transduced with MART1-specific F5 TCR (effectors). Data are gated on unedited (surface β2m+), antigen-expressing (BFP+) cells and are plotted for % unedited BFP+ cells surviving in the presence vs absence of effector cells (mean+SD for 3 technical replicates). FIG. 6B. Same experiment as in FIG. 6A except data are gated on edited (surface β2m$^{neg}$), antigen-expressing (BFP+) cells and are plotted for % edited BFP+ cells surviving in the presence vs absence of effector cells (mean+SD for 3 technical replicates). NA, not applicable because there are no edited cells in the "No KO" control. FIG. 6C. Similar to experiment in FIGS. 6A and 6B but independently performed with addition of NLRC5 KO. Data are gated on edited (surface β2m$^{neg}$), antigen-expressing (BFP+) cells and are plotted for % edited BFP+ cells surviving in the presence vs absence of effector cells (mean+SD for 2 technical replicates). NA, not applicable because there are no edited cells in the "No KO" control; KO, knockout.

FIG. 8A. Pseudocolored flow cytometry plots exhibiting surviving target T cells under indicated conditions. Data are from incubation with NK cells from a single allogeneic donor. FIG. 8B. Measurement of percent of surviving cells that are surface b2m negative (i.e. b2m, TAP2, or NLRC5 KO) normalized to condition lacking NK effector cells. Mean±SD of 4 datapoints are shown (2 technical replicates for each of 2 allogeneic NK donors). FIG. 8C. Representative histograms of surface 02m staining for T cells in experiments from FIG. 8B. NK1054 and NK1241 are two allogeneic NK donors. Dotted vertical line approximates the mean fluorescence intensity of surface 02m for TRAC KO T cells (no WIC-related modifications) and is included as a visual reference across histogram plots. Coinc, coincubation; KO, knockout;

FIG. 9A. Primary T cells gene edited for TRAC KO in combination with β2m, TAP2, or NLRC5 KO can be transduced with 10G1K DLL3 CAR at comparable rates to unedited cells. Pan T cells were gene edited via CRISPR/Cas9 and transduced with lentivirus to enable DLL3 CAR expression. Transduction efficiency was determined by flow for percentage of cells expressing a BFP reporter gene co-expressed on the CAR lentiviral vector.

FIG. 9B. Expansion of engineered CAR T cells was determined by counting viable cells on the ViCell cell counter and normalizing to the initial seeding density at day 0.

FIGS. 10A-10C. NLRC5 KO does not impair DLL3 CAR-mediated cytotoxicity.

FIG. 10A. Short-term killing of DLL3$^{high}$-expressing WM266.4 tumor cells and (FIG. 10B) DLL3$^{low}$-expressing DMS273 tumor cells. Growth curves of tumor cells generated via live cell imaging with anti-DLL3 CAR' T cells at varying E:T ratios. FIG. 10C. Serial killing of DLL3$^{high}$-expressing WM266.4 tumor cells. Mean±SD of technical triplicate shown.

FIGS. 11A-11B. Screening sgRNA for RFX complex KO. Confirmation of RFX5 KO for dual MHC-I/II downmodulation. Mean fluorescence intensity (MFI) of MHC-I (FIG. 11A) and MHC-II (FIG. 11B) assessed by flow cytometry 7 days post gene editing.

FIGS. 12A-12B. Downmodulation of MHC-I/II Expression. Mean fluorescence intensity (MFI) of (FIG. 12A) MHC-I and (FIG. 12B) MHC-II in gene-edited T cells assessed by flow cytometry 5 post gene editing for 3 independent T cell donors. Mean±SD of biological triplicate shown.

FIG. 13A. Expansion of T cells with TRAC KO+/−immune evasion KO modifications in 3 independent donors. Fold expansion relative to number of cells gene edited on day 2. Mean±SD of 2 technical replicates shown. FIG. 13B. Growth of graft T cells in the absence of IL-2.20K cells were seeded in a 96-well plate with 20 IU/mL IL-2. On day 4, media was exchanged without IL-2. Media was re-fed every 2-3 days thereafter. Mean±SD of 6 technical replicates shown.

FIG. 14A: CD4+ cells, FIG. 14B: CD8+ cells, or FIG. 14C: pan T cells were purified thereafter and co-cultured with graft T cells for 48 h at a 1:1 E:T ratio. One-way killing of graft T cells assessed by flow cytometry. Mean±SD of technical triplicate shown. % Survival=Cell Counts/(Cell Counts without Effectors)×100. The graft cells were edited to make KO cells (TRAC, β2m, NLRC5, or RFX5), and the KO graft cells were co-cultured with the primed CD4+, CD8+, and pan T cells. The number of graft KO cells that survived co-culturing with the primed T cells was determined. A significantly higher proportion of RFX5 KO cells than TRAC KO cells survived the co-culturing with the primed cells.

FIG. 15A. NK cells were isolated from allogeneic PBMCs and co-cultured with graft T cells in the presence of 1000 IU/mL IL-2 for 48 h at a 1:1 E:T ratio. One-way killing of graft T cells assessed by flow cytometry. The graft cells were edited to make KO (TRAC) or double KO (TRAC+ one of β2m, NLRC5, or RFX5), and the KO graft cells were co-cultured with the NK cells. The number of graft KO cells that survived co-culturing with the NK cells was determined. About half or more of the TRAC+ NLRC5 KO cells and about half or more of the TRAC+RFX5 KO cells survived the co-culturing with the NK cells. Mean±SD of biological triplicate shown. NK cells were obtained from PBMCs from 3 different donors. Each data point represents killing by cells from one of those donors. % Survival=Cell Counts/(Cell Counts without Effectors)×100. FIG. 15B. Expansion of allogeneic NK cells after co-culture of allo-PBMCs with graft T cells at a 10:1 E:T ratio for 7 days. Mean±SD of 6 biological replicates shown. The data indicate that TRAC KO+/−RFX5 KO or NLRC5 KO do not induce significant NK cell expansion. Allogeneic NK cell counts were measured after co-culture with gene-edited graft cells and compared to cell counts in the absence of graft cells. 1-fold change means NK cells were essentially not activated/ expanded. In this assay, PBMCs were cultured with graft T cells and NK cells were counted based on NK-specific markers. *:p<0.05; ****:p<0.001, One-way ANOVA Holm-Sidak.

FIG. 17A. US11 overexpression reduces MHC-I expression and can be combined with MRCS KO to significantly reduce MHC-I levels. FIG. 17B. US11 overexpression mitigates killing by primed alloreactive T cells. US11 can be combined with MRCS KO to further reduce killing. Graft cells were cultured with primed T cells for 48 h at a 1:1 E:T ratio and survival was determined by flow cytometry. Mean±SD for 3 donors tested shown. FIG. 17C. US11 overexpression minimally increases NK scrutiny. When combined with MRCS KO, NK reactivity increases but not to same extent as b2m KO. Graft cells were cultured with allogeneic NK cells with 1000

IU/mL IL-2 for 48 h at a 1:1 E:T ratio and survival was determined by flow cytometry. Mean±SD for 3 donors tested shown. FIG. 17D. US11 and US11+NLRC5 KO T cells persist better than TRAC KO only. Graft cells were cultured with allogeneic PBMCs cells with 20 IU/mL IL-2 for 9 days at a 10:1 E:T ratio and survival was determined by flow cytometry. Mean±SD for 3 donors tested shown. % Survival=Cell Counts/(Cell Counts without Effectors)×100.

FIGS. 21A-21B. Expansion of host CD8 T cells and survival of graft CD19 CAR T cells with various KO after co-culturing with allogeneic PBMCs. Five unique graft/PBMC pairs were shown. Allogeneic PBMCs were co-cultured with TRAC KO CD19 CAR T cells containing various gene editing modifications (TRAC KO alone or with KO of one of β2m, NLRC5, RFX5, or CIITA) for 9 days at a 10:1 E:T ratio. Expansion of host CD8 T cells (FIG. 21A) was determined by flow cytometry using anti-CD8 antibody (BioLegend, Cat #344709) and anti-HLA-A2 antibody (BioLegend Cat #343326) and normalized to the PBMCs cultured without graft cells. Survival of graft CAR T cells (FIG. 21B) was determined by flow cytometry and normalized to the graft CD19 CAR T cells cultured without effector cells. Individual dot representing each unique PBMC/graft pair and mean±SEM for 5 pairs shown.

DETAILED DESCRIPTION

The instant disclosure provides a gene editing strategy for providing a therapeutic allogeneic cell product that does not provoke, or provokes to a reduced degree, rejection by the recipient's immune system. This permits the cell product to persist longer in the recipient and thus promotes and/or improves the therapeutic effect. The present strategy minimizes the diversity of peptides presented by an allogeneic cell product while also minimally perturbing the level of MHC on the cell surface. This is achieved through genomic knockout of one or more of TAP2, NLRC5, β2m, TRAC, CIITA, RFX5, RFXAP and RFXANK, the products of which function in peptide presentation by the cell.

Figure 4A:
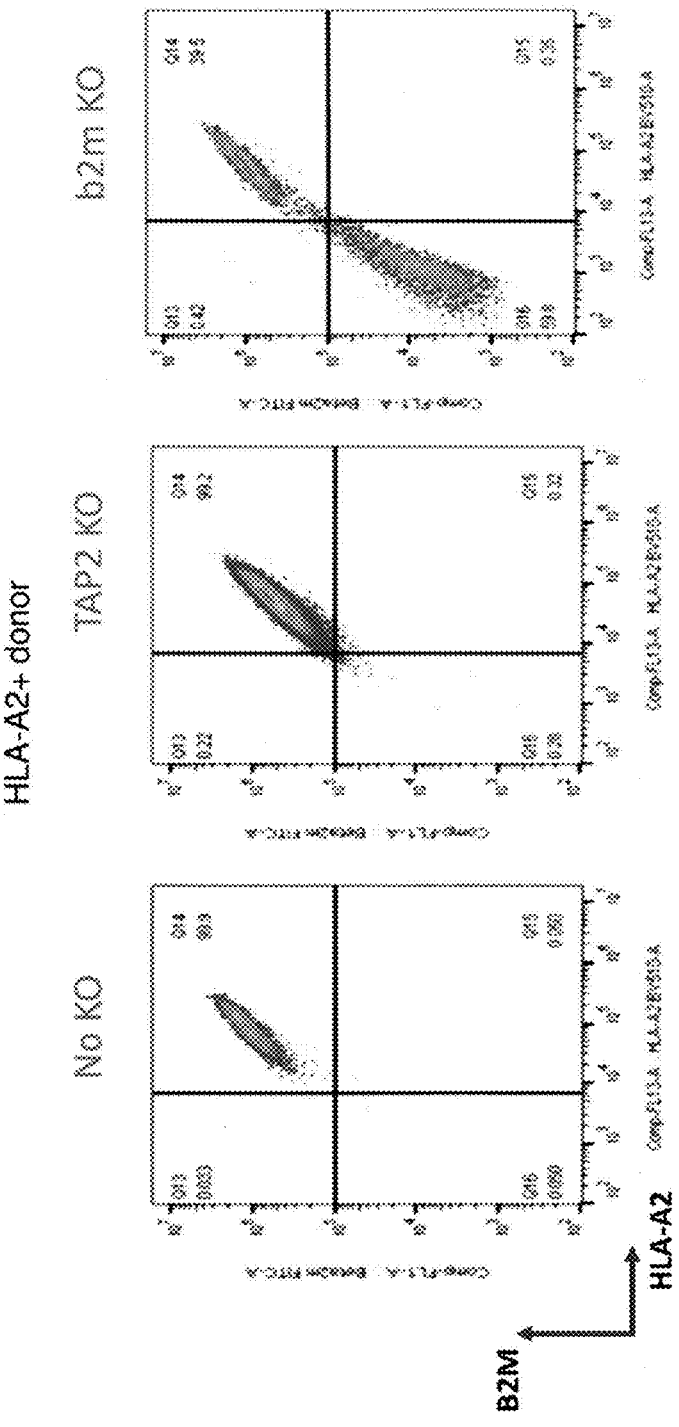
FIGS. 4A-4B. Pseudocolored flow cytometry plots measuring 02m levels on the surface of T cells following CRISPR/Cas9-mediated knockout of, in FIG. 4A, TAP2 or b2m genes (in cells from an HLA-A2+ donor) and, in FIG. 4B, NLRC5 gene (in cells from an HLA-A2− donor). KO, knockout.

In one aspect of the present disclosure, the gene editing target is the TAP2 component of the transporter associated with antigen processing (TAP). The dominant pathway by which MHC class I molecules are loaded with peptide is TAP-dependent: peptides generated by the proteasome (or the IFN-γ-inducible immunoproteasome) are imported to the endoplasmic reticulum (ER) via TAP and then loaded on MHC class I. A minority of peptides—substantially derived from signal peptides—are loaded through an alternative TAP- and proteasome-independent pathway following signal sequence cleavage by the ER-resident signal peptide peptidase (SPP). Knocking out TAP2 reduces surface β2m modestly (2-fold decrease after selection for KO cells) compared to the profound (10-100-fold) reduction in surface β2m in β2m KO cells (see FIG. 4A).

Figure 4B:
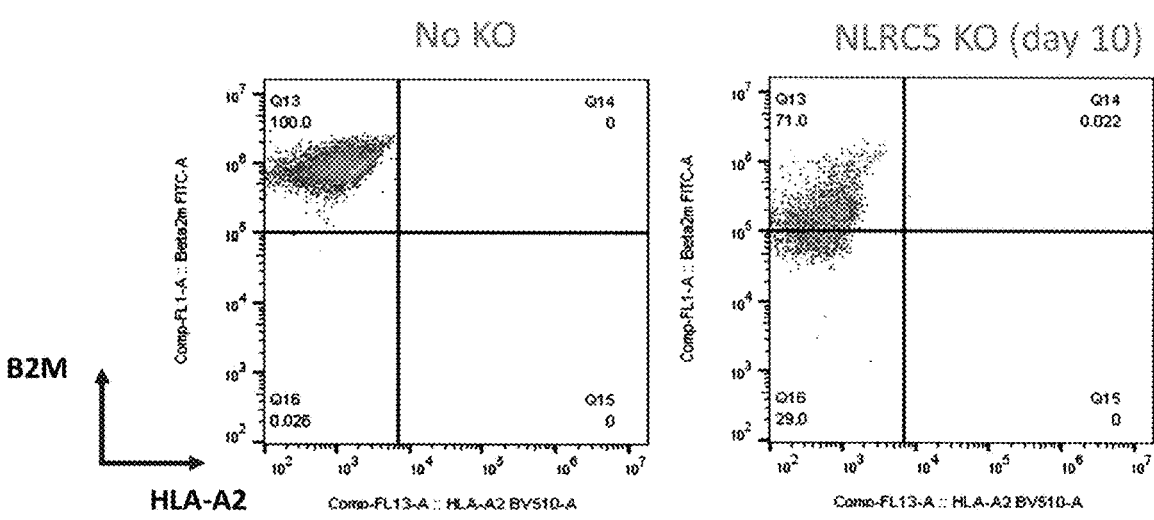

In a second aspect of the present disclosure, the gene editing target is a member of the nucleotide-binding domain and leucine-rich repeat containing receptor (NLR) family called NLR caspase recruitment domain containing 5 (NLRC5). CRISPR/Cas9-mediated knockout of NLRC5 results in a 2.5-fold reduction in the level of surface β2m (see FIG. 4B).

The gene editing strategies disclosed herein surprisingly reduce peptide display sufficiently to reduce cell death at the hands of the recipient's T cell response while at the same time not reducing peptide display so much that killing by the recipient's NK cells is provoked. The strategies provided herein therefore represent a significant advance in allogeneic CAR-T therapy and other allogeneic cell therapies. The gene editing strategies provided herein confer the additional advantage that the NLRC5 knockout effect of suppressing MHC class I presentation should occur in the presence or absence of IFN-γ. This conclusion is supported by the finding that IFN-γ-induced MHC class I upregulation is dependent on NLRC5.

General Techniques

The practice of the instant disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Gene editing techniques using TALENs, CRISPR/Cas9, and megaTAL nucleases, for example, are within the skill of the art and explained fully in the literature, such as T. Gaj et al., Genome-Editing Technologies: Principles and Applications, *Cold Spring Harb Perspect Biol* 2016; 8:a023754 and citations therein.

Definitions

As used herein "autologous" means that cells, a cell line, or population of cells used for treating subjects that are obtained from said subject.

As used herein "allogeneic" means that cells or population of cells used for treating subjects that are not obtained from said subject, but instead from a donor.

As used herein, the term "endogenous" refers to any material from or produced inside an organism, cell, tissue or system.

As used herein, the term "exogenous" refers to any material introduced from or produced outside an organism, cell, tissue or system.

As used herein, "immune cell" refers to a cell of hematopoietic origin functionally involved in the initiation and/or execution of innate and/or adaptative immune response. Examples of immune cells include T cells, e.g., alpha/beta T cells and gamma/delta T cells, Regulatory T (Treg) cells, B cells, natural killer (NK) cells, natural killer T (NKT) cells, mast cells, and myeloid-derived phagocytes.

As used herein, the term "expression" refers to the transcription and/or translation of a particular nucleotide sequence driven by a promoter.

As used herein, "expression vector" refers to a vector comprising a recombinant polynucleotide comprising expression control sequences operatively linked to a nucleotide sequence to be expressed. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

Engineered immune cells of the present disclosure express e.g. functionally express one or more of TAP2, NLRC5, β2m, TRAC, CIITA, RFX5, RFXAP and RFXANK at a reduced level as described herein and optionally further comprise additional features. For example, they can functionally express an antigen binding protein from an exogenous nucleic acid encoding the antigen binding protein introduced into the cell by techniques described herein, and/or they can comprise genomic modifications e.g. mutations at endogenous genes such as TCRa and/or CD52 that decreases or eliminates functional expression of the gene, and/or they can express one or more additional proteins from an exogenous nucleic acid encoding the antigen binding protein introduced into the cell by techniques described herein. As described herein, engineered immune cells of the present disclosure can derive, e.g., be prepared from cells, e.g., immune cells obtained from various sources.

As used herein, to "functionally express" a gene means that a gene is expressed and that expression yields a functioning gene end product. For example, if a gene encodes a protein, then a cell functionally expresses the gene if expression of the gene ultimately produces a properly functioning protein. Thus, if a gene is not transcribed, or expression of the gene ultimately produces an RNA that is not translated or translation yields only a non-functioning protein e.g. the protein does not fold correctly or is not transported to its site of action (e.g. membrane, for membrane-bound proteins), for example, then the gene is not functionally expressed. Functional expression can be measured directly (e.g. by assaying for the gene product itself) or indirectly (e.g. by assaying for the effects of the gene product).

As used herein, "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter).

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

"Promoter" and "promoter sequence" are used interchangeably and refer to a DNA sequence capable of controlling the expression of a coding sequence or functional RNA. In general, a coding sequence is located 3' to a promoter sequence. It is understood by those skilled in the art that different promoters can direct the expression of a gene in different tissues or cell types, or at different stages of development, or in response to different environmental or physiological conditions.

In any of the vectors of the present disclosure, the vector optionally comprises a promoter disclosed herein.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the instant disclosure.

The term "extracellular ligand-binding domain" as used herein refers to an oligo- or polypeptide that is capable of binding a ligand. Preferably, the domain will be capable of interacting with a cell surface molecule. For example, the extracellular ligand-binding domain can be chosen to recognize a ligand that acts as a cell surface marker on target cells associated with a particular disease state. The term "stalk domain" is used herein to refer to any oligo- or polypeptide that functions to link the transmembrane domain to the extracellular ligand-binding domain. In particular, stalk domains are used to provide more flexibility and accessibility for the extracellular ligand-binding domain.

The term "intracellular signaling domain" refers to the portion of a protein which transduces the effector signal function signal and directs the cell to perform a specialized function.

A "co-stimulatory molecule" as used herein refers to the cognate binding partner on a T cell that specifically binds with a co-stimulatory ligand, thereby mediating a co-stimulatory response by the cell, such as, but not limited to proliferation. Co-stimulatory molecules include, but are not limited to, an MEW class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

A "co-stimulatory ligand" refers to a molecule on an antigen presenting cell that specifically binds a cognate co-stimulatory signal molecule on a T cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1 BBL, OX40L, inducible costimulatory ligand (ICOS-L), intercellular adhesion molecule (ICAM, CD30L, CD40, CD70, CD83, HLA-G, MICA, M1 CB, HVEM, lymphotoxin β receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1 BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also antigen-binding fragments thereof (such as Fab, Fab', F(ab')2, and Fv), and any other modified configuration of the immunoglobulin molecule that comprises an antigen recognition site including, for example without limitation, single chain (scFv) and domain antibodies (including, for example, shark and camelid antibodies), and fusion proteins comprising an antibody. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen-binding fragment" or "antigen binding portion" of an antibody, as used herein, refers to one or more fragments of an intact antibody that retain the ability to specifically bind to a given antigen. Antigen binding functions of an antibody can be performed by fragments of an intact antibody. Examples of binding fragments encompassed within the term "antigen binding fragment" of an antibody include Fab; Fab'; F(ab')2; an Fd fragment consisting of the VH and CH1 domains; an Fv fragment consisting of the VL and VH domains of a single arm of an antibody; a single domain antibody (dAb) fragment (see, e.g., Ward et al., Nature 341:544-546, 1989), and an isolated complementarity determining region (CDR).

An antibody, an antibody conjugate, or a polypeptide that "specifically binds" to a target is a term well understood in the art, and methods to determine such specific binding are also well known in the art. A molecule is said to exhibit "specific binding" if it reacts or associates more frequently, more rapidly, with greater duration and/or with greater affinity with a particular cell or substance than it does with alternative cells or substances. An antibody "specifically binds" to a target if it binds with greater affinity, avidity, more readily, and/or with greater duration than it binds to other substances. It is also understood that by reading this definition, for example, an antibody (or moiety or epitope) that specifically binds to a first target may or may not specifically bind to a second target. As such, "specific binding" does not necessarily require (although it can include) exclusive binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are several techniques for determining CDRs, e.g., an approach based on cross-species sequence variability (i.e., Kabat et al. Sequences of Proteins of Immunological Interest, (5th ed., 1991, National Institutes of Health, Bethesda MD)); an approach based on crystallographic studies of antigen-antibody complexes (Al-lazikani et al., 1997, J. Molec. Biol. 273:927-948), the Chothia system (i.e., Chothia and Lesk, J. Mol. Biol. (1987) 196(4):901-917. As used herein, a CDR can refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs can be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs can also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs can be identified as the residues that make enthalpic contributions to antigen binding. See, e.g., Makabe et al., Journal of Biological Chemistry, 283:1 156-1 166, 2008. Still other CDR boundary definitions may not strictly follow one of the above approaches, but will nonetheless overlap with at least a portion of the Kabat CDRs, although they can be shortened or lengthened in light of prediction or experimental findings that particular residues or groups of residues or even entire CDRs do not significantly impact antigen binding. As used herein, a CDR can refer to CDRs defined by any approach known in the art, including combinations of approaches. The methods used herein can utilize CDRs defined according to any of these approaches. For any given embodiment containing more than one CDR, the CDRs can be defined in accordance with any of Kabat, Chothia, extended, AbM, contact, AHo and/or conformational definitions.

Antibodies of the instant disclosure can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide can comprise modified nucleotides, such as methylated nucleotides and their analogs. If present, modification to the nucleotide structure can be imparted before or after assembly of the chain. The sequence of nucleotides can be interrupted by non-nucleotide components. A polynucleotide can be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "transfection" refers to the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

As used herein, "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure. The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the instant disclosure. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein, "treatment" is an approach for obtaining a beneficial or desired clinical result. For purposes of the instant disclosure, beneficial or desired clinical results include, but are not limited to, one or more of the following: reducing the proliferation of (or destroying) neoplastic or cancerous cells, inhibiting metastasis of neoplastic cells, shrinking or decreasing the size of tumor, remission of a disease (e.g., cancer), decreasing symptoms resulting from a disease (e.g., cancer), increasing the quality of life of those suffering from a disease (e.g., cancer), decreasing the dose of other medications required to treat a disease (e.g., cancer), delaying the progression of a disease (e.g., cancer), curing a disease (e.g., cancer), and/or prolong survival of subjects having a disease (e.g., cancer).

"Ameliorating" means a lessening or improvement of one or more symptoms as compared with not administering a treatment. "Ameliorating" also includes shortening or reduction in duration of a symptom. As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various diseases or conditions (such as for example cancer), decreasing the dose of other medications required to treat the disease, enhancing the effect of another medication, and/or delaying the progression of the disease. An effective dosage can be administered in one or more administrations. For purposes of the instant disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" can be considered in the context of administering one or more therapeutic agents, and a single agent can be considered to be given in an effective amount if, in conjunction with one or more other agents, a desirable result can be or is achieved.

As used herein, a "subject" is any mammal, e.g a human, or a monkey. Mammals include, but are not limited to, farm animals, sport animals, pets, primates, horses, dogs, cats, mice and rats. In an exemplary embodiment, the subject is a human. In an exemplary embodiment, the subject is a monkey, e.g. a cynomolgus monkey.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "pharmaceutically acceptable carrier" or "pharmaceutically acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions of the instant disclosure comprising such carriers are formulated by well-known conventional methods (see, for example, Remington's Pharmaceutical Sciences, 18th edition, A. Gennaro, ed., Mack Publishing Co., Easton, PA, 1990; and Remington, The Science and Practice of Pharmacy 21 st Ed. Mack Publishing, 2005).

As used herein, "alloreactivity" refers to the ability of T cells to recognize MEW complexes that were not encountered during thymic development. Alloreactivity manifests itself clinically as host-versus-graft rejection and graft-versus-host disease.

Reference to "about" a value or parameter herein includes (and describes) embodiments that are directed to plus or minus 1, 2, 3, 4, 5, 6, 7, 8, 9 or 10% that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of and/or "consisting essentially of" are also provided.

Where aspects or embodiments of the instant disclosure are described in terms of a Markush group or other grouping of alternatives, the instant disclosure encompasses not only the entire group listed as a whole, but also each member of the group individually and all possible subgroups of the main group, and also the main group absent one or more of the group members. The instant disclosure also envisages the explicit exclusion of one or more of any of the group members in the disclosed and/or claimed embodiments.

Unless otherwise defined, all technical and scientific terms used herein have the same meaning as commonly understood by one of ordinary skill in the art to which the present disclosure belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the instant disclosure. The materials, methods, and examples are illustrative only and not intended to be limiting.

An "antigen binding protein" comprises one or more antigen binding domains. An "antigen binding domain" as used herein means any polypeptide that binds a specified target antigen. In some embodiments, the antigen binding domain binds to an antigen on a tumor cell. In some embodiments, the antigen binding domain binds to an antigen on a cell involved in a hyperproliferative disease or to a viral or bacterial antigen.

Antigen binding domains include, but are not limited to, antibody binding regions that are immunologically functional fragments. The term "immunologically functional fragment" (or "fragment") of an antigen binding domain is a species of antigen binding domain comprising a portion (regardless of how that portion is obtained or synthesized) of an antibody that lacks at least some of the amino acids present in a full-length chain, but which is still capable of specifically binding to a target antigen. Such fragments are biologically active in that they bind to the target antigen and can compete with other antigen binding domains, including intact antibodies, for binding to a given epitope.

Immunologically functional immunoglobulin fragments include, but are not limited to, scFv fragments, Fab fragments (Fab', F(ab')2, and the like), one or more complementarity determining regions ("CDRs"), a diabody (heavy chain variable domain on the same polypeptide as a light chain variable domain, connected via a short peptide linker that is too short to permit pairing between the two domains on the same chain), domain antibodies, bivalent antigen binding domains (comprises two antigen binding sites), multi specific antigen binding domains, and single-chain antibodies. These fragments can be derived from any mammalian source, including but not limited to human, mouse, rat, camelid or rabbit. As will be appreciated by one of skill in the art, an antigen binding domain can include non-protein components.

The variable regions typically exhibit the same general structure of relatively conserved framework regions (FR) joined by the 3 hypervariable regions (CDRs). The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. By convention, CDR regions in the heavy chain are typically referred to as HC CDR1, CDR2, and CDR3. The CDR regions in the light chain are typically referred to as LC CDR1, CDR2, and CDR3.

In some embodiments, antigen binding domains comprise one or more complementarity binding regions (CDRs) present in the full-length light or heavy chain of an antibody, and in some embodiments comprise a single heavy chain and/or light chain or portion thereof. These fragments can be produced by recombinant DNA techniques or can be produced by enzymatic or chemical cleavage of antigen binding domains, including intact antibodies.

In some embodiments, the antigen binding domain is an antibody or fragment thereof, including one or more of the complementarity determining regions (CDRs) thereof. In some embodiments, the antigen binding domain is a single chain variable fragment (scFv), comprising light chain CDRs: CDR1, CDR2 and CDR3, and heavy chain CDRs: CDR1, CDR2 and CDR3.

The assignment of amino acids to each of the framework, CDR, and variable domains is typically in accordance with numbering schemes of Kabat numbering (see, e.g., Kabat et al. in Sequences of Proteins of Immunological Interest, 5th Ed., NIH Publication 91-3242, Bethesda Md. 1991), Chothia numbering (see, e.g., Chothia & Lesk, (1987), J Mol Biol 196: 901-917; Al-Lazikani et al., (1997) J Mol Biol 273: 927-948; Chothia et al., (1992) J Mol Biol 227: 799-817; Tramontano et al., (1990) J Mol Biol 215(1): 175-82; and U.S. Pat. No. 7,709,226), contact numbering, the AbM scheme (Antibody Modeling program, Oxford Molecular) or the AHo system (Honneger and Pluckthun, J Mol Biol (2001) 309(3):657-70).

In some embodiments, the antigen binding domain is a recombinant antigen receptor. The term "recombinant antigen receptor" as used herein refers broadly to a non-naturally occurring surface receptor that comprises an extracellular antigen-binding domain or an extracellular ligand-binding domain, a transmembrane domain and an intracellular domain. In some embodiments, the recombinant antigen receptor is a chimeric antigen receptor (CAR). Chimeric antigen receptors (CARs) are well-known in the art. A CAR is a fusion protein that comprises an antigen recognition moiety, a transmembrane domain and T cell activation domains (see, e.g., Eshhar et al., Proc. Natl. Acad. Sci. USA, 90(2): 720-724 (1993)).

In some embodiments, the intracellular domain of a recombinant antigen receptor comprises a co-stimulatory domain and an ITAM-containing domain. In some embodiments, the intracellular domain of a recombinant antigen receptor comprises an intracellular protein or a functional variant thereof (e.g., truncation(s), insertion(s), deletion(s) or substitution(s)).

The term "extracellular ligand-binding domain" or "extracellular antigen-binding domain" as used herein refers to a polypeptide that is capable of binding a ligand or an antigen or capable of interacting with a cell surface molecule, such as a ligand or a surface antigen. For example, the extracellular ligand-binding or antigen-binding domain can be chosen to recognize a ligand that acts as a cell surface marker on target cells associated with a particular disease state, e.g., a tumor-specific antigen. In some embodiments, the antigen-binding domain comprises an antibody, or an antigen binding fragment or an antigen binding portion of an antibody. In some embodiments, the antigen binding domain comprises an Fv or scFv, an Fab or scFab, an F(ab')2 or a scF(ab')2, an Fd, a monobody, a affibody, a camelid antibody, a VHH antibody, a single domain antibody, or a darpin. In some embodiments, the ligand-binding domain comprises a partner of a binding pair, such as a ligand that binds to a surface receptor, or an ectodomain of a surface receptor that binds to a ligand.

The term "stalk domain" or "hinge domain" are used interchangeably herein to refer to any polypeptide that functions to link the transmembrane domain to the extracellular ligand-binding domain. In particular, stalk domains are often used to provide more flexibility and accessibility for the extracellular ligand-binding domain.

The term "intracellular signaling domain" refers to the portion of a protein which transduces the effector signal function signal and directs the cell to perform a specialized function.

Vectors

Expression vectors and methods for the administration of polynucleotide compositions are known in the art and further described herein.

In another aspect, the instant disclosure provides a method of making any of the polynucleotides described herein.

Polynucleotides complementary to any such sequences are also encompassed by the instant disclosure. Polynucleotides can be single-stranded (coding or antisense) or double-stranded, and can be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences can, but need not, be present within a polynucleotide of the instant disclosure, and a polynucleotide can, but need not, be linked to other molecules and/or support materials.

Polynucleotides can comprise a native sequence (i.e., an endogenous sequence that encodes an antibody or a portion thereof) or can comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide can generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof. Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence can be compared to a reference sequence of the same number of contiguous positions after the two sequences are optimally aligned.

Optimal alignment of sequences for comparison can be conducted using the Megalign program in the Lasergene suite of bioinformatics software (DNASTAR, Inc., Madison, W1), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA.; Higgins, D. G. and Sharp, P. M., 1989, CABIOS 5:151-153; Myers, E. W. and Muller W., 1988, CABIOS 4:1 1-17; Robinson, E. D., 1971, Comb. Theor. 1 1:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA.; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window can comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants can also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/m\), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the instant disclosure. Further, alleles of the genes comprising the polynucleotide sequences provided herein are within the scope of the instant disclosure. Alleles are endogenous genes that are altered as a result of one or more mutations, such as deletions, additions and/or substitutions of nucleotides. The resulting mRNA and protein can, but need not, have an altered structure or function. Alleles can be identified using standard techniques (such as hybridization, amplification and/or database sequence comparison).

The polynucleotides of the instant disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further described herein. Polynucleotides can be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in, e.g., U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors can be constructed according to standard techniques, or can be selected from a large number of cloning vectors available in the art. While the cloning vector selected can vary according to the host cell intended to be used, useful cloning vectors will generally have the ability to self-replicate, can possess a single target for a particular restriction endonuclease, and/or can carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the instant disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components can generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

A polynucleotide encoding an antigen binding protein, e.g., a CAR, can exist in an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell). In some embodiments, a polynucleotide or vector can include a nucleic acid sequence encoding ribosomal skip sequences such as, for example without limitation, a sequence encoding a 2A peptide. 2A peptides, which were identified in the Aphthovirus subgroup of picornaviruses, cause a ribosomal "skip" from one codon to the next without the formation of a peptide bond between the two amino acids encoded by the codons (see, e.g., Donnelly and Elliott 2001; Atkins, Wills et al. 2007; Doronina, Wu et al. 2008). By "codon" is meant three nucleotides on an mRNA (or on the sense strand of a DNA molecule) that are translated by a ribosome into one amino acid residue. Thus, two polypeptides can be synthesized from a single, contiguous open reading frame within an imRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptides into the secretory pathway of a host cell, in some embodiments, a secretory signal sequence (also known as a leader sequence, preprosequence or pre-sequence) is provided in a polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences can be positioned elsewhere in the nucleic acid sequence of interest (see, e.g., Welch et al., U.S. Pat. No. 5,037,743; Holland et al., U.S. Pat. No. 5,143,830). Those skilled in the art will recognize that, in view of the degeneracy of the genetic code, considerable sequence variation is possible among these polynucleotide molecules. In some embodiments, nucleic acid sequences of the instant disclosure are codon-optimized for expression in mammalian cells, preferably for expression in human cells. Codon-optimization refers to the exchange in a sequence of interest of codons that are generally rare in highly expressed genes of a given species for codons that are generally frequent in highly expressed genes of such species, such codons encoding the same amino acids as the codons that are being exchanged.

Methods of preparing immune cells for use in immuno-therapy are provided herein. In some embodiments, the methods comprise introducing an antigen binding protein e.g. a CAR into one or more immune cells, or introducing a polynucleotide encoding the antigen binding protein e.g. CAR, and expanding the cells. In some embodiments, the instant disclosure relates to a method of engineering an immune cell comprising: providing an immune cell and expressing at the surface of the cell at least one antigen binding protein e.g. a CAR. In some embodiments, the method comprises: transfecting the cell with at least one polynucleotide encoding an antigen binding protein e.g. a CAR, and expressing the at least one polynucleotide in the cell.

In some embodiments, the polynucleotides encoding the antigen binding protein e.g. a CAR are present in one or more expression vectors for stable expression in the cells. In some embodiments, the polynucleotides are present in viral vectors for stable expression in the cells. In some embodiments, the viral vectors can be for example, lentiviral vectors or adenoviral vectors.

In some embodiments, polynucleotides encoding polypeptides according to the present disclosure can be mRNA which is introduced directly into the cells, for example by electroporation. In some embodiments, CytoPulse technology can be used to transiently permeabilize living cells for delivery of material into the cells. Parameters can be modified in order to determine conditions for high transfection efficiency with minimal mortality.

Also provided herein are methods of transfecting an immune cell e.g. a T cell. In general, any conventional method known to the person of ordinary skill in the art can be used, such as introducing any of RNA, DNA or protein into a cell by means of electroporation. See, e.g., Luft and Ketteler, J. Biomolec Screening 20(8): 932 (2015) (DOI: 10.1177/1087057115579638). In some embodiments, the method comprises: contacting a T cell with RNA and applying to the T cell an agile pulse sequence consisting of: (a) an electrical pulse with a voltage range from about 2250 to 3000 V per centimeter; (b) a pulse width of 0.1 ms; (c) a pulse interval of about 0.2 to 10 ms between the electrical pulses of step (a) and (b); (d) an electrical pulse with a voltage range from about 2250 to 3000 V per centimeter with a pulse width of about 100 ms and a pulse interval of about 100 ms between the electrical pulse of step (b) and the first electrical pulse of step (c); and (e) four electrical pulses with a voltage of about 325 V with a pulse width of about 0.2 ms and a pulse interval of 2 ms between each of 4 electrical pulses. In some embodiments, a method of transfecting a T cell comprises contacting said T cell with RNA and applying to the T cell an agile pulse sequence comprising: (a) an electrical pulse with a voltage of about 1600, 2250, 2300, 2350, 2400, 2450, 2500, 2550, 2400, 2450, 2500, 2600, 2700, 2800, 2900 or 3000V per centimeter; (b) a pulse width of 0.1 ms; (c) and a pulse interval of about 0.2, 0.5, 1, 2, 3, 4, 5, 6, 7, 8, 9 or 10 ms between the electrical pulses of step (a) and (b); (d) one electrical pulse with a voltage range from about 2250 to 3000 V per centimeter, e.g. of 2250, 2300, 2350, 2400, 2450, 2500, 2550, 2400, 2450, 2500, 2600, 2700, 2800, 2900 or 3000V per centimeter with a pulse width of 100 ms and a pulse interval of 100 ms between the electrical pulse of step (b) and the first electrical pulse of step (c); and (e) 4 electrical pulses with a voltage of about 325 V with a pulse width of about 0.2 ms and a pulse interval of about 2 ms between each of 4 electrical pulses. Any values included in the value range described above are disclosed in the present application. Electroporation medium can be any suitable medium known in the art. In some embodiments, the electroporation medium has conductivity in a range spanning about 0.01 to about 1.0 milliSiemens.

In some embodiments, the method can further comprise a step of genetically engineering a cell by inactivating or reducing the expression level of at least one gene expressing, for example without limitation, TAP2, NLRC5, β2m, CIITA, RFX5, RFXAP and RFXANK, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is one or more of the genes selected from the group consisting of, for example without limitation, NLRC5, TAP2, TCRa, TCRβ, β2-microglobulin ("β2m" or b2m), CD52, CIITA, RFX5, RFXAP, RFXANK, GR, deoxycytidine kinase (DCK), PD-1, and CTLA-4. In some embodiments the method comprises inactivating or reducing the expression level of one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease or TALEN®), a megaTAL nuclease or a Cas9 endonuclease.

In another aspect, a step of genetically modifying or engineering immune cells e.g. T cells can comprise: modifying immune cells e.g. T cells by inactivating at least one gene expressing a target for an immunosuppressive agent, and; expanding the cells, optionally in the presence of the immunosuppressive agent. An immunosuppressive agent is an agent that suppresses immune function by one of several mechanisms of action. An immunosuppressive agent can diminish the extent and/or voracity of an immune response. Non-limiting examples of immunosuppressive agents include calcineurin inhibitors, targets of rapamycin, interleukin-2 α-chain blockers, inhibitors of inosine monophosphate dehydrogenase, inhibitors of dihydrofolic acid reductase, corticosteroids, and immunosuppressive antimetabolites. Some cytotoxic immunosuppressants act by inhibiting DNA synthesis. Others can act through activation of T cells or by inhibiting the activation of helper cells. The methods according to the instant disclosure allow conferring immunosuppressive resistance to e.g. T cells for immunotherapy by inactivating the target of the immunosuppressive agent in the T cells. As non-limiting examples, targets for an immunosuppressive agent can be a receptor for an immunosuppressive agent such as for example without limitation CD52, glucocorticoid receptor (GR), FKBP family gene members, and cyclophilin family gene members.

Compositions and methods for expressing an antigen binding protein e.g. a CAR in conjunction with downregulation of functional expression of one or more of TAP2, NLRC5, β2m, TRAC, RFX5, RFXAP, CIITA and RFXANK are provided herein. Also provided are uses of such compositions and methods for improving the functional activities of immune cells e.g. T cells, such as CAR-T cells. The methods and compositions provided herein are useful for improving in vivo persistence and therapeutic efficacy of engineered immune cells e.g. engineered T cells such as CAR-T cells.

Engineered immune cells e.g. engineered T cells provided herein express an antigen binding protein e.g. a chimeric antigen receptor (CAR) and express any one or more of TAP2, NLRC5, β2m, TRAC, CIITA, RFX5, RFXAP and RFXANK at a level not greater than 75%, not greater than 50%, not greater than 25%, or not greater than 10% of the expression level in non-engineered immune cells. Advantageously, the engineered immune cells provided herein exhibit improved in vivo persistence and/or increased resistance to rejection by the recipient's immune system, relative to non-engineered cells.

In some embodiments, an immune cell e.g. a T cell provided herein further is modified e.g. genetically modified to express one or more of TAP2, NLRC5, β2m, TRAC, CIITA, RFX5, RFXAP and RFXANK at a reduced level relative to a comparable cell that has not been so modified. For example, the immune cells can be genetically modified to knock out all or part of one or more of the TAP2, NLRC5, β2m, TRAC, CIITA, RFX5, RFXAP and RFXANK loci such that the corresponding functional protein is not expressed at the cell's surface, e.g. by deleting genomic DNA that comprises part or all of the entire coding sequence of the locus and/or the genomic DNA that comprises the locus's transcriptional control and/or promoter and/or activation elements and/or by introducing an insertion, deletion or substitution mutation that prevents production of a functional protein.

In some embodiments, functional expression levels of one or more of TAP2, NLRC5, β2m, TRAC, CIITA, RFX5, RFXAP and RFXANK in immune cells e.g. T cells of the instant disclosure can be decreased by at least about 30%, 35%, 40%, 45%, 50%, 55%, 60%, 65%, 70%, 75%, 80%, 85%, 90%, 95%, 99%, or 100% relative to functional expression levels in comparable cells that have not been engineered to reduce the corresponding expression level.

One or more antigen binding proteins e.g. one or more CARs can be synthesized in situ in the cell after introduction of a polynucleotide construct encoding the proteins into the cell. Alternatively, an antigen binding protein e.g. CAR can be produced outside of cells, and then introduced into cells. Methods for introducing a polynucleotide construct into cells are known in the art. In some embodiments, stable transformation methods can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides can be introduced into a cell by any suitable means such as for example, recombinant viral vectors (e.g. retroviruses, including lentiviruses, adenoviruses), liposomes, and the like. Transient transformation methods include, for example without limitation, microinjection, electroporation or particle bombardment. Polynucleotides can be included in vectors, such as for example plasmid vectors or viral vectors.

In some embodiments, an engineered immune cell e.g. a T cell of the instant disclosure can comprise at least one antigen binding protein e.g. CAR. The engineered immune cell e.g. T cell is further modified e.g. genetically engineered to express a reduced level of one or more of TAP2, NLRC5, β2m, TRAC, RFX5, RFXAP, CIITA and RFXANK. In some embodiments, the engineered immune cell e.g. an engineered T cell can comprise two or more different antigen binding proteins, e.g. two or more different CARs, each CAR comprising different extracellular ligand-binding domains.

In some embodiments of an engineered immune cell e.g. T cell provided herein, a CAR that the cell expresses can comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain CARs and polypeptides are also provided herein. In some embodiments, the multichain CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR.

The extracellular ligand-binding domain specifically binds to a target of interest. In some embodiments, the target of interest can be any molecule of interest, including, for example, without limitation, BCMA, EGFRvIII, Flt-3, WT-1, CD20, CD23, CD30, CD38, CD70, CD33, CD133, WT1, TSPAN10, MHC-PRAME, Liv1, ADAM10, CHRNA2, LeY, NKG2D, CS1, CD44v6, ROR1, CD19, Claudin-18.2 (Claudin-18A2, or Claudin18 isoform 2), DLL3 (Delta-like protein 3, *Drosophila* Delta homolog 3, Delta3), Muc17, Muc3, Muc3, Muc16, FAP alpha (Fibroblast Activation Protein alpha), Ly6G6D (Lymphocyte antigen 6 complex locus protein G6d, c6orf23, G6D, MEGT1, NG25), RNF43 (E3 ubiquitin-protein ligase RNF43, RING finger protein 43), specifically including the human form of any of the listed exemplary targets.

In some embodiments, the antigen binding domain specifically binds BCMA, MUC16 (also known as CA125), EGFR, EGFRvIII, MUC1, Flt-3, WT-1, CD20, CD23, CD30, CD38, CD70, CD33, CD133, MHC-WT1, TSPAN10, MHC-PRAME, MHC-NY-ESO1, HER2 (ERBB2), CAIX (Carbonic anhydrase IX), LIV1, ADAM10, CHRNA2, LeY, NKG2D, CS1, CD44v6, ROR1, CD19, Claudin-18.2 (Claudin-18A2, or Claudin18 isoform 2), PSCA, DLL3 (Delta-like protein 3, *Drosophila* Delta homolog 3, Delta3), Mud 7 (Mucin17, Muc3, Muc3), FAP alpha (Fibroblast Activation Protein alpha), Ly6G6D (Lymphocyte antigen 6 complex locus protein G6d, c6orf23, G6D, MEGT1, NG25), PSCA, MSLN, or RNF43 (E3 ubiquitin-protein ligase RNF43, RING finger protein 43). CARs and/or antibodies that target the antigens are disclosed, for example, in the following: BCMA— WO201616630, WO2020150339, WO2019196713, WO2016014565, WO2017025038; MUC16: U.S. Pat. No. 9,169,328, WO2016149368, WO2020023888; EGFRvIII: WO2017125830, WO2016016341; Flt3: WO2018222935, WO2020010284, WO2017173410; CD20: WO2018145649, WO2020010235, WO2020123691; CD38: WO2017025323; CD70: WO2019152742, WO2018152181; CD33: WO2016014576; CD133:

WO2018072025; CS1: WO2019030240; ROR1: WO2016115559; CD19: WO2002077029, U.S. Pat. No. 11,077,144; Claudin: WO2018006882, WO2021008463; DLL3: WO2020180591; WT1: US20160152725A1, U.S. Pat. No. 7,622,119B2; CD23: U.S. Pat. No. 6,011,138A, CN1568198A; CD30: U.S. Ser. No. 10/815,301B2, U.S. Ser. No. 10/808,035B2; PRAME: US20180148503A1, WO2020186204A1; LIV1: US20200231699A1; NKG2D: WO2021179353A1, US20210269501A1; FAP Alpha: US20200246383A1, US20210115102A1; PSMA: US20210277141A1, WO2020108646A1; MSLN: CN109680002A, CN109628492A.

In some embodiments, the extracellular ligand-binding domain comprises an scFv comprising the light chain variable (VL) region and the heavy chain variable (VH) region of a target antigen specific monoclonal antibody joined by a flexible linker. Single chain variable region fragments are made by linking light and/or heavy chain variable regions by using a short linking peptide (Bird et al., Science 242:423-426, 1988). An44 example of a linking peptide is the GS linker having the amino acid sequence (GGGGS)3 (SEQ ID NO: 22), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid or other vector containing a polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The intracellular signaling domain of a CAR according to the instant disclosure is responsible for intracellular signaling following the binding of extracellular ligand-binding domain to the target resulting in the activation of the immune cell and immune response. The intracellular signaling domain has the ability to activate at least one of the normal effector functions of the immune cell in which the CAR is expressed. For example, the effector function of a T cell can be a cytolytic activity or helper activity including the secretion of cytokines.

In some embodiments, an intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs or ITAMs. ITAMs are well defined signaling motifs found in the intracytoplasmic tail of a variety of receptors that serve as binding sites for syk/zap70 class tyrosine kinases. Examples of ITAM used in the instant disclosure can include as non-limiting examples those derived from TCRζ, FcRγ, FcRβ, FcRε, CD3γ, CD3δ, CD3ε, CD5, CD22, CD79a, CD79b and CD66d. In some embodiments, the intracellular signaling domain of the CAR can comprise the CD3ζ signaling domain. In some embodiments the intracellular signaling domain of the CAR of the instant disclosure comprises a domain of a co-stimulatory molecule.

In some embodiments, the intracellular signaling domain of a CAR of the instant disclosure comprises a part of a co-stimulatory molecule selected from the group consisting of fragment of 4-1BB (GenBank: AAA53133) and CD28 (NP_006130 and isoforms thereof).

CARs are expressed on the surface membrane of the cell. Thus, the CAR can comprise a transmembrane domain. Suitable transmembrane domains for a CAR disclosed herein have the ability to (a) be expressed at the surface of a cell, for example an immune cell such as, for example without limitation, lymphocyte cells (e.g. T cells) or Natural killer (NK) cells, and (b) interact with the ligand-binding domain and intracellular signaling domain for directing a cellular response of an immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a domain of the T cell receptor such as α, β, γ or δ, polypeptide constituting CD3 complex, IL-2 receptor e.g. p55 (α chain), p75 (β chain or γ chain), subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1). The transmembrane domain can further comprise a stalk domain between the extracellular ligand-binding domain and said transmembrane domain. A stalk domain can comprise up to 300 amino acids, for example, from 10 to 100 amino acids or 25 to 50 amino acids. The stalk region can be derived from all or part of naturally occurring molecules, such as from all or part of the extracellular region of CD8, CD4, or CD28, or from all or part of an antibody constant region. Alternatively, the stalk domain can be a synthetic sequence that corresponds to a naturally occurring stalk sequence or can be an entirely synthetic stalk sequence. In some embodiments said stalk domain is a part of human CD8α chain (e.g., NP_001139345 and isoforms thereof). In another particular embodiment, the transmembrane domain comprises a part of the human CD8α chain. In some embodiments, CARs disclosed herein can comprise an extracellular ligand-binding domain that specifically binds BCMA, CD8α human stalk and transmembrane domains, the CD3ζ signaling domain, and 4-1BB signaling domain. In some embodiments, a CAR can be introduced into an immune cell as a transgene via a vector e.g. a plasmid vector. In some embodiments, the vector e.g. plasmid vector can also contain, for example, a selection marker which provides for identification and/or selection of cells which received the vector.

CAR polypeptides can be synthesized in situ in the cell after introduction of polynucleotides encoding the CAR polypeptides into the cell. Alternatively, CAR polypeptides can be produced outside of cells, and then introduced into cells. Methods for introducing a polynucleotide construct into cells are known in the art. In some embodiments, stable transformation methods can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides can be introduced into a cell by any suitable means such as for example, recombinant viral vectors (e.g. retroviruses (e.g. lentiviruses), adenoviruses), liposomes, and the like. Transient transformation methods include, for example without limitation, microinjection, electroporation or particle bombardment. Polynucleotides can be included in vectors, such as for example plasmid vectors or viral vectors.

Also provided herein are immune cells e.g. T cells such as isolated T cells obtained according to any one of the methods described herein. Any immune cell capable of expressing heterologous DNAs can be used for the purpose of expressing the antigen binding protein e.g. CAR of interest and further for engineering to express a reduced level of one or more of TAP2, NLRC5, β2m, TRAC, RFX5, RFXAP, CIITA and RFXANK. In some embodiments, the immune cell is a T cell. In some embodiments, an immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. The isolated cell can also be a dendritic cell, killer dendritic cell, a mast cell, a NK– cell, a B-cell or a T cell selected from the group consisting of inflammatory T-lymphocytes, cytotoxic T-lymphocytes, regulatory T-lymphocytes or helper T-lymphocytes. In some embodiments, the cell can be derived from the group consisting of CD4+T-lymphocytes and CD8+T-lymphocytes. In some embodiments, the immune cells e.g. T cells such as isolated T cells are further modified e.g. genetically engineered by methods described herein (e.g. known gene editing techniques that employ, for example, TALENs, CRISPR/Cas9, or megaTAL nucleases to partially or wholly delete or disrupt one or more of the TAP2, NLRC5, β2m, TRAC, RFX5, RFXAP, CIITA and RFXANK gene loci) so that they express a reduced level of the corresponding protein relative to comparable cells not engineered to express a reduced or altered level of the corresponding protein.

The engineered immune cells provided herein can comprise one or more mimotope sequences that enable sorting of cells to enrich a population for cells engineered as described herein, e.g. cells that express the antigen binding protein, and/or that provide a safety switch mechanism to inactivate the immune cell after the cells have been administered to the patient or recipient, e.g. to limit adverse effects. Such mimotope sequences and their application in cell sorting and as safety switches are known in the art and described, for example, in US2018/0002435, which is incorporated herein by reference in its entirety.

Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, can be used. In some embodiments, cells can be derived from a healthy donor, from a subject diagnosed with cancer or from a subject diagnosed with an infection. In some embodiments, cells can be part of a mixed population of cells which present different phenotypic characteristics.

Also provided herein are cell lines obtained from a modified e.g. transformed or engineered immune cell e.g. engineered T cell according to any of the methods described herein. In some embodiments, an engineered immune cell e.g. engineered T cell according to the instant disclosure comprises a polynucleotide encoding an antigen binding protein e.g. a CAR and further modified or engineered e.g. genetically modified to express e.g. functionally express one or more of TAP2, NLRC5, β2m, TRAC, RFX5, RFXAP, CIITA and RFXANK at a reduced level.

The immune cells, e.g. T cells of the instant disclosure, can be activated and expanded, either prior to or after modification of the cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. Immune cells e.g. T cells can be expanded in vitro or in vivo. Generally, the immune cells of the instant disclosure can be expanded, for example, by contact with an agent that stimulates a CD3 TCR complex and a co-stimulatory molecule on the surface of the immune cells to create an activation signal for the cell. For example, chemicals such as calcium ionophore A23187, phorbol 12-myristate 13-acetate (PMA), or mitogenic lectins like phytohemagglutinin (PHA) can be used to create an activation signal for the immune cell, e.g., a T cell.

In some embodiments, T cell populations can be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate medium (e.g., Minimal Essential Media, RPMI Media 1640 or, X-VIVO™ 5, (Lonza)) that can contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, a TGFβ, and TNF, or any other additives for the growth of cells known to the skilled artisan. Other additives for the growth of cells include, but are not limited to, surfactant, Plasmanate®, and reducing agents such as N-acetyl-cysteine and 2-mercaptoethanol. Media can include RPMI 1640 (as noted herein), AIM V, DMEM, MEM, α-MEM, F-12, X-VIVO™ 10, X-VIVO™ 15 and X-VIVO™ 20, OpTmizer™, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). Immune cells e.g. T cells that have been exposed to varied stimulation times can exhibit different characteristics.

In some embodiments, the cells of the instant disclosure can be expanded by co-culturing with tissue or cells. The cells can also be expanded in vivo, for example in the subject's blood after administrating the cell into the subject.

In another aspect, the instant disclosure provides compositions (such as pharmaceutical compositions) comprising any of the cells of the instant disclosure. In some embodiments, the composition comprises a T cell comprising a polynucleotide encoding an antigen binding protein e.g. a CAR. The cell is further engineered to express a reduced level of one or more of TAP2, NLRC5, β2m, TRAC, RFX5, RFXAP, CIITA and RFXANK. The compositions comprise, for example, an engineered immune cell e.g. T cell of the instant disclosure, e.g. an immune cell that expresses an antigen binding protein e.g. a CAR and functionally expresses one or more of TAP2, NLRC5, β2m, TRAC, RFX5, RFXAP, CIITA and RFXANK at a reduced level relative to comparable cells not engineered to functionally express a reduced or altered level of the corresponding protein, or comprise a population of cells that comprises an engineered immune cell e.g. T cell of the instant disclosure, and one or more pharmaceutically acceptable carriers or excipients.

In some embodiments, primary cells isolated from a donor are engineered as described herein to provide a population of cells of which a subpopulation (e.g., a proportion less than 100%, such as 10%, 20%, 30%, 40%, 50%, 60%, 70% 80% or 90%) of the resulting cells comprise all of the desired modifications. Such a resulting population, comprising a mixture of cells that comprise all of the modifications and cells that do not, can be used in the methods of treatment of the instant disclosure and to prepare the compositions of the instant disclosure. Alternatively, this population of cells (the "starting population") can be manipulated by known methods e.g. cell sorting and/or expansion of cells that have the desired modifications, to provide a population of cells that is enriched for those cells comprising one or more of the desired modifications (e.g. enriched for cells that express the desired antigen binding protein and/or enriched for cells that express one or more of TAP2, NLRC5, β2m, TRAC, RFX5, RFXAP, CIITA and RFXANK at a reduced level relative to comparable cells not engineered with respect to expression level of the corresponding protein), that is, that comprises a higher percentage of such modified or engineered cells than did the starting population. The population enriched for the modified cells can then be used in the methods of treatment of the instant disclosure and to prepare the compositions of the instant disclosure, for example. In some embodiments, the enriched population of cells contains, or contains at least, for example, 20%, 30%, 40%, 50%, 60%, 70%, 80%, 90%, 95%, or 99% cells that have one or more of the modifications. In other embodiments, the proportion of cells of the enriched population of cells that comprise one or more of the modifications is at least 30% higher than the proportion of cells of the starting population of cells that comprise the desired modifications.

Methods of Treating

Immune cells, e.g. T cells obtained by the methods described above, or cell lines derived from such immune cells or T cells, can be used as a medicament. In some embodiments, such a medicament can be used for treating a disorder such as for example a viral disease, a bacterial disease, a cancer, an inflammatory disease, an immune disease, or an aging-associated disease. In some embodiments, the cancer can be selected from the group consisting of gastric cancer, sarcoma, lymphoma (including Non-Hodgkin's lymphoma), leukemia, head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colon cancer, oral cancer, skin cancer, and melanoma. In some embodiments, the subject is a previously treated adult subject with locally advanced or metastatic melanoma, squamous cell head and neck cancer (SCHNC), ovarian carcinoma, sarcoma, or relapsed or refractory classic Hodgkin's Lymphoma (cHL).

In some embodiments, immune cells e.g., T cells according to the instant disclosure, or cell line derived from the immune cells e.g., engineered T cells, can be used in the manufacture of a medicament for treatment of a disorder in a subject in need thereof. In some embodiments, the disorder can be, for example, a cancer, an autoimmune disorder, or an infection.

Also provided herein are methods for treating subjects. In some embodiments the method comprises administering or providing an immune cell e.g., an engineered T cell of the instant disclosure to a subject in need thereof. In some embodiments, the method comprises a step of administering the immune cells e.g., T cells of the instant disclosure, to a subject in need thereof.

In some embodiments, immune cells e.g., engineered T cells of the instant disclosure can undergo robust in vivo cell expansion and can persist for an extended amount of time. Methods of treatment of the instant disclosure can be ameliorating, curative or prophylactic. The method of the instant disclosure can be either part of an autologous immunotherapy or part of an allogenic immunotherapy treatment. The instant disclosure is particularly suitable for allogeneic immunotherapy. Immune cells e.g., engineered T cells provided by a donor, can be transformed into non-alloreactive cells using standard protocols and reproduced as needed, thereby producing e.g. CAR-T cells which can be administered to one or several subjects. Such CAR-T cell therapy can be made available as an allogeneic ALLO CAR T™ therapeutic product.

In another aspect, the instant disclosure provides a method of inhibiting tumor growth or progression in a subject who has a tumor, comprising administering to the subject an effective amount of engineered immune cells e.g. engineered T cells as described herein. In another aspect, the present disclosure provides a method of inhibiting or preventing metastasis of cancer cells in a subject, comprising administering to the subject in need thereof an effective amount of engineered immune cells e.g. engineered T cells as described herein. In another aspect, the instant disclosure provides a method of inducing tumor regression in a subject who has a tumor, comprising administering to the subject an effective amount of engineered immune cells, e.g., engineered T cells as described herein.

In some embodiments, the immune cells, e.g., T cells provided herein can be administered parenterally to a subject. In some embodiments, the subject is a human.

In some embodiments, the method can further comprise administering an effective amount of a second therapeutic agent. In some embodiments, the second therapeutic agent is, for example, crizotinib, palbociclib, an anti-CTLA4 antibody, an anti-4-1 BB antibody, a PD-1 antibody, or a PD-L1 antibody.

Also provided is the use of any of the immune cells e.g. T cells provided herein in the manufacture of a medicament for the treatment of cancer or for inhibiting tumor growth or progression in a subject in need thereof.

In certain embodiments, the functional expression level of one or more of TAP2, NLRC5, $\beta$2m, TRAC, RFX5, RFXAP, CIITA and RFXANK, or the functional expression level of any other gene that is knocked down or knocked out according to the present disclosure, in an engineered immune cell of the instant disclosure is decreased by or by at least about 25%, 30%, 35%, 40%, 45%, 50%, 55%, 60%, 65%, 70%, 75%, 80%, 85%, 90%, 95%, 99%, or 100% relative to the corresponding expression level in a comparable but not so genetically-modified engineered immune cell. Expression levels can be determined by any known method, such as FACS or MACs. In some embodiments, the engineered immune cell disclosed herein functionally expresses any one or more of TAP2, NLRC5, $\beta$2m, TRAC, CIITA, RFX5, RFXAP and RFXANK, or any other gene that is knocked down or knocked out according to the present disclosure, at a level not greater than 75%, not greater than 50%, not greater than 25%, not greater than 10% or at a level of 0% of the expression level in non-engineered immune cells that otherwise are the same as the engineered immune cells, e.g. comprise the same components as the engineered immune cells. In some embodiments, both alleles of one gene are knocked out, so that gene's expression level in the engineered immune cell disclosed herein is 0% of that of a corresponding non-engineered cell. In some embodiments, one of the two alleles of a gene is knocked out, so that gene's expression level in the engineered immune cell disclosed herein is 50% or about 50% (e.g. if a compensatory mechanism causes greater than normal expression of the remaining allele) of that of a corresponding non-engineered cell. Intermediate levels of expression can be observed if, for example, expression is reduced by some means other than knock-out, as described herein.

In some embodiments, the expression level of one or more of TAP2, NLRC5, $\beta$2m, TRAC, RFX5, RFXAP, CIITA and RFXANK, or of any other gene the expression level of which is manipulated according to the present disclosure, in the engineered cells of the present disclosure can be measured directly by assaying the cells for gene products and their properties using standard techniques known to those of skill in the art (e.g. RT-qPCR, nucleic acid sequencing, antibody staining, or some combination of techniques). In some embodiments, the functional expression level of one or more of TAP2, NLRC5, $\beta$2m, TRAC, CIITA, RFX5, RFXAP and RFXANK is measured by determining the surface expression level of one or more HLA proteins, such as an HLA-A or HLA-B protein, or of beta2 microglobulin (B2M), or of both B2M and one or more HLA proteins on the surface of the engineered immune cell by standard techniques known in the art, e.g. flow cytometry. These measurements can be compared to corresponding measurements made on comparable cells that have not been engineered to reduce the corresponding functional expression level. In a population of cells that comprises an engineered cell e.g. engineered immune cell of the invention, a pooled sample of the material being measured, e.g. RNA or protein or cells, will reflect the fact that some of the cells do not express the gene of interest, having had both alleles knocked out, for example, some of the cells express the gene of interest at 50% or about 50%, having had only one allele knocked out, and, if the population comprises non-engineered cells, that some of the cells express a normal level of the gene of interest.

The functional expression level of one or more of TAP2, NLRC5, β2m, TRAC, CIITA, RFX5, RFXAP and RFXANK expression in engineered immune cells of the present disclosure can also be assayed, for example, by measuring the degree to which the engineered immune cells survive in the presence of effector cells e.g. T cells or NK cells, in comparison to the degree to which non-engineered, but otherwise comparable e.g. identical, immune cells survive under the same conditions. See, e.g., FIGS. 6A-6C and Example 1.

In some embodiments, administering an engineered immune cell e.g. engineered T cell as disclosed herein, or administering a population of cells comprising such engineered immune cells e.g. engineered T cells, reduces host rejection of the administered cell or population of cells relative to a comparable but non-engineered cell or comparable population that does not comprise such engineered cells. In some embodiments, administering an engineered immune cell, e.g., engineered T cell of the instant disclosure, comprising an antigen binding protein e.g. a CAR and in which the expression level e.g. functional expression level of one or more of TAP2, NLRC5, β2m, TRAC, RFX5, RFXAP, CIITA and RFXANK is reduced, or administering a population of cells comprising such engineered immune cells, e.g., engineered T cells, reduces host rejection of the administered cell or population of cells relative to a comparable but non-engineered cell or population that does not comprise such engineered cells. For example, such administration reduces host rejection by between 1% and 99%, e.g. between 5% and 95%, between 10% and 90%, between 50% and 90%, e.g. by 10%, 20%, 30%, 40%, 50%, 60%, 70%, 80%, or 90% as compared to host rejection of cells that are the same but which are not engineered to express the corresponding protein at a reduced level. In some embodiments, host rejection is reduced by over 90%.

In some embodiments, administering an immune cell e.g. T cell of the instant disclosure comprising an antigen binding protein e.g. a CAR and in which the functional expression level of one or more of TAP2, NLRC5, β2m, TRAC, RFX5, RFXAP, CIITA and RFXANK is reduced, or administering a population of cells comprising such immune cells e.g. T cells, enhances or improves the persistence and/or increases the persistence of the cells as compared to the persistence of cells that are the same but which are not engineered to express a reduced level of the corresponding protein. In some embodiments, persistence is increased by, for example, between 1 and 7 days, by between 1 and 12 weeks (e.g. between 1 and 4 weeks, 4 and 8 weeks, or 8 and 12 weeks), or by between 1 and 12 months, or by a specific length of time that falls within these ranges. In some embodiments, the difference in persistence is measured by comparing the half-life of the administered cells in the population or composition, wherein, for example, the half-life is increased by, for example, between 1 and 7 days, by between 1 and 12 weeks (e.g. between 1 and 4 weeks, 4 and 8 weeks, or 8 and 12 weeks), or by between 1 and 12 months, or by a specific length of time that falls within these ranges. In some embodiments, the difference in persistence is measured by comparing the length of time that the administered cells can be detected after administration. In some embodiments, the improvement in persistence is measured in vitro by comparing the survival of engineered and non-engineered cells in the presence of, for example, immune cells such as T cells or NK cells, e.g. at about 72 hours, 5 days, 7 days or 13 days after mixing. In some embodiments, in such an in vitro assay, between about 1.5 and 10 times as many engineered cells survive as do cells that are not engineered at the time of measurement.

In some embodiments, reduction in host rejection and/or increases in persistence of administered cells as disclosed herein are determined by any of a variety of techniques known to the person of ordinary skill in the art. In some embodiments, any one or a combination of the following is use: flow cytometry, PCR, e.g., quantitative PCR, and ex vivo coincubation with patient tumor material or with a model tumor cell line expressing the antigen targeted by the CAR-T cell. In some embodiments, qPCR is used to assess the number of CART cells that have and do not have the knock-out of interest in order to determine the extent to which the knock-out provides a survival advantage.

In some embodiments, the treatment can be in combination with one or more therapies against cancer selected from the group of antibodies therapy, chemotherapy, cytokines therapy, dendritic cell therapy, gene therapy, hormone therapy, laser light therapy and radiation therapy.

In some embodiments, treatment can be administered to subjects undergoing an immunosuppressive treatment. Indeed, the instant disclosure can rely on cells or a population of cells which have been made resistant to at least one immunosuppressive agent due to the inactivation of a gene encoding a receptor for such immunosuppressive agent. In this aspect, the immunosuppressive treatment can help the selection and expansion of the T cells according to the instant disclosure within the subject.

The administration of the cells or population of cells according to the instant disclosure can be carried out in any convenient manner, including by aerosol inhalation, injection, ingestion, transfusion, implantation or transplantation. The compositions described herein can be administered to a subject subcutaneously, intradermally, intratumorally, intranodally, intramedullary, intramuscularly, by intravenous or intralymphatic injection, or intraperitoneally. In one embodiment, the cell compositions of the instant disclosure are administered by intravenous injection.

In some embodiments, the administration of the cells or population of cells according to the instant disclosure can comprise administration of, for example, from about $10^3$ or $10^4$ to about $10^9$ cells per kg body weight including all integer values of cell numbers within those ranges. In some embodiments the administration of the cells or population of cells can comprise administration of about $10^5$ to about $10^6$ cells per kg body weight including all integer values of cell numbers within those range, or administration of between $0.1 \times 10^6$ and $5 \times 10^6$ engineered immune cells of the invention per kg body weight, or a total of between $0.1 \times 10^8$ and $5 \times 10^8$ engineered immune cells. The cells or population of cells can be administered in one or more doses. In some embodiments, an effective amount of cells can be administered as a single dose. In some embodiments, an effective amount of cells can be administered as more than one dose over a period time. Timing of administration is within the judgment of the managing physician and depends on the clinical condition of the subject. The cells or population of cells can be obtained from any source, such as a blood bank or a donor. While individual needs vary, determination of optimal ranges of effective amounts of a given cell type for a particular disease or conditions is within the skill of the art. An effective amount means an amount which provides a therapeutic or prophylactic benefit. The dosage administered will be dependent upon the age, health and weight of the recipient, the kind of concurrent treatment, if any, the frequency of treatment and the nature of the effect desired. In some embodiments, an effective amount of cells or composition comprising those cells are administered parenterally. In some embodiments, administration can be an intravenous administration. In some embodiments, administration can be directly done by injection within a tumor.

In some embodiments of the instant disclosure, cells are administered to a subject in conjunction with (e.g., before, simultaneously or following) any number of relevant treatment modalities, including but not limited to treatment with agents such as monoclonal antibody therapy, CCR2 antagonist (e.g., INC-8761), antiviral therapy, cidofovir and interleukin-2, Cytarabine (also known as ARA-C) or nataliziimab treatment for MS subjects or efaliztimab treatment for psoriasis subjects or other treatments for PML subjects. In some embodiments, BCMA specific CAR-T cells are administered to a subject in conjunction with one or more of the following: an anti-PD-1 antibody (e.g., nivolumab, pembrolizumab), an anti-PD-L1 antibody (e.g., avelumab, atezolizumab, or durvalumab), an anti-OX40 antibody, an anti-4-1 BB antibody (e.g., Utolimumab), an anti-MCSF antibody, an anti-GITR antibody, and/or an anti-TIGIT antibody. In further embodiments, the immune cells, e.g. T cells, of the instant disclosure can be used in combination with chemotherapy, radiation, immunosuppressive agents, such as cyclosporin, azathioprine, methotrexate, mycophenolate, and FK506, antibodies, or other immunoablative agents such as CAMPATH (alemtuzumab), anti-CD3 antibodies or other antibody therapies, cytoxan, fludarabine, cyclophosphamide, cyclosporin, FK506, rapamycin, mycoplienolic acid, steroids, FR901228, cytokines, and/or irradiation. These drugs inhibit either the calcium dependent phosphatase calcineurin (cyclosporine and FK506) or inhibit the p70S6 kinase that is important for growth factor induced signaling (rapamycin) (Henderson, Naya et al. Immunology. 1991 July; 73(3): 316-321; Liu, Albers et al. Biochemistry 1992 Apr. 28; 31(16):3896-901; Bierer, Hollander et al. Curr Opin Immunol. 1993 Oct.; 5(5):763-73).

In a further embodiment, the cell compositions of the instant disclosure are administered to a subject in conjunction with (e.g., before, simultaneously or following) bone marrow transplantation, T cell ablative therapy using either chemotherapy agents such as fludarabine, external-beam radiation therapy (XRT), cyclophosphamide, or antibodies such as CAMPATH. In some embodiments, the cell compositions of the instant disclosure are administered following B-cell ablative therapy such as agents that react with CD20, e.g., Rituxan. For example, in one embodiment, subjects can undergo standard treatment with high dose chemotherapy followed by peripheral blood stem cell transplantation. In certain embodiments, following the transplant, subjects receive an infusion of expanded immune cells of the instant disclosure. In some embodiments, expanded cells are administered before or following surgery.

Kits

The instant disclosure also provides kits for use in the instant methods. Kits of the instant disclosure include one or more containers comprising a composition of the instant disclosure or an immune cell, e.g., a T cell of the instant disclosure or a population of cells comprising an immune cell, e.g., an engineered T cell of the instant disclosure. In various embodiments, the immune cell, e.g., T cell comprises one or more polynucleotide(s) encoding an antigen binding protein, e.g., a CAR as described herein, and further is engineered to express a reduced level of one or more of TAP2, NLRC5, β2m, TRAC, RFX5, RFXAP, CIITA and RFXANK as described herein. The kit further comprises instructions for use in accordance with any of the methods of the instant disclosure described herein. Generally, these instructions comprise a description of administration of the composition, immune cell, e.g., a T cell or population of cells for the above described therapeutic treatments.

The instructions relating to the use of the kit components generally include information as to dosage, dosing schedule, and route of administration for the intended treatment. The containers can be unit doses, bulk packages (e.g., multi-dose packages) or subunit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The kits of the present disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit can have a sterile access port (for example the container can be an intravenous solution bag or a vial having a stopper pierceable by a hypodermic injection needle). The container can also have a sterile access port (for example the container can be an intravenous solution bag or a vial having a stopper pierceable by a hypodermic injection needle). At least one active agent in the composition is an immune cell e.g. T cell according to the instant disclosure. The container can further comprise a second pharmaceutically active agent.

Kits can optionally provide additional components such as buffers and interpretive information. Normally, the kit comprises a container and a label or package insert(s) on or associated with the container.

Methods of Sorting and Depletion

In some embodiments, provided are methods for in vitro sorting of a population of immune cells, wherein a subset of the population of immune cells comprises immune cells engineered as described herein to express one or more of TAP2, NLRC5, β2m, TRAC, RFX5, RFXAP, CIITA and RFXANK at a reduced level and/or express an antigen binding protein, e.g., a CAR. In various embodiments the method comprises contacting the population of immune cells with a monoclonal antibody specific for an epitope (e.g., a mimotope such as those provided in US2018/0002435) unique to the engineered cell, e.g. an epitope of the antigen binding protein or a mimotope incorporated into the antigen binding protein, and selecting the immune cells that bind to the monoclonal antibody to obtain a population of cells enriched in engineered immune cells that express the antigen binding protein.

In some embodiments, the monoclonal antibody specific for the epitope is optionally conjugated to a fluorophore. In this embodiment, the step of selecting the cells that bind to the monoclonal antibody can be done by Fluorescence Activated Cell Sorting (FACS).

In some embodiments, said monoclonal antibody specific for said epitope is optionally conjugated to a magnetic particle. In this embodiment, the step of selecting the cells that bind to the monoclonal antibody can be done by Magnetic Activated Cell Sorting (MACS).

In some embodiments, the mAb used in the method for sorting immune cells expressing the antigen binding protein e.g. CAR is chosen from alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and/or ustekinumab. In some embodiments, said mAb is rituximab. In another embodiment, said mAb is QBEND-10.

In some embodiments, the population of CAR-expressing immune cells obtained when using the method for in vitro sorting CAR-expressing immune cells described above, comprises at least 70%, 75%, 80%, 85%, 90%, 95% of CAR-expressing immune cells. In some embodiments, the population of CAR-expressing immune cells obtained when using the method for in vitro sorting CAR-expressing immune cells, comprises at least 85% CAR-expressing immune cells.

In some embodiments, the population of CAR-expressing immune cells obtained when using the method for in vitro sorting CAR-expressing immune cells described above shows increased cytotoxic activity in vitro compared with the initial (non-sorted) cell population. In some embodiments, said cytotoxic activity in vitro is increased by 10%, 20%, 30% or 50%. In some embodiments, the immune cells are T-cells.

The CAR-expressing immune cells to be administered to the recipient can be enriched in vitro from the source population. Methods of expanding source populations can include selecting cells that express an antigen such as CD34 antigen, using combinations of density centrifugation, immuno-magnetic bead purification, affinity chromatography, and fluorescent activated cell sorting.

Flow cytometry can be used to quantify specific cell types within a population of cells. In general, flow cytometry is a method for quantitating components or structural features of cells primarily by optical means. Since different cell types can be distinguished by quantitating structural features, flow cytometry and cell sorting can be used to count and sort cells of different phenotypes in a mixture.

A flow cytometry analysis involves two primary steps: 1) labeling selected cell types with one or more labeled markers, and 2) determining the number of labeled cells relative to the total number of cells in the population. In some embodiments, the method of labeling cell types includes binding labeled antibodies to markers expressed by the specific cell type. The antibodies can be either directly labeled with a fluorescent compound or indirectly labeled using, for example, a fluorescent-labeled second antibody which recognizes the first antibody.

In some embodiments, the method used for sorting T cells expressing CAR is the Magnetic-Activated Cell Sorting (MACS). Magnetic-activated cell sorting (MACS) is a method for separation of various cell populations depending on their surface antigens (CD molecules) by using superparamagnetic nanoparticles and columns. MACS can be used to obtain a pure cell population. Cells in a single-cell suspension can be magnetically labeled with microbeads. The sample is applied to a column composed of ferromagnetic spheres, which are covered with a cell-friendly coating allowing fast and gentle separation of cells. The unlabeled cells pass through while the magnetically labeled cells are retained within the column. The flow-through can be collected as the unlabeled cell fraction. After a washing step, the column is removed from the separator, and the magnetically labeled cells are eluted from the column.

A detailed protocol for the purification of a specific cell population such as T-cells can be found in Basu S et al. (2010). (Basu S, Campbell H M, Dittel B N, Ray A. Purification of specific cell population by fluorescence activated cell sorting (FACS). J Vis Exp. (41): 1546).

EXAMPLES

General Methods
Generation of KO T Cells

Primary human T cells were isolated from frozen healthy donor peripheral blood mononuclear cells (PBMCs) using magnetic-activated cell sorting (MACS) negative selection (Miltenyi, human pan T cell isolation kit, Cat #130-096-535) and activated with 1:100 (v:v) T cell TransAct (Miltenyi, Cat #130-111-160)+100 IU/mL IL-2 (Miltenyi, Cat #130-097-746) in R10 (RPMI-1640+10% FBS+25 mM HEPES+Sodium Pyruvate+non-essential amino acids). After 2 days, T cells were gene edited using the Neon Transfection System (Invitrogen). Briefly, ribonucleoprotein (RNP) complexes were generated by mixing cas9 enzyme (IDT, Cat #1081059) and sgRNA at a 1:1 molar ratio for 10 min at room temperature. If two sgRNAs were used, incubation was performed with cas9 at a 0.5:0.5:1 ratio (sgRNA1: sgRNA2: cas9). Cells were pulsed at 1600 V, 10 ms width for a total of 3 times and immediately recovered in R10 media supplemented with 100 IU/mL IL-2+10 ng/mL IL-7 (Miltenyi, Cat #130-095-363). Edited T cells were incubated at 37° C., 5% $CO_2$. Fresh R10 with 100 IU/mL IL-2 was added the next day to the cells. After 5-7 days post gene editing, KO efficiency was assessed via flow cytometry. KO efficiency ranged from around 50% to as high as about 100%. KO efficiency was assessed in various ways: For TRAC, CD3/TCRab expression was assessed; for b2m, NLRC5 and RFX5, anti-b2m or an anti-HLA antibody was used. Lower editing efficiencies are acceptable because edited cells are purified as described below. KO was checked at about day 22 and was found to be relatively stable.

TRAC KO cells were purified using MACS negative selection (Stem Cell Technologies, EasySep human TCR alpha/beta depletion kit, Cat #17847) according to the manufacturer's recommendations. Purified T cells were used immediately or frozen at 5e6 cell aliquots in 90% FBS+10% DMSO.

TABLE 1

| List of sgRNA sequences | | |
| --- | --- | --- |
| SEQ ID NO: | Gene used for | sgRNA sequence (5' - 3') |
| 1 | TRAC | gcugguacacggcaggguca |
| 2 | B2M (β2M) | ucacgucauccagcagagaa |
| 3 | NLRC5 | cagcucugcaaggcucuggg |
| 4 | RFX5 | aguacauguaugccuaagg |
| 5 | CIITA | guggcacacugugagcugcc |
| 6 | RFXANK (sgRNA 1) | uuguugacgagguugucacc |
| 7 | RFXANK (sgRNA 2) | gcucgucuggcuuguugacg |

TABLE 1-continued

List of sgRNA sequences

| SEQ ID NO: | Gene used for | sgRNA sequence (5' - 3') |
|---|---|---|
| 8 | RFXANK (sgRNA 3) | gucaacaagccagacgagcg |
| 9 | RFXAP (sgRNA 1) | ucuuagcagcauggaggcgc |
| 10 | RFXAP (sgRNA 2) | cuuagcagcauggaggcgca |
| 11 | RFXAP (sgRNA 3) | cauggaggcgcaggguguag |
| 12 | TAP2 | cgcguccaccagcagcaggg |

In Vitro Allogeneic Rejection Assays

Primed T Mixed Lymphocyte Reaction (MLR) (FIGS. 7, 14A-14C, 17B)

Human PBMCs (host) were primed against irradiated PBMCs derived from donors used to make graft T cells above to promote expansion of alloreactive T cell clones. Briefly, graft PBMCs were irradiated at 30 Gy and co-cultured with host PBMCs at a 1:1 ratio in R10+20 IU/mL IL-2+10 ng/mL IL-7+10 ng/mL IL-15 (Miltenyi, Cat #130-095-765) for 4 days. Media was exchanged to R10 without cytokines and the cells were continued to culture for 3 more days. Afterwards, pan T cells were isolated using MACS negative selection (Miltenyi, human pan T cell isolation kit, Cat #130-096-535) per the manufacturer's recommendations. In a 96-well plate, 20,000 graft T cells were seeded with 20,000 primed host T cells and cultured in R10+20 IU/mL IL-2 for 2 days at 37° C., 5% $CO_2$. Survival of graft T cells was determined by flow cytometry using absolute counts by gating on live TCRαβ− CD4+CD8+.

NK MLR (FIGS. 8A-8B, 15A, 17C)

Human NK cells were isolated from freshly isolated human PBMCs via MACS purification (Miltenyi, human pan NK cell isolation kit, Cat #130-092-657). In a 96-well plate, 20,000 graft T cells were seeded with host NK cells and cultured in R10+1000 IU/mL IL-2 for 2 days at 37° C., 5% $CO_2$. Survival of graft T cells was determined by flow cytometry using absolute counts by gating on live TCRαβ− CD56− CD4+ CD8+.

PBMC MLR (FIG. 16)

In a 96-well plate, 20,000 graft T cells were seeded with 200,000 host PBMC cells (10:1 E:T ratio) and cultured in R10+20 IU/mL IL-2 for 4-13 days at 37° C., 5% $CO_2$. Cells were fed every 2-3 days with fresh R10+IL-2. Survival of graft T cells was determined by flow cytometry using absolute counts by gating on live TCRαβ− CD56− CD4+ CD8+. Expansion of effector NK cells was determined by the absolute counts of live cells gated on TCRαβ−CD56+. Expansion of effector T cells was determined by the absolute counts of live cells gated on TCRαβ+CD56− CD4+CD8+.

Figure 5:
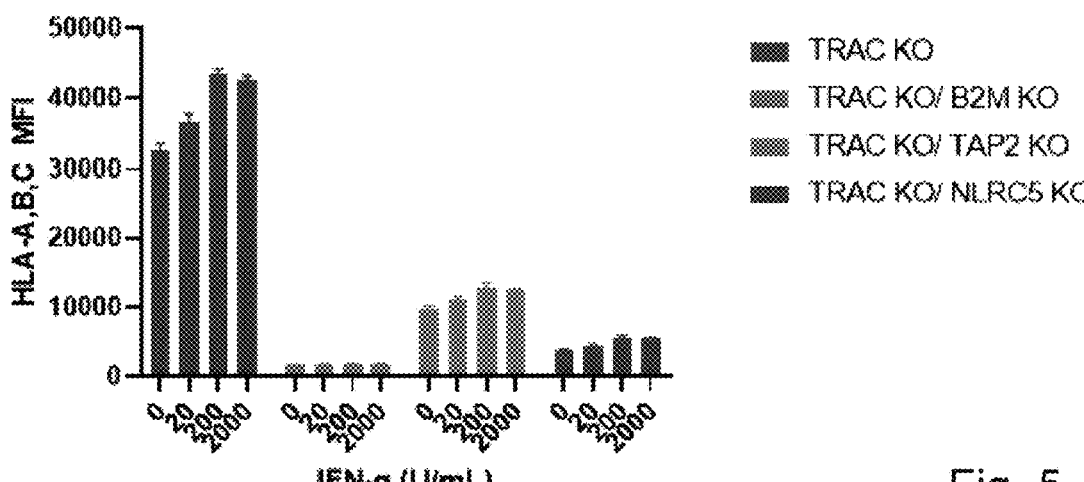
FIG. 5. Gene edited (β2m, TAP2, or NLRC5 KO) T cells exposed to IFN-γ experience a minimal change in surface MHC class I expression. Primary T cells were edited via CRISPR/Cas9 with TRAC sgRNA and either β2m, TAP2, or NLRC5 sgRNA and purified by TCR depletion. Cells were then treated with recombinant IFN-γ for 72 h and subsequently analyzed by flow cytometry for MHC class I expression using an anti-HLA-A, B, C antibody (clone W6/32). Mean+SD of MFI for 3 technical replicates are shown. KO, knockout; TRAC, T cell receptor a constant.

Example 1. TAP2 KO or NLRC5 KO Protects T Cells in an Autologous Antigen-Specific Killing Assay A. Dependence of MEW Class I Presentation NLRC5 is inducible by interferon-γ (IFN-γ) and regulates expression of components of the IFN-γ-inducible immunoproteasome (i.e. LMP2 and LMP7). IFN-γ-induced MEW class I upregulation is dependent on NLRC5, suggesting that NLRC5 KO should stably suppress MEW class I presentation in the presence or absence of IFN-γ. Indeed, when NLRC5 KO primary T cells were incubated with varying amounts of recombinant IFN-γ, there was a minimal increase in MHC class I expression relative to TRAC KO alone (FIG. 5).

B. TAP2 KO and NLRC5 KO Each Protect Against Effector Cell Killing

Figure 6A:
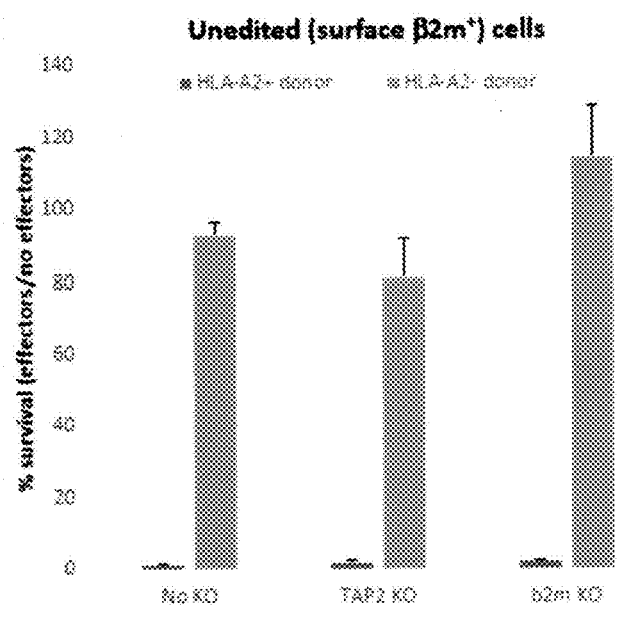
FIGS. 6A-6C. T cells lacking β2m, TAP2, or NLRC5 are protected from T cell-mediated, antigen-specific killing.

It was determined whether the modest downmodulation of MHC achieved by TAP2 KO or NLRC5 KO (see FIGS. 4A, 4B) protects T cells in an autologous antigen-specific killing assay. Primary T cells (mock product cells) were electroporated with Cas9-complexed sgRNAs to TAP2 or β2m and were transduced with the melanocyte-derived tissue differentiation antigen MART1/MelanA (BFP-P2A-MART1). In parallel, mock effector T cells from the same donors were transduced with the HLA-A2-restricted, MART1-specific T cell receptor, F5 TCR. Mock product cells and effector cells were co-incubated for 72 h and then the extent of antigen-specific killing was analyzed by quantifying the remaining BFP+(MART1-expressing) T cells via flow cytometry (see FIGS. 6A-6C). Antigen-expressing cells that retained surface β2m (beta2m) (i.e., unedited) were not killed by effector cells if they were HLA-A2− (HLA-A2-minus) (FIG. 6A, right bar of each pair), but were extirpated by effectors if they were HLA-A2+(FIG. 6A, left bar of each pair). This confirms the F5 TCR-bearing effector cells were competent to kill MART1 antigen-expressing cells subject to the restriction that HLA-A2 presents the peptide.

Figure 6B:
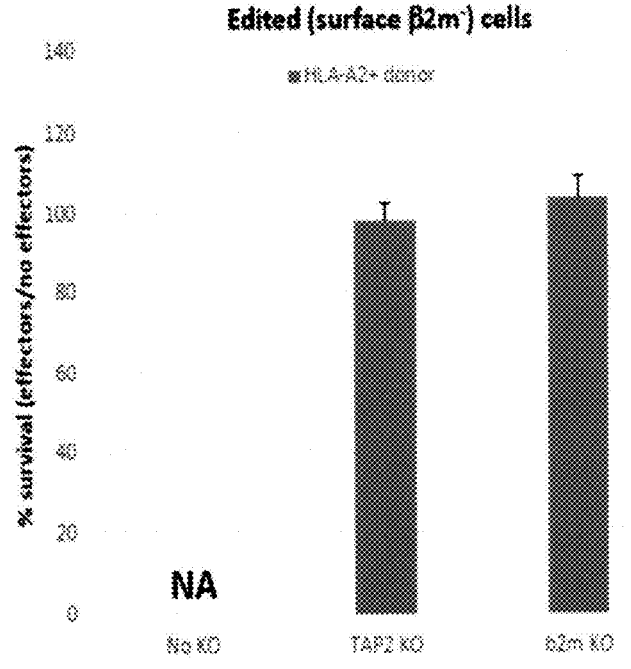
Figure 6C:
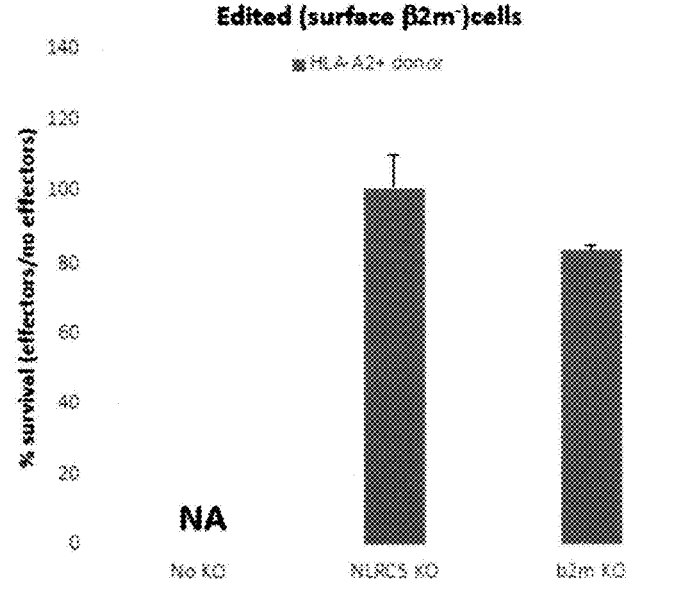

In contrast to unedited cells, antigen-expressing, HLA-A2+ cells that were edited for either TAP2 or β2m (and thus surface β2 $m^{low}$ or β2 m−, respectively) were entirely protected from killing by effector cells (FIG. 6B). Similarly, in an independent experiment, HLA-A2+ cells that were edited for either NLRC5 or β2m were also protected from killing by effector cells (FIG. 6C). Thus, knockout of β2m, TAP2, or NLRC5 protects edited T cells from T cell-mediated antigen-specific killing, but TAP2 KO and NLRC5 KO achieve this with less reduction in surface MEW than β2m KO.

Example 2. Protective Effects of NLRC5 KO in a Polymorphic Epitope Context

Figure 7:
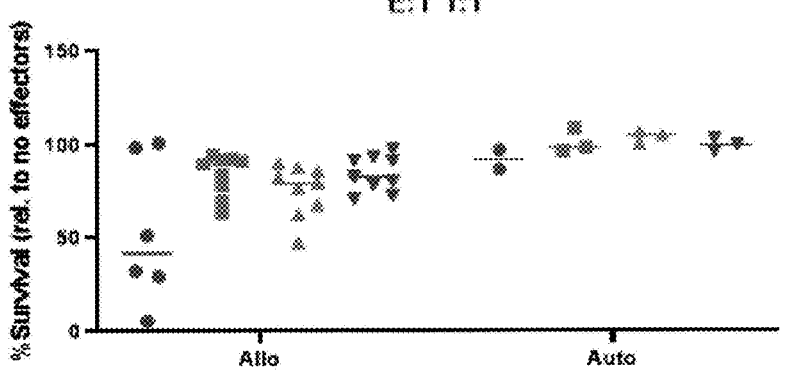
FIG. 7: b2m, TAP2, or NLRC5 KO mitigate T cell alloreactivity. Pan T cells were isolated and gene edited for TRAC KO and b2m, TAP2, or NLRC5 KO and co-incubated with effector pan T cells primed against irradiated target PBMCs for 1 week. After 48 h of co-incubation at a 1:1 E:T ratio, surviving targets were counted via flow cytometry. % Survival is calculated as the absolute counts of persisting targets with fixed volume/time acquisition and normalized to conditions without effectors. Mean±SD of 2-3 technical replicates for each effector donor are shown. Three allogeneic donors were tested.

To assess the protective effects of NLRC5 KO in a polymorphic epitope context, these targets were tested in a one-way T cell mixed lymphocyte reaction (MLR) with pan T cells freshly isolated from allogeneic donors. First, pan T cells were gene edited for TRAC KO with or without β2m, TAP2, or NLRC5 KO via CRISPR/Cas9. Targets were then purified to remove any TCR α/β expressing cells. Effector PBMCs were co-cultured with irradiated PBMCs isolated from the same target donor for 1 week to promote outgrowth and expansion of alloreactive T cells. Effector pan T cells were purified out and co-incubated with targets at 1:1 ratio for 2 days. The extent of killing was determined by analyzing the absolute number of surviving targets (FIG. 7). In the autologous setting, no killing was observed for any of the modification strategies. In the allogeneic setting, there was significant alloreactivity observed against TRAC KO modified target cells that was significantly attenuated with either β2m, TAP2, or NLRC5 KO. Thus, in a polyclonal allogeneic setting, these MEW class I downmodulating modifications mitigate alloreactive T cell recognition.

Figure 1:
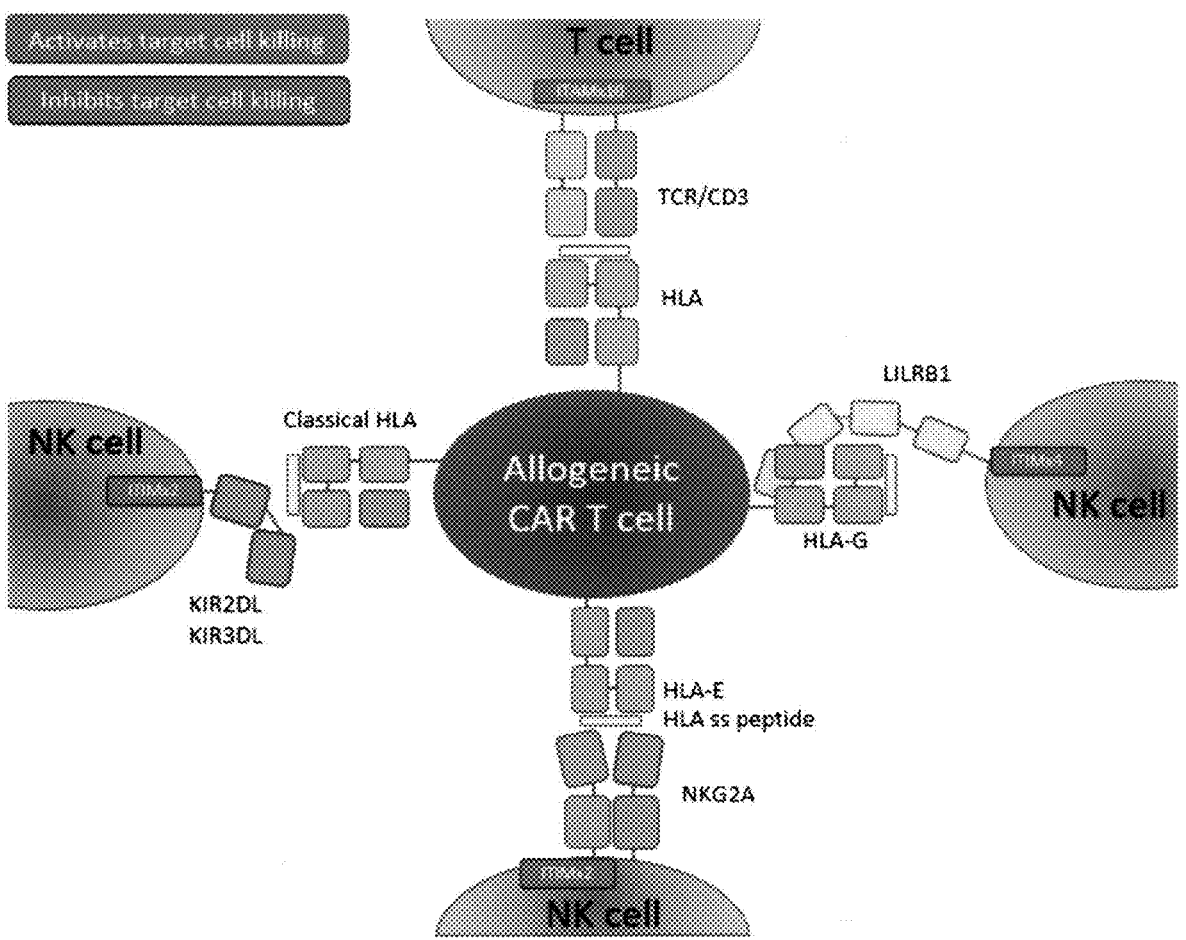
FIG. 1 presents a non-comprehensive illustration of interactions between peptide-MHC complexes on an allogeneic CAR-T cell (center) and receptors on host T (top) and NK cells (left, right, bottom). Through the TCR, T cells kill foreign cells by recognizing non-self peptides presented by the MHC (labelled "HLA" in FIG. 1). Through myriad inhibitory receptors (KIR2DL and KIR3DL, NKG2A, LILRB1), NK cells recognize 'missing self' as the absence of MHC interactions.
Figure 2A:
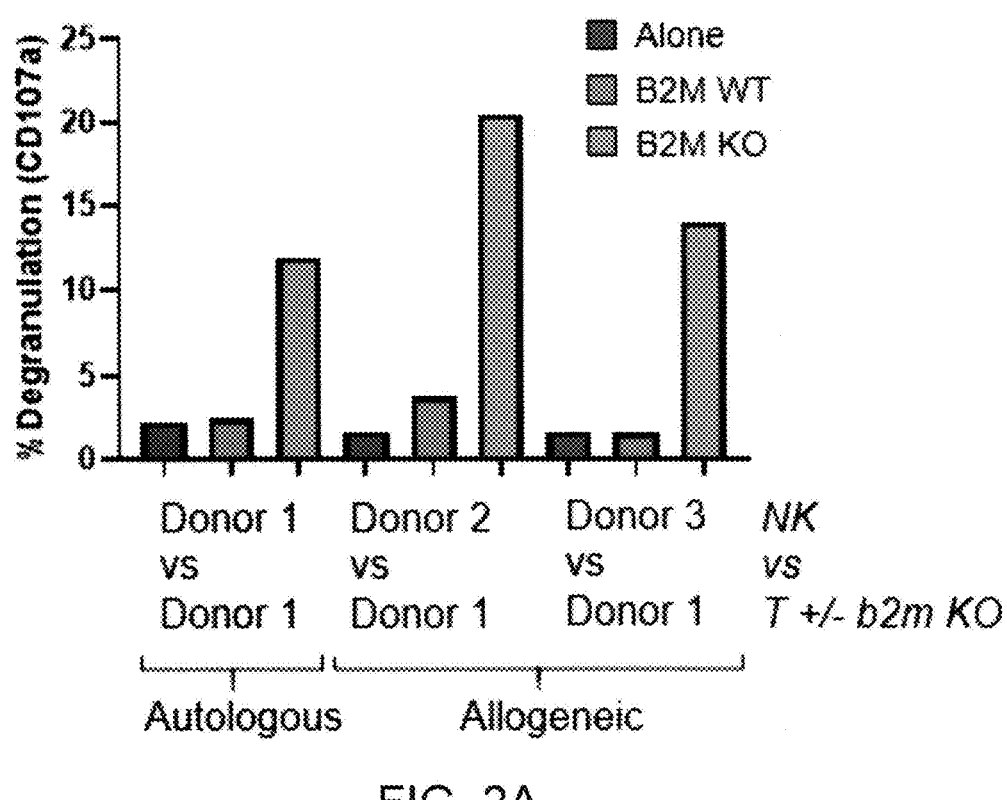
FIGS. 2A-2B. T cells lacking surface MEW induce NK cell degranulation and are selectively killed.
Figure 2B:
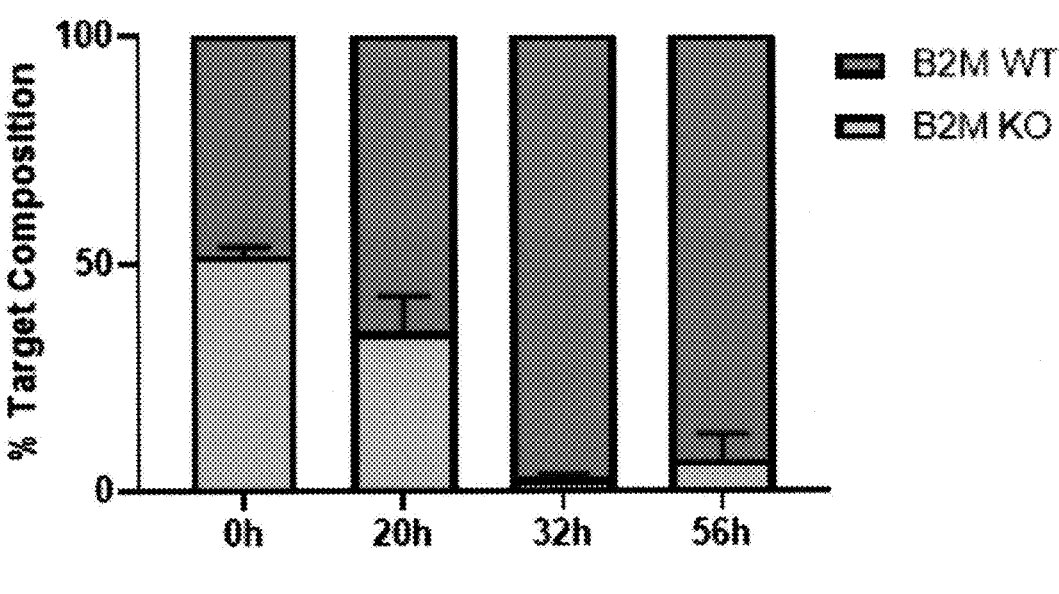
Figure 3:
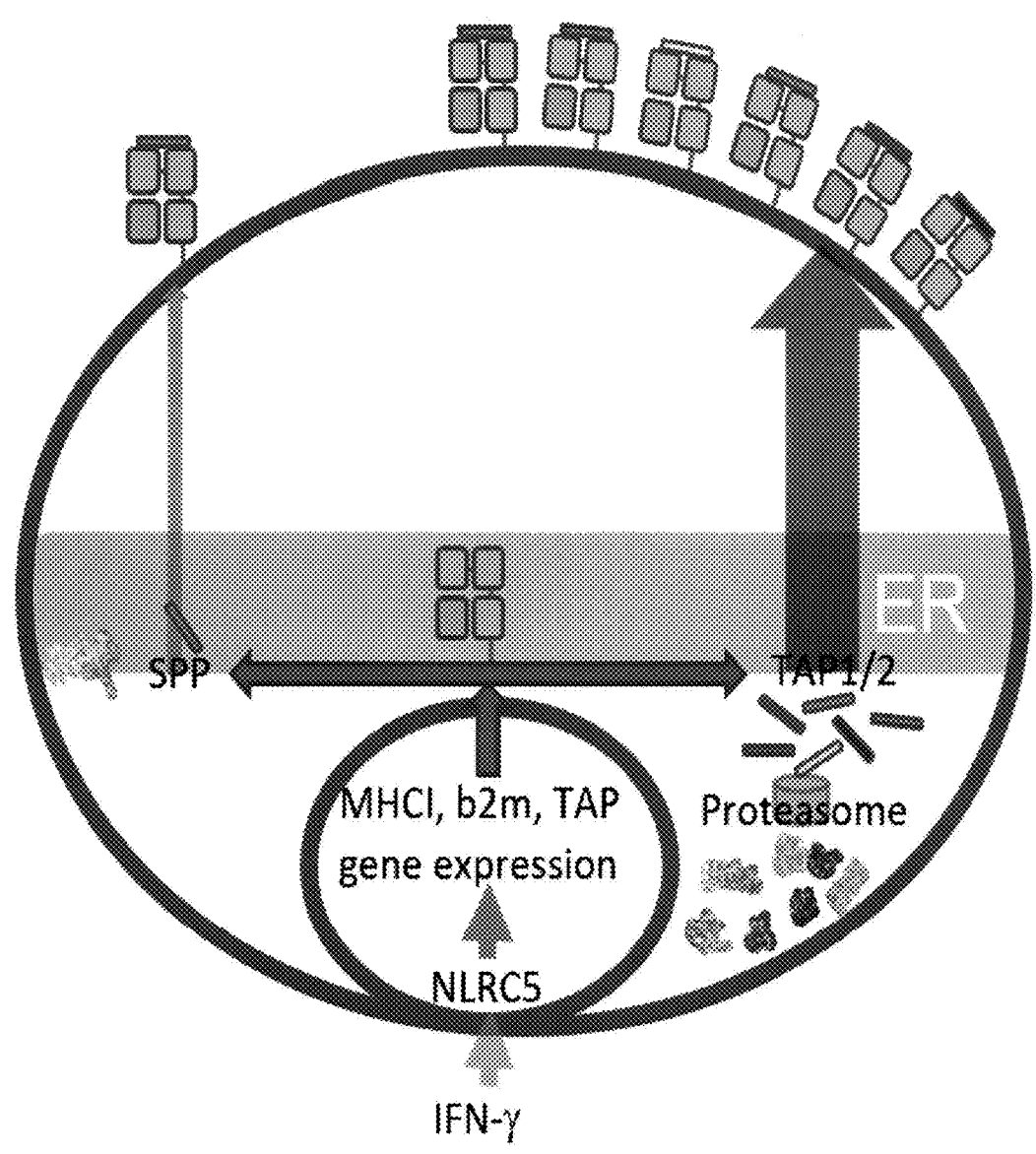
FIG. 3 illustrates MEW class I biogenesis and peptide-loading pathways in nucleated mammalian cells. Multiple MHC-related genes (MEW class I, b2m, TAP, proteasomal components) are under transcriptional control of IFN-γ (IFN gamma)-inducible NLRC5. The dominant pathway by which MHC class I molecules are loaded with diverse, proteasomally-generated peptides is TAP-dependent. Alternately, a comparatively small number of less diverse signal peptides liberated by the signal peptide peptidase (SPP) can be loaded to MHC class I molecules independent of proteasome and TAP.
Figure 8A:
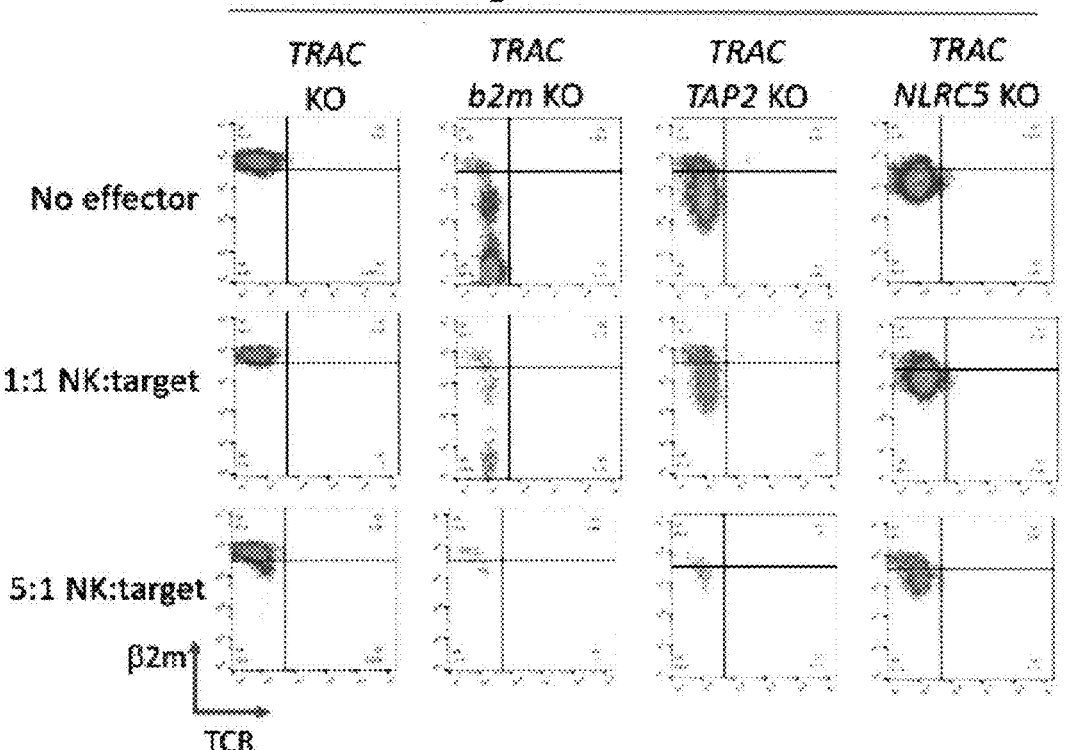
FIGS. 8A-8C. TAP2 KO and NLRC5 KO T cells are less susceptible than b2m KO T cells to NK-mediated killing. Pan T cells edited to be TRAC KO and b2m, TAP2, or NLRC5 KO were co-incubated for 72 h in the presence of 1000 U/mL IL-2 with allogeneic effector NK cells at a ratio of 0:1, 1:1, or 5:1 NK:T cells. Surviving targets were counted by flow cytometry.
Figure 8B:
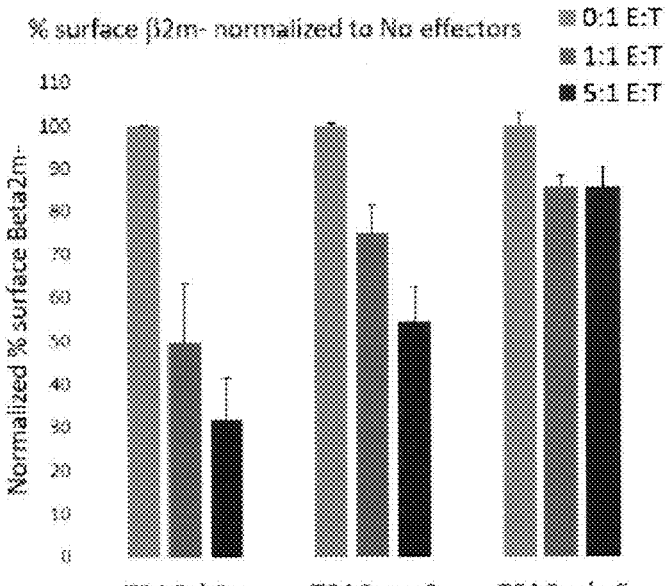
Figure 8C:
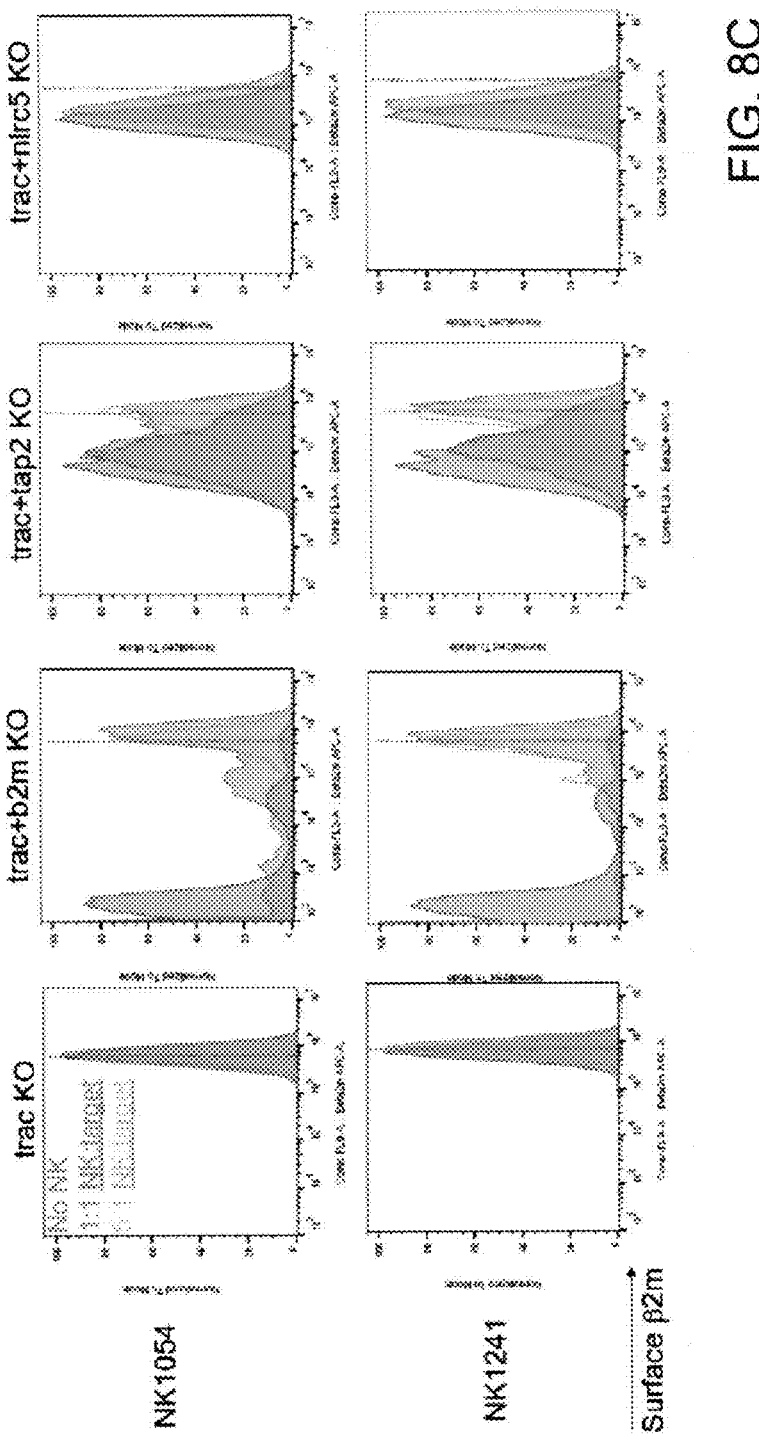

Example 3. TAP2 KO and NLRC5 KO T Cells are Less Susceptible than 132m KO T Cells to NK-Mediated Killing Ablation of surface MEW through 132m KO incurs NK-mediated killing (FIGS. 2A-2B). To determine if the modest downmodulation of surface MEW resulting from TAP2 KO or NLRC5 KO (FIGS. 4A-4B) similarly incurs NK-mediated killing, pan T target cells were edited for TRAC KO and either β2m, TAP2, or NLRC5 KO via CRISPR/Cas9. TCR-negative target T cells were co-incubated for 72 hours with freshly isolated NK cells from an allogeneic donor at a 0:1, 1:1, or 5:1 NK effector:T target ratio. NK-mediated killing was evaluated by flow cytometry (see FIGS. 8A-8C). As previously observed, b2m KO T cells were efficiently killed by allogeneic NK cells at either 1:1 or 5:1. By contrast, the majority of TAP2 KO T cells survived incubation with 1:1 NK:T and NLRC5 KO T cells were almost entirely retained even at 5:1 NK:T (FIG. 8A). Identical incubations with NK cells from two additional allogeneic donors yielded similar results, indicating TAP2 KO and, particularly, NLRC5 KO T cells incur less NK-mediated killing than do b2m KO T cells (FIG. 8B). Because editing efficiency is not 100%, the T cells used in this experiment contain unedited cells as well as those edited at the β2m, TAP2, or NLRC5 loci. If NK-mediated killing exerts selection against edited cells, then the addition of NK cells will cause a shift from MEW null/low (edited) cells toward MEW replete (unedited) cells. Indeed, addition of 1:1 NK cells resulted in almost complete selection of unedited cells over β2m KO cells, while 5:1 NK cells were required for comparable selection of unedited cells over TAP2 KO cells (FIG. 8C). T cells edited at the MRCS locus did not exhibit this selection even at 5:1 NK cells, further evidencing their apparent exemption from NK-mediated killing pursuant to missing self.

Example 4. NLRC5 KO does not Impair DLL3 CAR-Mediated Cytotoxicity

It was also shown that NLRC5 KO does not impair an exemplary DLL3 CAR-mediated cytotoxicity (see FIGS. 10A-10B). The exemplary DLL3 CAR sequence is shown in Table 3. Anti-DLL3 CAR' T cells comprising TRAC KO (black triangles) or TRAC KO plus NLRC5 KO (inverted triangles) exhibited similar short-term cytotoxicity when co-incubated with DLL3$^{high}$-expressing WM266.4 tumor cells (FIG. 10A, three different effector:target ratios shown) and DLL3$^{low}$-expressing DMS273 tumor cells (FIG. 10B). When target cells were grown alone (dots) or in the presence of non-transduced T cells (squares), the target cell numbers grew exponentially and declined at rates similar to each other. The following methods were used in this experiment.

Short-term Killing: Methods

Cytotoxicity was determined by measuring the number of tumor target cells over time using the Incucyte platform (Sartorius). Briefly, WM266.4 tumor cells were engineered with lentivirus to stably express NucLight Green (Sartorius Cat #4475), a nucleus-restricted GFP, and used as target cells. The target cells were plated in a 96-well plate at a density of 5,000 cells per well. DLL3 CAR T cells were thawed and added to the plated target cells at varying effector:target (E:T) ratios. The number of target cells (GFP+) was counted every 6 hours for a total of 132 hours.

Anti-DLL3 CAR' T cells comprising TRAC KO (black triangles) or TRAC KO plus NLRC5 KO (inverted triangles)

also exhibited similar cytotoxicity to each other when incubated with target cells for a longer time (FIG. 10C). The following methods were used in these experiments.

Serial Killing: Methods

Cytotoxicity was determined by measuring the reduction in luminescence signal from live target cells. WM266.4 tumor cells were engineered with lentivirus to stably express luciferase and used as target cells. The target cells were plated in a 96-well plate at a density of 5,000 cells per well. DLL3 CAR T cells were thawed and added to the plated target cells at a 3:1 E:T ratio. Every 2-4 days, half of the cells were transferred to a white walled 96-well plate and incubated with OneGlo substrate (Promega, Cat #E6110) at a 1:1 ratio (v:v) for 2 min at room temperature with shaking. Relative luminescence units were measured using a SpectraMax M3 plate reader (Molecular Devices) and background subtracted against wells without any cells. % Cytotoxicity=100×[1−(RLUtest/RLUcontrol)]. Untreated target cells were used to determine RLUcontrol.

Example 5. Manufacturability

Figure 9A:
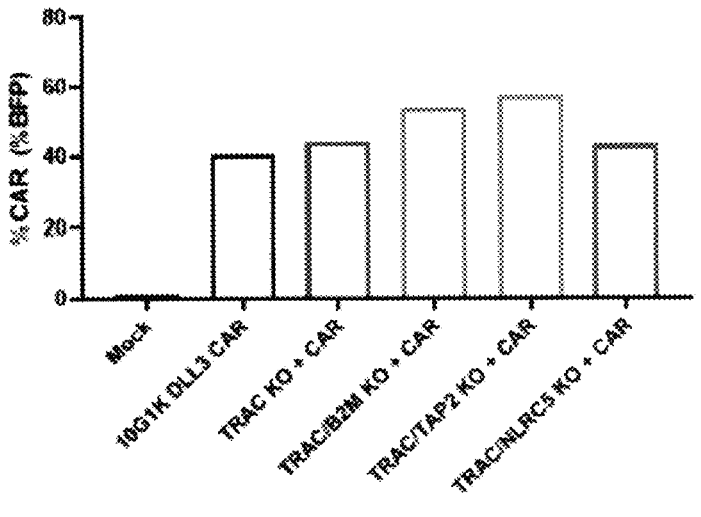
FIGS. 9A-9B. Preliminary manufacturability assessment of disclosed gene editing strategies.
Figure 9B:
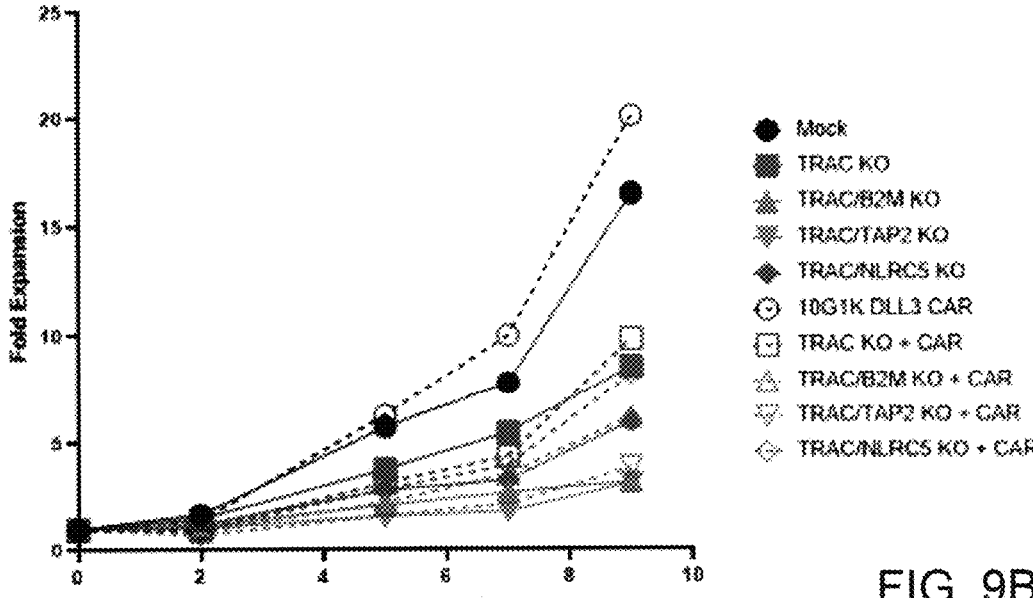

To test the manufacturability of these engineering strategies, proliferation and transduction efficiency in combination with a DLL3-specific CAR was assessed. Pan T cells were gene edited and transduced for CAR expression concurrently and negatively selected for TCR expression. Gene edited cells transduced at comparable efficiencies compared to just CAR transduction alone (FIG. 9A). Furthermore, expansion of cells expressing DLL3 CAR in combination with TRAC KO and NLRC5 KO exhibited similar growth rates compared to DLL3 CAR and TRAC KO alone (FIG. 9B).

Example 6. Activity of Immune Evasion Gene KO

Effect of RFX and Other KO on MHC Expression

Knockout T cell lines were prepared, each of which comprised a knockout for one of β2m, NLRC5, RFX5, CIITA, RFXANK and RFXAP, as described above, using the corresponding sgRNA of SEQ ID NOs: 1-11 to generate the knockout. The effects of each knockout on the cell surface expression level of HLA-ABC (MHC-I) and of HLA-DR, DP, DQ (MHC-II) were assessed by flow cytometry 7 days post gene editing and compared to the effect of mock gene editing (see FIGS. 11A-11B). The data indicate, among other things, that a knockout of either of RFX5 and RFXANK causes a significant reduction in cell surface expression level of both HLA-ABC (MHC-I) and HLA-DR, DP, DQ (MHC-II).

A similar experiment was performed to compare TRAC+ β2m double KO, TRAC+NLRC5 double KO and TRAC+ RFX5 double KO prepared from three independent T cell donors (see FIGS. 12A-12B). TRAC single KO was used as a control. It was observed that, for cells from all three donors, MHC-II and surprisingly also MHC-I expression levels were both significantly lower in the RFX5 KO than in the TRAC KO (see FIGS. 12A-12B).

Growth of Immune Evasion T Cells

Figure 13A:
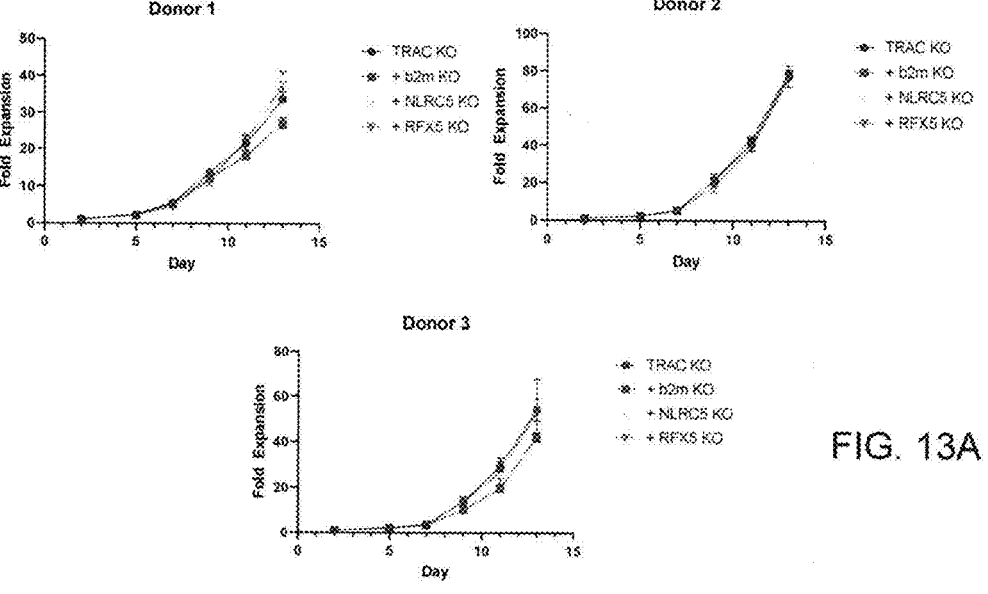
FIGS. 13A-13B. Growth of Immune Evasion T cells.
Figure 13B:
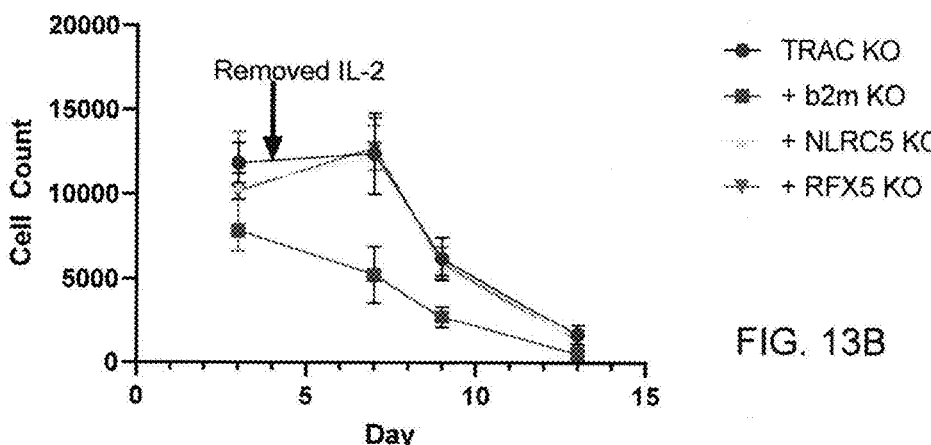

The ability to grow of β2m+TRAC, NLRC5+TRAC and RFX5+TRAC double knockouts, each prepared from three independent T cell donors, was assessed (see FIGS. 13A-13B). Over a period of about 11 days after gene editing, cell expansion reached over 30-fold, over 70-fold, and over 40-fold, with no significant difference between RFX5 double knockout, NLRC5 double knockout, and TRAC single knockout (see FIG. 13A).

Persistence of cells was also assessed by maintaining knockout cells in media lacking IL-2. Cell count remained essentially the same three days after removal of IL-2 and declined by approximately 50% at five days after removal of IL-2. No difference was observed between NLRC5+TRAC double KO, RFX5+TRAC double KO and the control TRAC KO. 20K cells were seeded in a 96-well plate with 20 IU/mL IL-2. On day 4, media was exchanged without IL-2. Media was re-fed every 2-3 days thereafter (see FIG. 13B).

Downmodulation of MHC-I/II Expression Mitigates Alloreactivity a. In Vitro Allogeneic Rejection Assays: Primed T Mixed Lymphocyte Reaction (MLR)

Double KO T cells were co-cultured with primed T cells to determine whether KO T cells had a survival rate different from that of control TRAC KO cells. Specifically, T cells from two allogeneic donors were primed against irradiated cells from a graft donor for 1 week. T cells from the graft donor were edited to make KO cells (KO for TRAC (control), double KO for TRAC+β2m, TRAC+NLRC5, or TRAC+RFX5), and the KO graft cells were co-cultured with the primed CD4+, CD8+, and pan T cells. The number of graft KO cells that survived co-culturing with the primed T cells was determined. A significantly higher proportion of TRAC+RFX5 KO cells than of TRAC KO cells survived the co-culturing with the primed cells for both donors and for all three T cell populations (CD4+, CD8+, and pan T cells) (see FIG. 14A: CD4+ cells, FIG. 14B: CD8+ cells, and FIG. 14C: pan T cells).

Figure 14A:
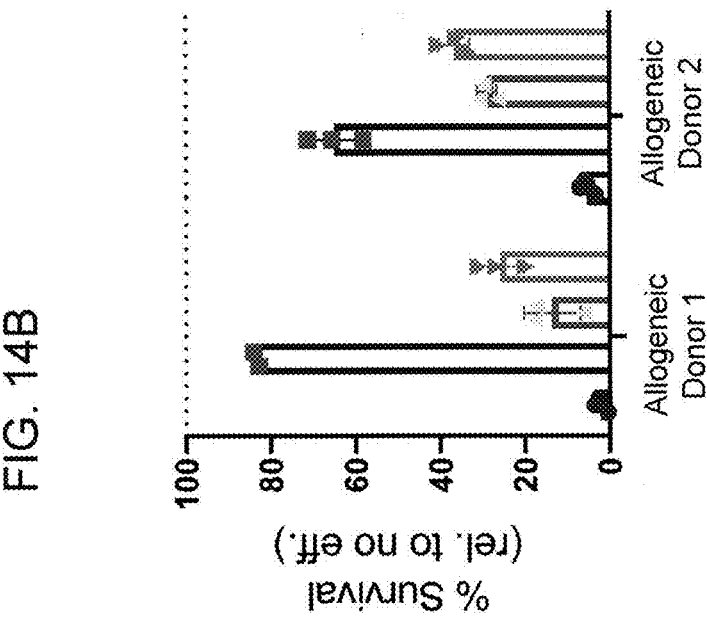
FIGS. 14A-14C. Downmodulation of MHC-I/II expression mitigates T cell alloreactivity. T cells from two allogeneic donors were primed against irradiated cells from a graft donor for 1 week.
Figure 14B:
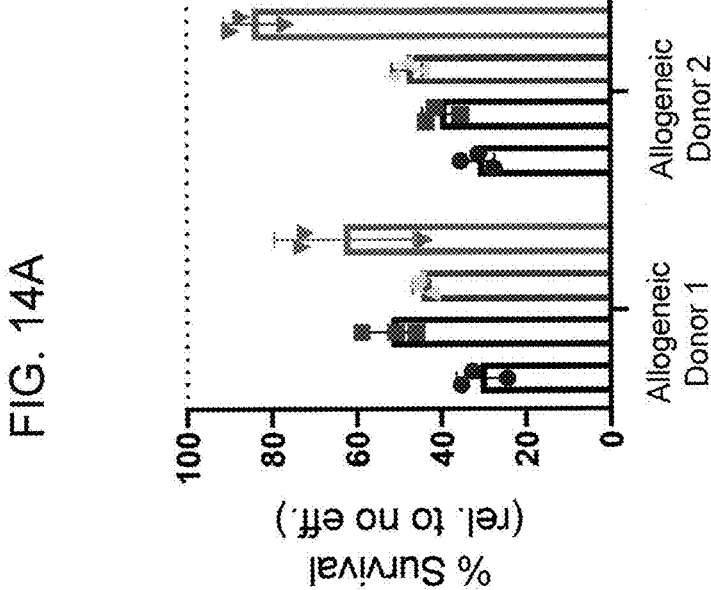
Figure 14C:
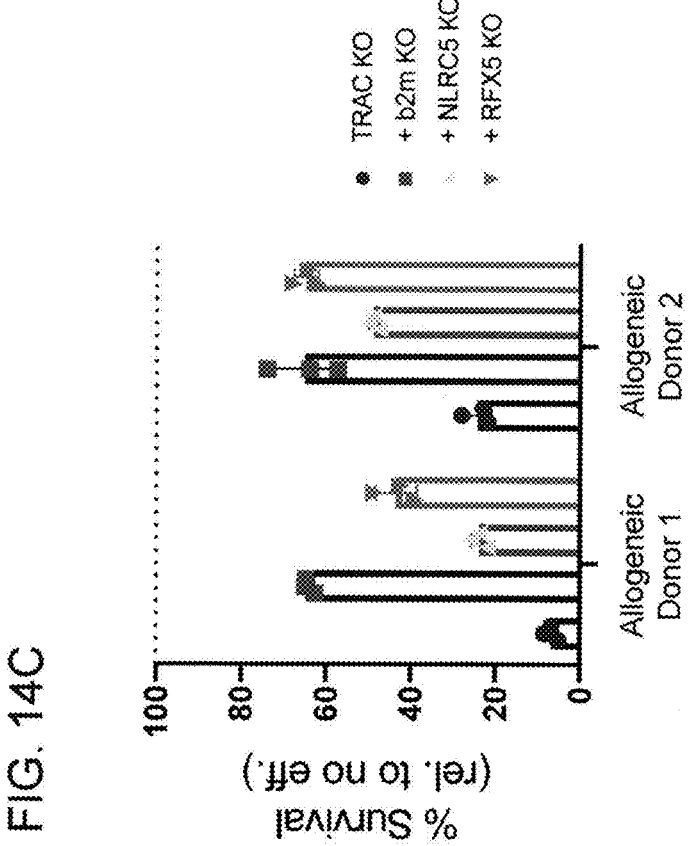

Methods: T cells from two allogeneic donors were primed against irradiated cells from a graft donor for 1 week. CD4+ cells, CD8+ cells, or pan T cells were purified thereafter and co-cultured with graft T cells for 48 h at a 1:1 E:T ratio. One-way killing of graft T cells was assessed by flow cytometry. In FIGS. 14A-14C, mean±SD of technical triplicate is shown. % Survival=Cell Counts/(Cell Counts without Effectors)×100. Knockouts were prepared as described above.

b. TRAC+NLRC5 and TRAC+RFX5 Double KO T Cells are Minimally Killed by Allogeneic NK Cells Graft cells from three different donors were edited to make KO (TRAC) or double KO (TRAC+one of β2m, NLRC5, or RFX5), and the KO graft cells were co-cultured with the NK cells. The number of graft KO cells that survived co-culturing with the NK cells was determined. Over half of the NLRC5 KO cells and over half of the RFX5 KO cells survived the co-culturing with the NK cells (see FIG. 15A).

Methods in brief: NK cells were isolated from allogeneic PBMCs and co-cultured with graft T cells in the presence of 1000 IU/mL IL-2 for 48 h at a 1:1 E:T ratio. One-way killing of graft T cells assessed by flow cytometry. See also below for additional or alternative methods, description of NK Mixed Lymphocyte Reaction (MLR).

Figure 15B:
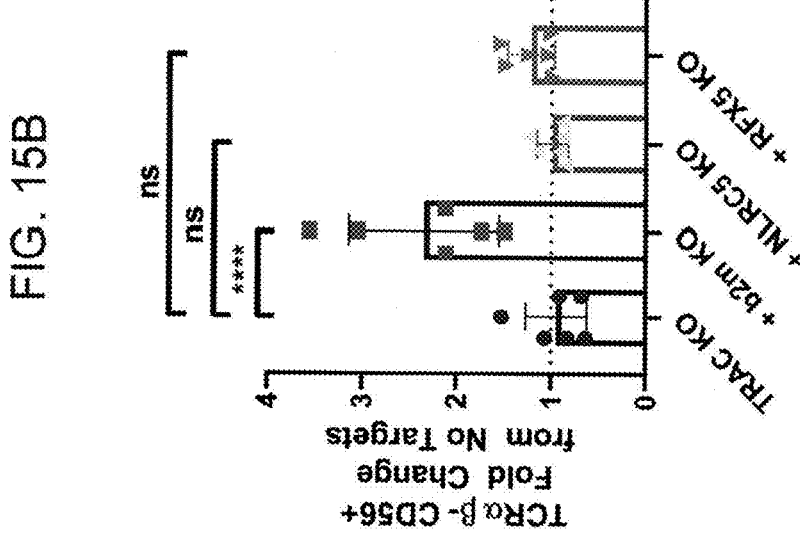
FIGS. 15A-15B. MRCS KO and RFX5 KO T cells are minimally killed by allogeneic NK cells.
Figure 15A:
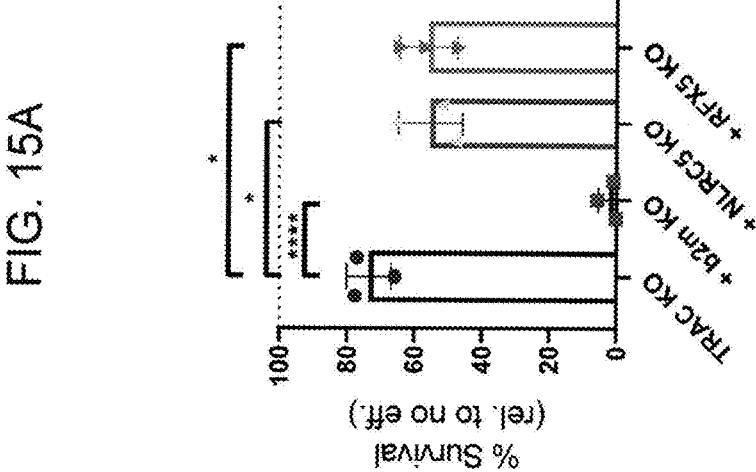

Methods for FIG. 15B: Allogeneic PBMCs were co-cultured with TRAC KO graft T cells with various gene editing modifications for 7 days at a 10:1 E:T ratio. Expansion of allogeneic NK cells was determined by flow cytometry using absolute cell counts gated on TCRαβ− CD56+ cells and normalized to allogeneic NK cells cultured in the absence of graft cells. Mean±SD of 6 biological replicates shown.

Figure 16:
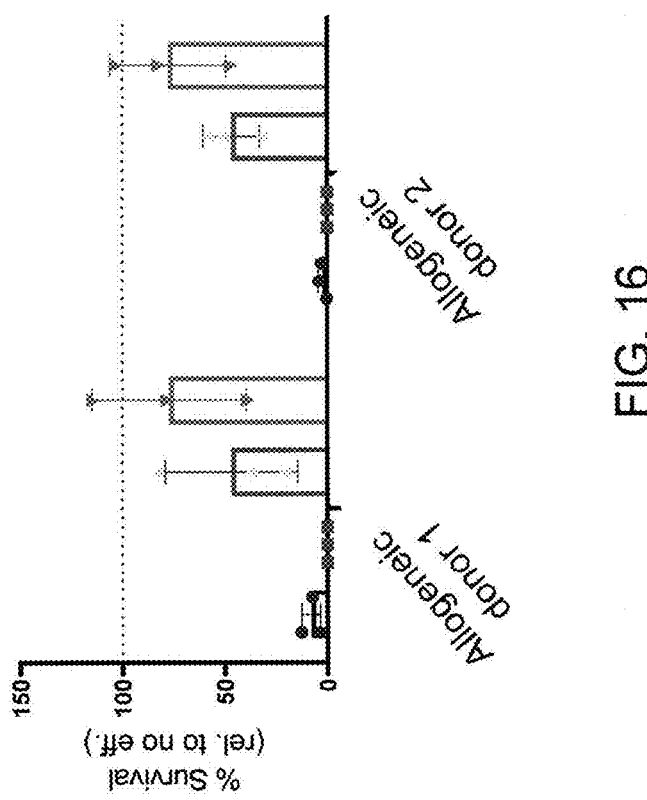
FIG. 16. Survival of graft T cells harboring various gene knockouts (KO) after co-culturing with allogeneic PBMCs from either of two donors. Allogeneic PBMCs were co-cultured with TRAC KO graft T cells with various gene editing modifications (TRAC KO alone or with KO of one of β2m, MRCS and RFX5) for 9 days at a 10:1 E:T ratio. Survival of graft T cells was determined by flow cytometry and normalized to the graft T cells cultured without any effectors. Mean±SD of technical triplicate shown.

Methods for FIG. 16. Allogeneic PBMCs were co-cultured with TRAC KO graft T cells with various immune evasion modifications for 9 days at a 10:1 E:T ratio. Survival of graft T cells was determined by flow cytometry and normalized to the graft T cells cultured without any effectors. Mean±SD of technical triplicate shown.

Example 7. Overexpression of US11

It was also shown that US11 overexpression enhances alloreactive T cell avoidance and can be combined with NLRC5 knockout to obtain greater effectiveness than either provides alone (see FIGS. 17A-17D). The following methods were used for the experiment shown in FIG. 17B (and also used for the experiments shown in FIGS. 7 and 14A-C):

Generation of US11 Overexpressing T Cells: Methods

Figure 18:
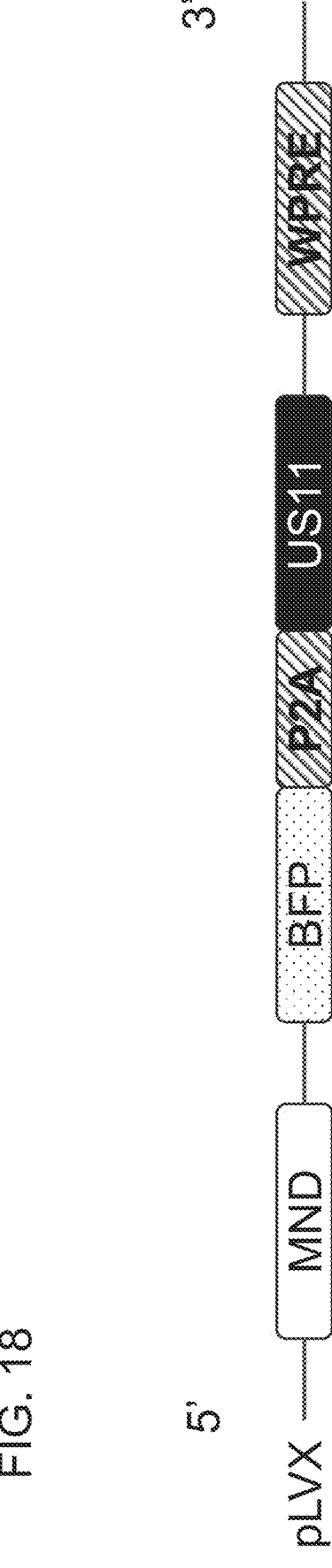
FIG. 18 is a schematic depicting a lentiviral vector (LVV) encoding HCMV US11.

To make lentivirus encoding US11, HEK-293T cells were plated at 0.75 million cells per mL of DMEM (Gibco) supplemented with 10% FBS (HyClone), non-essential amino acids (Gibco), and sodium pyruvate (Gibco) in a 10 cm dish pre-coated with poly-L-lysine (R and D Systems). On the next day, plasmid encoding US11 on a pLVX backbone (SEQ ID. 8-12; FIG. 18) was mixed with lentiviral packaging vectors psPAX2 and pMD2G at a 3:4:1 mass ratio. Lipofectamine 2000 (Invitrogen) was added per manufacturer's recommendations and lipid-DNA complexes were formed after incubation for 20 min at room temperature. The mixture was added drop-wise to the HEK-293T monolayer (~70-90% confluence) and the cells were incubated overnight at 37° C., 5% $CO_2$. After 16-20 h, the media was replaced with R10. After 48 h, the supernatant was collected and filtered through a 0.45 μm filter. Virus was concentrated 20× with Lenti-X (Takara Bio) and added at a 1:10 dilution to 1 million T cells activated with TransAct (1:100) two days prior. Transduction efficiency was assessed by flow cytometry by expression of blue fluorescent protein (BFP+).

Primed T Mixed Lymphocyte Reaction (MLR)

Human PBMCs (host) were primed against irradiated PBMCs derived from donors used to make graft T cells above to promote expansion of alloreactive T cell clones. Briefly, graft PBMCs were irradiated at 30 Gy and co-cultured with host PBMCs at a 1:1 ratio in R10+20 IU/mL IL-2+10 ng/mL IL-7+10 ng/mL IL-15 (Miltenyi, Cat #130-095-765) for 4 days. Media was exchanged to R10 without cytokines and the cells were continued to culture for 3 more days. Afterwards, pan T cells were isolated using MACS negative selection (Miltenyi, human pan T cell isolation kit, Cat #130-096-535) per the manufacturer's recommendations. In a 96-well plate, 20,000 graft T cells were seeded with 20,000 primed host T cells and cultured in R10+20 IU/mL IL-2 for 2 days at 37° C., 5% $CO_2$. Survival of graft T cells was determined by flow cytometry using absolute counts by gating on live TCRαβ− CD4+CD8+.

Figure 17A:
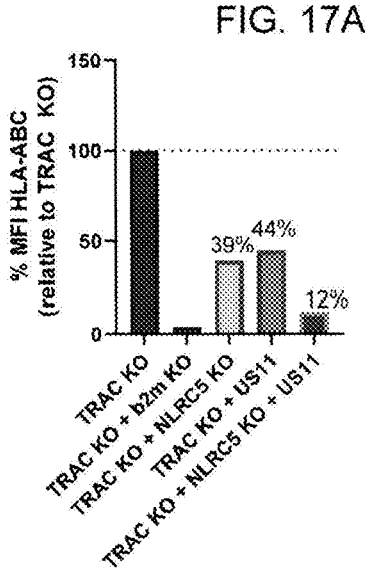
FIGS. 17A-17D. US11 overexpression enhances alloreactive T cell avoidance.
Figure 17B:
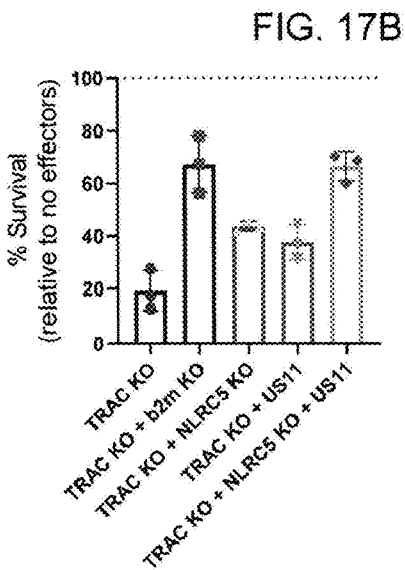
Figure 17C:
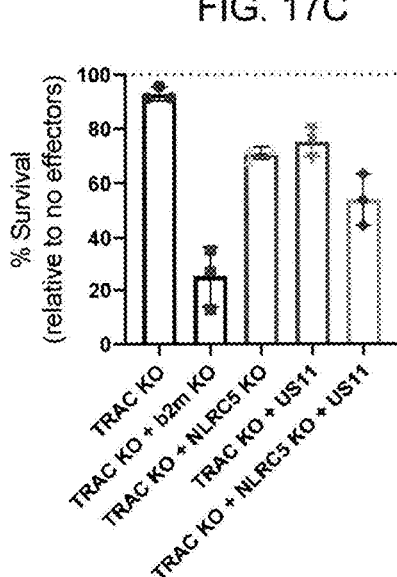
Figure 17D:
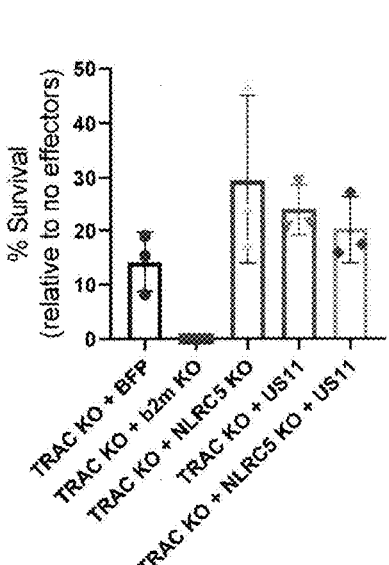

The following methods were used for the experiment shown in FIG. 17C (and also used for the experiments shown in FIGS. 8A-8B and 15A):

NK Mixed Lymphocyte Reaction (MLR)

Human NK cells were isolated from freshly isolated human PBMCs via MACS purification (Miltenyi, human pan NK cell isolation kit, Cat #130-092-657). In a 96-well plate, 20,000 graft T cells were seeded with host NK cells and cultured in R10+1000 IU/mL IL-2 for 2 days at 37° C., 5% $CO_2$. Survival of graft T cells was determined by flow cytometry using absolute counts by gating on live TCRαβ− CD56− CD4+CD8+.

TABLE 2

| US11 Lentiviral Vector (LVV) | | |
| --- | --- | --- |
| SEQ ID NO: | Description | DNA sequence (5' - 3') |
| 13 | MND Promoter | TAGTCCAATTTGTTAAAGACAGGATATCAGTGGTCCAGGCT<br>CTAGTTTTTGACTCAACAATATCACCAGCTGAAGCCTATAGA<br>GTACGAGCCATAGATAAAATAAAAGATTTTATTTAGTCTCC<br>AGAAAAAGGGGGGAATGAAAGACCCCACCTGTAGGTTTGGC<br>AAGCTAGGATCAAGGTCAGGAACAGAGAAACAGGAGAATAT<br>GGGCCAAACAGGATATCTGTGGTAAGCAGTTCCTGCCCCGC<br>TCAGGGCCAAGAACAGTTGGAACAGGAGAATATGGGCCAAA<br>CAGGATATCTGTGGTAAGCAGTTCCTGCCCCGCTCAGGGCC<br>AAGAACAGATGGTCCCCAGATGCGGTCCCGCCCTCAGCAGT<br>TTCTAGAGAACCATCAGATGTTTCCAGGGTGCCCCAAGGAC<br>CTGAAATGACCCIGTGCCTTATTTGAACTAACCAATCAGTT<br>CGCTTCTCGCTTCTGTTCGCGCGCTTCTGCTCCCCGAGCTC<br>AATAAAAGAGCCCACAACCCCTCACTCGGCGCGATC |
| 14 | BFP | atgagcgagctgattaaggagaacatgcacatgaagctgta<br>catggagggcaccgtggacaaccatcacttcaagtgcacat<br>ccgagggcgaaggcaagccctacgagggcacccagaccatg<br>agaatcaaggtggtcgagggcggccctctccccttcgcctt<br>cgacatcctggctactagcttcctctacggcagcaagacct<br>tcatcaaccacacccagggcatccccgacttcttcaagcag<br>tccttccctgagggcttcacatgggagagagtcaccacata<br>cgaagacgggggcgtgctgaccgctacccaggacaccagcc<br>tccaggacggctgcctcatctacaacgtcaagatcagaggg<br>gtgaacttcacatccaacggccctgtgatgcagaagaaaac<br>actcggctgggaggccttcaccgagacgctgtaccccgctg<br>acggcggcctggaaggcagaaacgacatggccctgaagctc<br>gtgggcgggagccatctgatcgcaaacatcaagaccacata<br>tagatccaagaaacccgctaagaacctcaagatgcctggcg<br>tctactatgtggactacagactggaaagaatcaaggaggcc<br>aacaacgagacctacgtcgagcagcacgaggtggcagtggc<br>cagatactgcgacctccctagcaaactggggcacaagctta<br>at |
| 15 | P2A | gcaacgaatttcagcctgctgaagcaggccggggacgtcga<br>ggagaatccagggcca |
| 16 | US11 (merlin) | ATGAACCTGGTCATGCTGATCCTGGCCCTGTGGGCCCCCGT<br>GGCAGGCAGCATGCCTGAGCTGTCCCTGACCCTGTTCGACG<br>AGCCCCCTCCACTGGTGGAGACAGAGCCACTGCCACCTCTG<br>TCCGACGTGAGCGAGTACAGAGTGGAGTATTCTGAGGCAAG<br>ATGCGTGCTGAGAAGCGGCGGCAGGCTGGAGGCCCTGTGGA<br>CCCTGCGCGGCAATCTGAGCGTGCCAACCCCCACACCTCGG<br>GTGTACTATCAGACCCTGGAGGGATACGCAGACAGGGTGCC<br>AACACCCGTGGAGGACGTGAGCGAGAGCCTGGTGGCCAAGA<br>GATACTGGCTGAGGGACTATCGCGTGCCACAGAGGACCAAG<br>CTGGTGCTGTTCTATTTTTCCCCCTGCCACCAGTGTCAGAC<br>ATACTATGTGGAGTGCGAGCCTCGCTGTCTGGTGCCTTGGG<br>TGCCACTGTGGAGCTCCCTGGAGGACATCGAGCGGCTGCTG<br>TTCGAGGATCGGAGACTGATGGCCTACTATGCCCTGACCAT<br>CAAGTCCGCCCAGTACACACTGATGATGGTGGCCGTGATCC<br>AGGTGTTTTGGGGCCTGTATGTGAAGGGCTGGCTGCACCGG<br>CACTTCCCATGGATGTTTTCTGATCAGTGG |
| 17 | WPRE | aatcaacctctggattacaaaatttgtgaaagattgactgg<br>tattcttaactatgttgctccttttacgctatgtggatacg<br>ctgctttaatgcctttgtatcatgctattgcttcccgtatg<br>gctttcattttctcctccttgtataaatcctggttgctgtc<br>tctttatgaggagttgtggcccgttgtcaggcaacgtggcg<br>tggtgtgcactgtgtttgctgacgcaacccccactggttgg<br>ggcattgccaccacctgtcagctcctttccgggactttcgc<br>tttccccctccctattgccacggcggaactcatcgccgcct<br>gccttgcccgctgctggacaggggctcggctgttgggcact<br>gacaattccgtggtgttgtcggggaagctgacgtcctttcc<br>atggctgctcgcctgtgttgccacctggattctgcgcggga<br>cgtccttctgctacgtcccttcggccctcaatccagcggac<br>cttccttcccgcggcctgctgccggctctgcggcctcttcc<br>gcgtcttcgccttcgccctcagacgagtcggatctcccttt<br>gggccgcctccccgcctg |

Example 8 Stealth Knockouts T Cells were Insensitive to IFNγ

We tested the effects of IFNγ on MHC surface expression levels in T cells modified with the various gene knockouts. T cells with various gene KOs (TRAC KO alone (control) or TRAC KO plus B2M KO, NLRC5 KO, RFX5 KO, or CIITA KO) were seeded at 3×10⁴ cells/well in 96-well plate with varying concentrations of recombinant human IFN-γ (R&D Systems) for 72 hours. Expression of MHC-I and MHC-II were determined by staining with anti-HLA-ABC and anti-HLA-DR, DP, DQ antibodies (e.g., BioLegend, Cat #311404, 361708), and analyzed with flow cytometry.

Figure 19A:
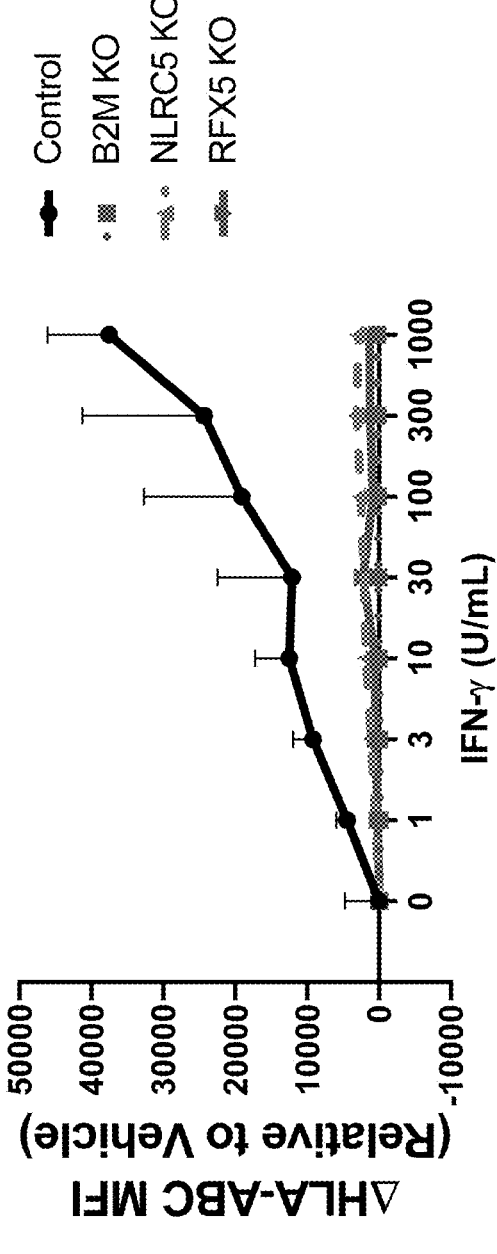
FIG. 19A-19B. Gene-edited T cells were cultured with varying concentrations of recombinant IFN-γ for 72 h. Surface expression of MHC-1 (FIG. 19A) and MHC-II (FIG. 19B) was assessed by flow cytometry. Changes in MHC-I and MHC-II expression were determined relative to vehicle (0 U/mL IFN-γ). Mean±SD of technical triplicate shown.
Figure 19B:
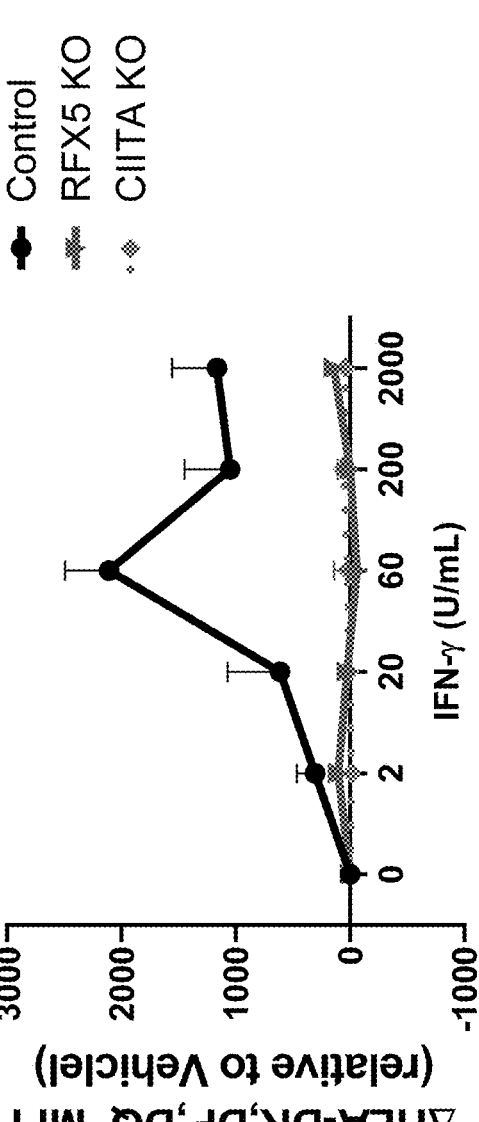

The results in FIGS. 19A-B show that while expression of MHC-I and MHC-II of control T cells (TRAC KO alone) was elevated with increasing concentrations of IFN-γ, MHC-I expression in B2M KO, NLRC5 KO, or RFX5 KO T cells and MHC-II expression in RFX5 KO or CIITA KO T cells remained low regardless of IFN-γ addition, suggesting the levels of MHC expression in stealth-modified T cells were relatively insensitive to IFN-γ.

Example 9 Manufacturing of Stealth CD19 CAR T Cells

Figure 23A:
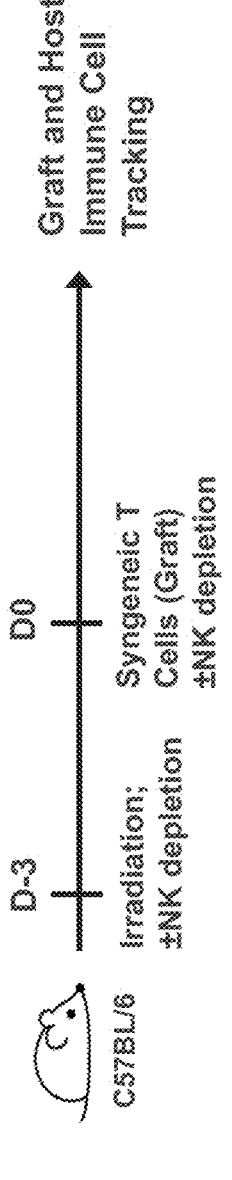
FIGS. 23A-23C. NK cell rejection of graft T cells with various gene knockouts (KO) was assessed in a syngeneic mouse model (FIG. 23A). In vitro expanded control (un-edited) or gene-edited (132m or NLRC5 KO) mouse T cells were injected into syngeneic host mice with or without depletion of host NK cells. Graft T cells in the peripheral blood were identified as CD45.1⁻CD45.2⁺ T cells by flow cytometry. Surface expression of MHC-1 (FIG. 23A) and the survival of graft cells (FIG. 23C) were assessed.

Same methods as described above, e.g., in Examples 4 and 5 were used for production of an exemplary CD19 CART cells with various gene KOs, except T cells were transduced with a lentivirus for the expression of a CD19 CAR. The exemplary CD19 CAR sequence is as shown in Table 3. Gene editing was performed on day 2 (data shown in FIGS. 20-21) or day 5 (data shown in FIG. 23) post T cell thawing and activation, using Neon Transfection System (Invitrogen) or Nucleofector 4D (Lonza). TCR depletion (Stem Cell Technologies, EasySep human TCR alpha/beta depletion kit, Cat #17847) was typically performed between days 14-16. TCR-depleted T cells were cryopreserved and thawed for additional assays at later times. Cell expansion during production was tracked by counting viable cells with Vi-CELL counter (Beckman Coulter). Fold expansion was calculated by comparing viable cell counts at various time points to day 2 (time of gene editing). Percentage of CAR⁺ T cells, CD4/CD8 ratio, and T cell subsets were determined by flow cytometry. CD19 CAR T cells were identified by anti-idiotypic antibody (Acro Biosystems, Cat #FM3HPY53). Phenotypes of CAR⁺CD4⁺ cells or CAR⁺ CD8⁺ cells were determined by CD62L and CD45RO expression and defined as stem-cell memory (CD62L⁺/CD45RO⁻), central memory (CD62L⁺/CD45RO⁺), effector memory (CD62L1⁺/CD45RO⁺), or effector (CD62L⁻/CD45RO⁻) cell populations.

Figures 20A, 20B:
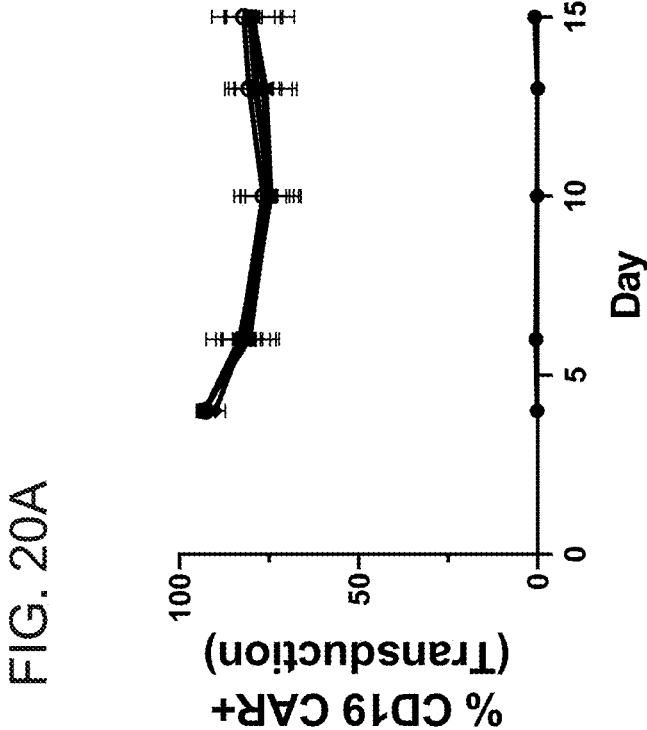
FIGS. 20A-20D. Generation and analysis of stealth-modified CD19 CAR T cells. Percentage of CD19 CAR+ cells with TRAC KO±additional stealth modifications is shown in FIG. 20A. Control: TRAC KO CD19 CAR T cells; NTD: TRAC KO non-transduced T cells. Kinetics of cell expansion during manufacturing are shown in FIG. 20B. Mean±SD of n=4 donors. Control: TRAC KO CD19 CAR T cells; NTD: TRAC KO non-transduced T cells. The CD4/CD8 ratio of one representative donor is shown in FIG. 20C. T cell memory phenotype of one representative donor is shown in FIG. 20D.
Figures 20C, 20D:
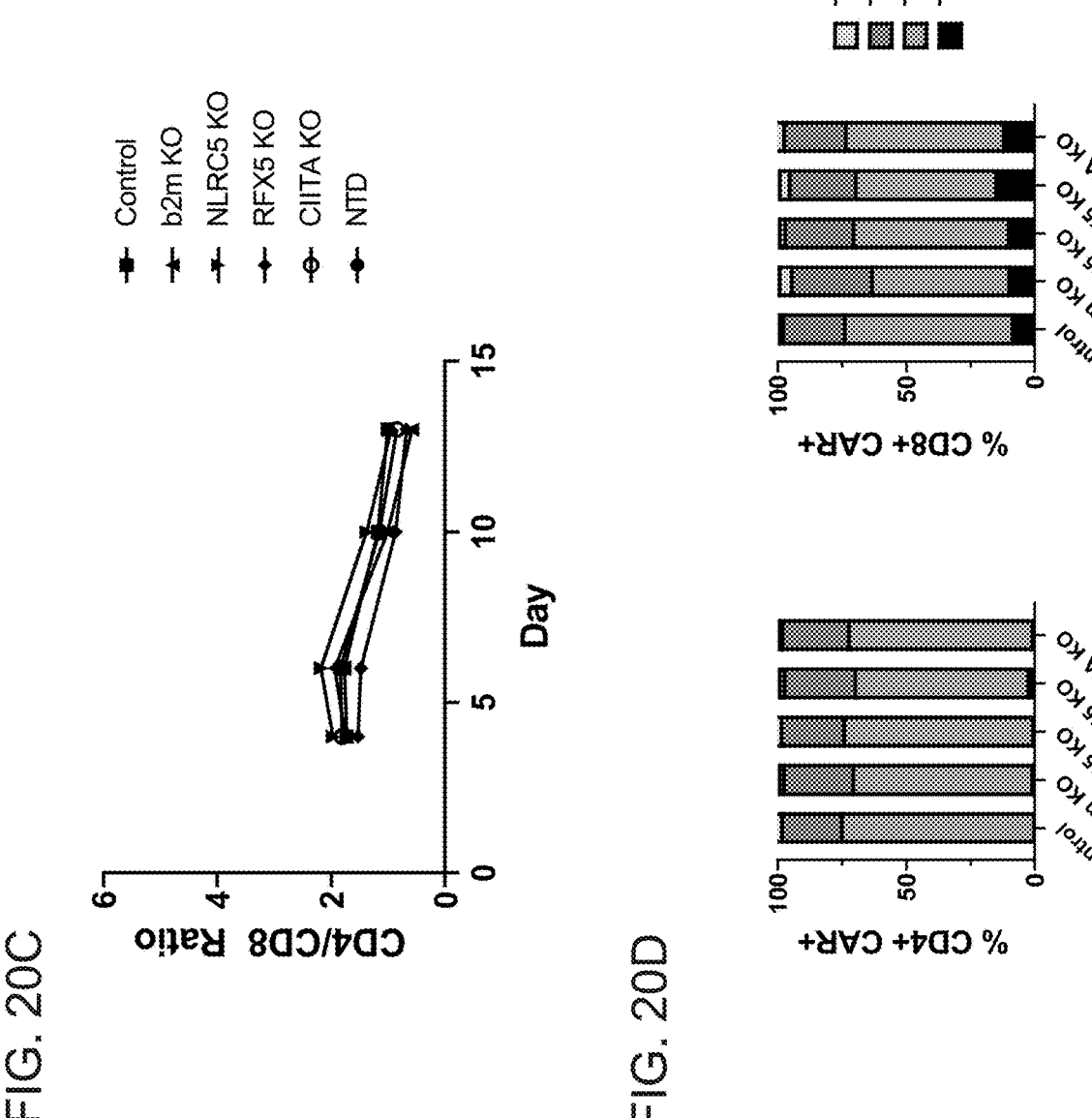

Manufacturability of CD19 CAR T cells with various gene KOs was assessed in a similar manner as the DLL3 CAR T cells. Gene-edited cells were transduced at comparable efficiencies and displayed similar kinetics compared to control CAR T cells throughout production (FIG. 20A). Furthermore, cell expansion (FIG. 20B), CD4/CD8 ratio (FIG. 20C), and memory phenotypes (FIG. 20D) of CAR T cells expressing the CD19 CAR in combination with TRAC KO and various additional KOs were comparable to CD19 CAR T cells with TRAC KO alone.

TABLE 3

| Exemplary CAR sequences | |
| --- | --- |
| CAR sequences | SEQ ID NO: |
| DLL3 CAR<br>MALPVTALLLPLALLLHAARPEVQLLESGGGLVQPGGSLRLSCAASGFTF<br>SSYAMNWVRQAPGKGLEWVSTISGSGGSTYYADSVKGRFTISRDNSKNTL<br>YLQMNSLRAEDTAVFYCAIDPEYYDILTGGDYWGQGTLVTVSSGGGGSGG<br>GGSGGGGSGGGGSDIQMTQSPSAMSASVGDRVTITCRASQGISNYLAWFQ<br>QKPGKVPKRLIYAASSLQSGVPSRFSGSGSGTEFTLTISSLQPEDFATYF<br>CLQHDSFPLTFGGGTKVEIKTTTPAPRPPTPAPTIASQPLSLRPEACRPA<br>AGGAVHTRGLDFACDIYIWAPLAGTCGVLLLSLVITLYCKRGRKKLLYIF<br>KQPFMRPVQTTQEEDGCSCRFPEEEEGGCELRVKFSRSADAPAYQQGQNQ<br>LYNELNLGRREEYDVLDKRRGRDPEMGGKPRRKNPQEGLYNELQKDKMAE<br>AYSEIGMKGERRRGKGHDGLYQGLSTATKDTYDALHMQALPPR | 18 |
| CD19 CAR<br>MALPVTALLLPLALLLHAARPEVKLQESGPGLVAPSQSLSVTCTVSGVSL<br>PDYGVSWIRQPPRKGLEWLGVIWGSETTYYNSALKSRLTIIKDNSKSQVF<br>LKMNSLQTDDTAIYYCAKHYYYGGSYAMDYWGQGTSVTVSSGGGGSGGGG<br>SGGGGSDIQMTQTTSSLSASLGDRVTISCRASQDISKYLNWYQQKPDGTV<br>KLLIYHTSRLHSGVPSRFSGSGSGTDYSLTISNLEQEDIATYFCQQGNTL<br>PYTFGGGTKLEITTTTPAPRPPTPAPTIASQPLSLRPEACRPAAGGAVHT<br>RGLDFACDIYIWAPLAGTCGVLLLSLVITLYCKRGRKKLLYIFKQPFMRP<br>VQTTQEEDGCSCRFPEEEEGGCELRVKFSRSADAPAYQQGQNQLYNELNL<br>GRREEYDVLDKRRGRDPEMGGKPRRKNPQEGLYNELQKDKMAEAYSEIGM<br>KGERRRGKGHDGLYQGLSTATKDTYDALHMQALPPR | 19 |

Example 10 PBMC MLR Assay with CD19 CAR T Cells as Graft

Figures 21A, 21B:
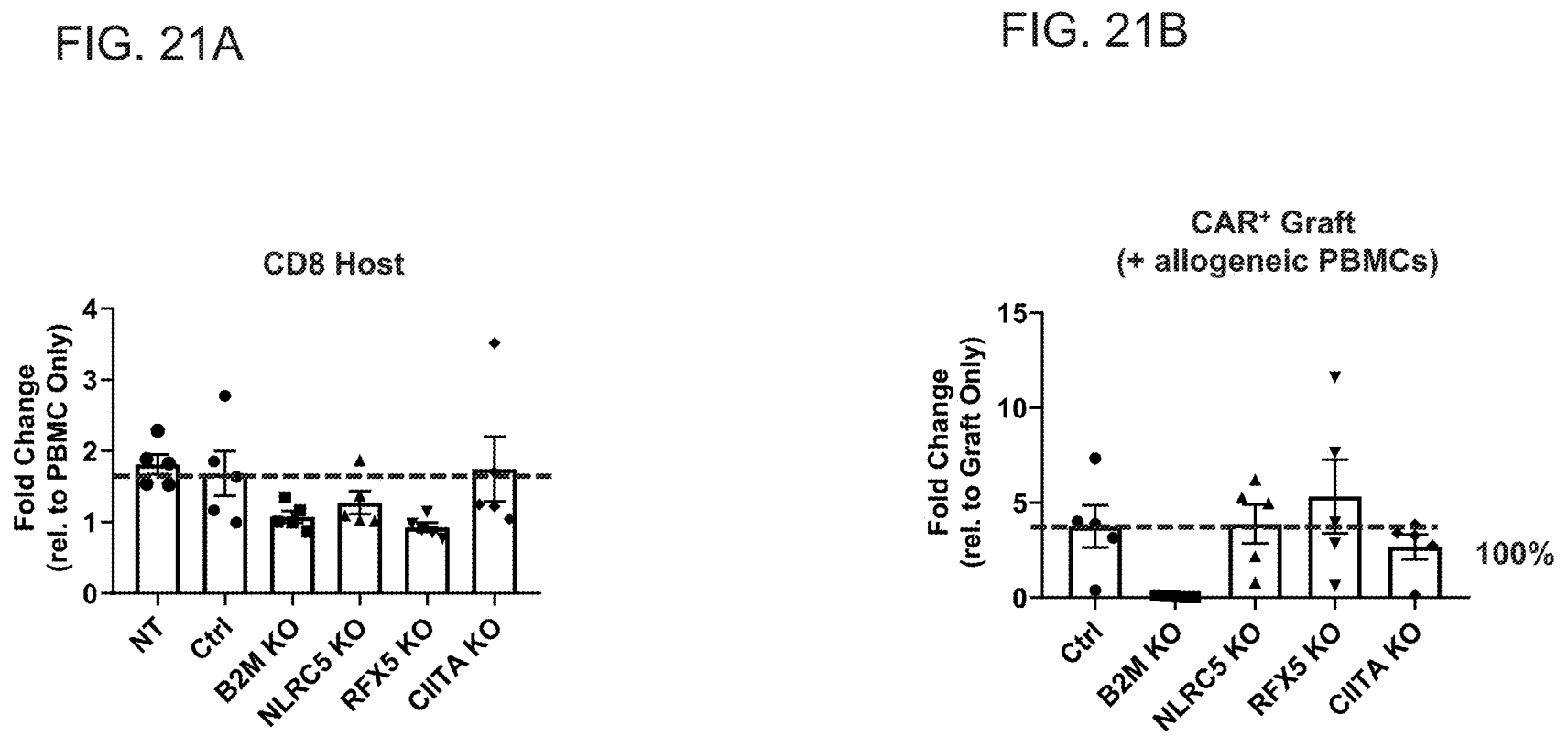

We next examined the survival of graft CD19 CAR T cells harboring various gene knockouts (KO) after co-culturing with allogeneic PBMCs from a different donor. The effect of various gene editing modifications of CAR T cells on mitigating allogeneic immune cell recognition was assessed by in a PBMC MLR assay as described in Example 6 above. The results in FIG. 21A show that knocking out β2m, NLRC5 or RFX5 in CD19 CAR T cells resulted in reduction of host CD8 T cell expansion, suggesting effective mitigation of allogeneic CD8 T cell recognition by reducing MHC-I expression on CD19 CAR T cells. Survival of CD19 CART cells was also quantified. Knocking out NLRC5, RFX5 and CIITA resulted in comparable survival as control CD19 CAR T cells, while knocking out β2m resulted in poor survival of CD19 CAR T cells as compared to control CD19 CAR T cells (FIG. 21B).

Example 11 T Cell Rejection in an NSG Mouse Model

Figure 22A:
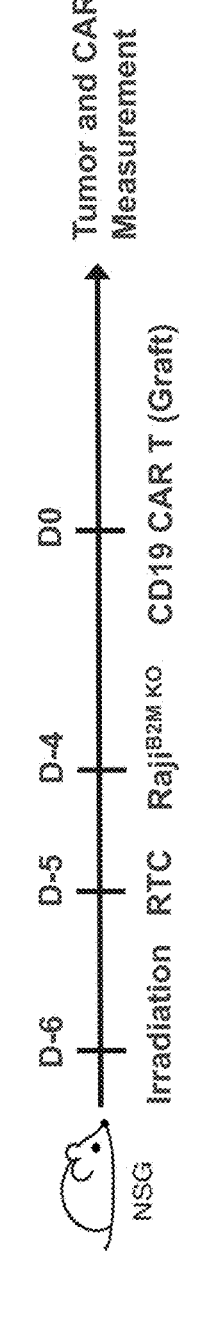
FIGS. 22A-22C. Persistence and anti-tumor efficacy of CD19 CAR T cells with various gene knockouts (KO) were assessed in an allogeneic T cell rejection model in vivo. CD19 CAR T cells with various gene editing modifications (TRAC KO alone or with KO of one of β2m, NLRC5, or RFX5) were injected into NSG mice previously engrafted with human T cells from an allogeneic donor and Raji tumor cells (FIG. 22A). CAR T cell persistence in the peripheral blood (FIG. 22B) and anti-tumor efficacy (FIG. 22C) were determined by flow cytometry and total body bioluminescence, respectively. NT: non-transduced T cells with TRAC KO. Mean±SEM shown.

Persistence and anti-tumor efficacy of CD19 CAR T cells with various gene knockouts (KO) were assessed in an allogeneic T cell rejection model in vivo. 8-12 week old NOD.Cg-Prkdcscid Il2rgtm1Wjl/SzJ (NSG) mice were obtained from Jackson Laboratories (Bar Harbor, ME). NSG mice were irradiated at 1 Gy on day −6 and received 7×10⁶ in vitro expanded allogeneic human T cells derived from an HLA-A2+ recipient. Briefly, allogeneic T cells were activated immediately after recovery from cryopreservation using T cell TransAct™ (Miltenyi Biotec, Auburn, CA; 1:100 dilution), in X-Vivo 15 medium (Lonza, Basel, Switzerland) supplemented with 5% human AB serum (Gemini Bio-Products, West Sacramento, CA) and 100 IU/mL IL-2 (Miltenyi Biotec, Auburn, CA). See FIG. 22A. Two days after activation, T cells were centrifuged to remove Trans-Act, and then resuspended in fresh XVivo-15 medium supplemented with 5% human AB serum and 100 IU/ml IL-2 for 6-8 days before animal dosing, via intravenous injection. On day −4, mice received 1×10⁵ luciferase-labeled B2M KO Raji tumor cells via intravenous injection. On day −1, mice were randomized based on total body bioluminescence. On day 0, CD19 CAR T cells produced from an HLA-A2− donor with various gene editing modifications (TRAC KO alone or with KO of one of β2m, NLRC5 or RFX5) were intravenously injected at 3×10⁶ CAR' cells. Total T cell numbers were kept constant across all groups by normalizing with non-transduced T cells. Growth of Raji tumor was tracked by total body bioluminescence at indicated time points. To track CAR T cell persistence in vivo, 40 µL of peripheral blood was obtained by cheek-bleeding on day 2, 9, and 16 post CAR T dosing. After red blood cell lysis, samples were stained with anti-human CD45, HLA-A2, and anti-idiotypic antibodies to identify CD19 CAR T cells. Counting beads (123 count eBeads, Thermo Fisher) were used to normalize CAR T cell counts. N=8 mice per group.

Figure 22B:
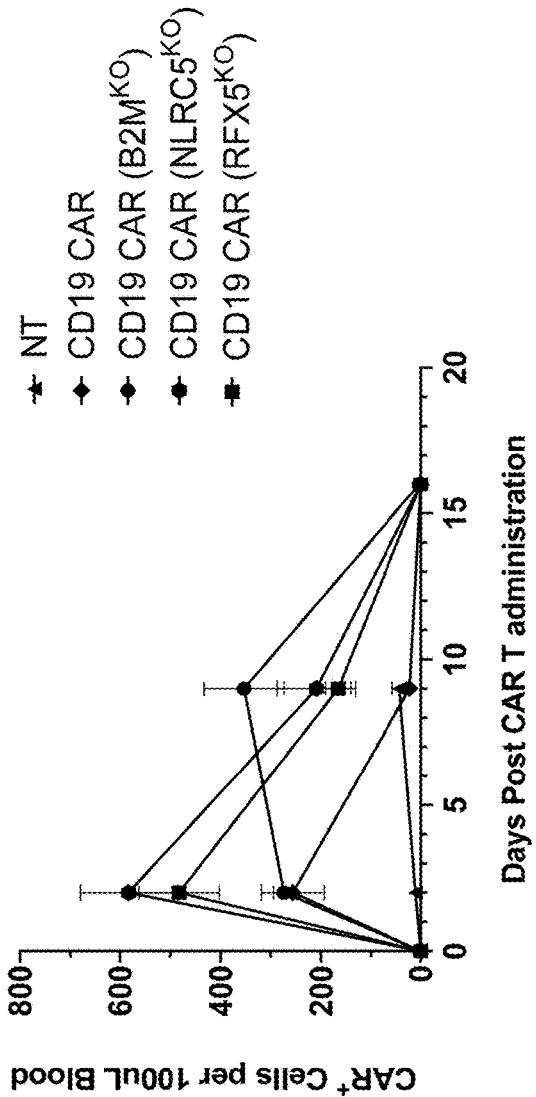
Figure 22C:
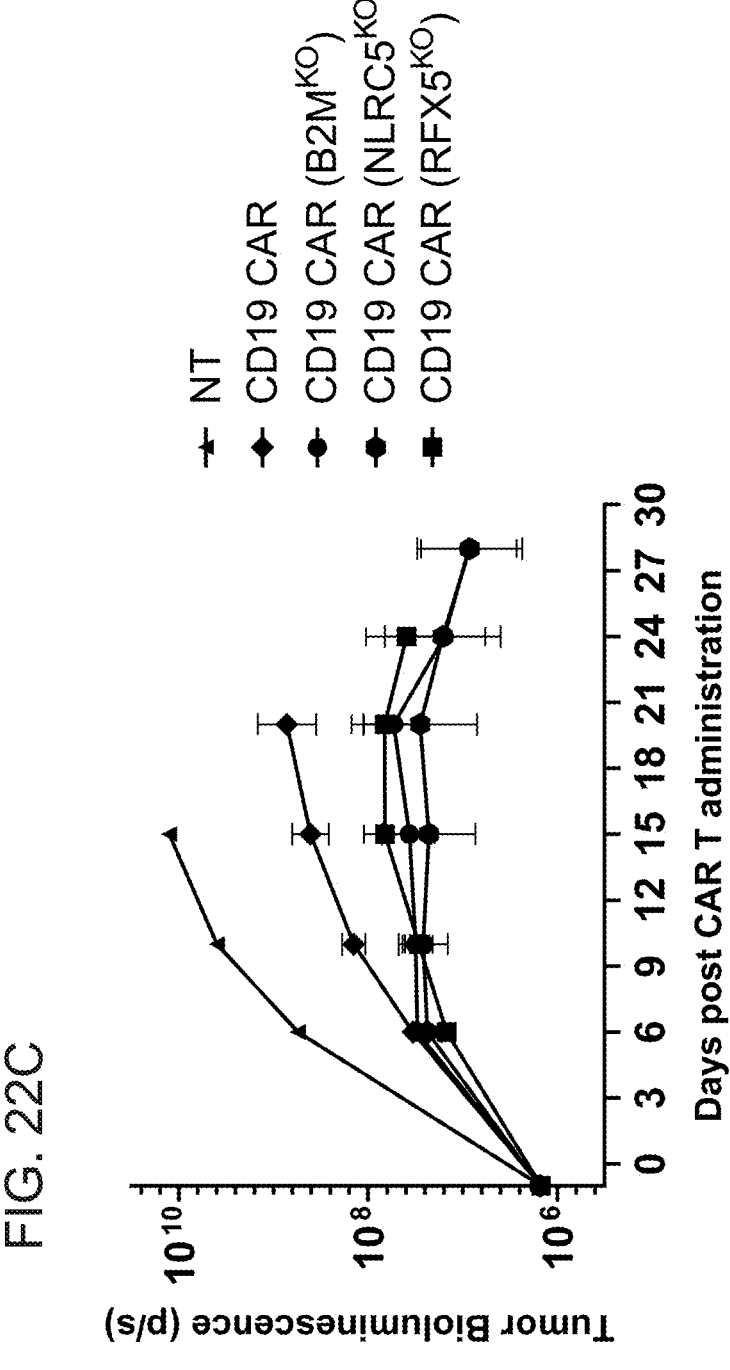

CD19 CAR T cells with gene modifications to reduce MHC-I expression (B2m, NLRC5, or RFX5 KO) showed higher CAR T cell counts and lasted longer in the peripheral blood, compared to control CD19 CAR T cells (TRAC KO alone), suggesting CAR T cells with reduced MHC-I expression were superior in mitigating allogeneic T cell rejection (FIG. 22B). Consistent with superior CAR T cell persistence, B2M KO, NLRC5 KO, and RFX5 KO CD19 CAR T cells also demonstrated better anti-tumor efficacy compared to control CD19 CAR T cells (FIG. 22C).

Example 12 NK Rejection in a Syngeneic Mouse Model

Production of gene-edited mouse T cells: Spleens of C57BL/6 mice with CD45.2 alleles were harvested, and single cell suspension was obtained by gentleMAC Dissociator (Miltenyi). Mouse T cells were then purified with the mouse T cell isolation kit II and subsequently activated by mouse T cell activation/expansion kit, following manufacturer's protocols (Miltenyi). One day post activation, mouse T cells were gene edited with CRISPR/Cas9 via electroporation (Nucleofector 4D, Lonza) similarly as human T cells. The sgRNA sequence used are from 5' to 3': ugaguauacuugaauuugag (B2m, SEQ ID NO: 20) and gccucacaagccaggcccac (Nlrc5, SEQ ID NO: 21). Gene-edited mouse T cells were expanded in vitro for 6 days in the presence of IL-2 (40 ng/ml) and IL-7 (40 ng/ml) before animal dosing.

Adoptive transfer of graft T cells: 8-12 week old C57BL/6 mice with CD45.1 or CD45.2 alleles were obtained from Jackson Laboratories (Bar Harbor, ME). C59BL/6 mice with CD45.1 alleles were irradiated at 2.5 Gy on day −3, and received 1×10⁷ control (non-gene-edited) or gene-edited (B2m or Nlrc5 KO) in vitro expanded T cells from C57BL/6 mice with CD45.2 alleles via intravenous injection on day 0. See FIG. 23A. Some C57BL/6 mice with CD45.1 alleles also received NK depleting antibody (anti-NK1.1 antibody, BioXcell) on days −3 and 0 via intraperitoneal injection, at 200 ug/mouse for each injection, and were indicated as "+NK depletion" cohort. Cell counts of host immune cells and graft T cells in the peripheral blood were tracked by flow cytometry. 40 µL of peripheral blood was obtained by cheek bleeding on indicated time points post graft T cell dosing. After red blood cell lysis, samples were stained with anti-mouse antibodies for CD45.1, CD45.2, CD3, CD4, CD8, CD19, CD335, CD11b, and H2-K$^b$ to identify graft T cells and host immune cell subsets. Counting beads (123 count eBeads, Thermo Fisher) were used to normalize cell counts. N=5 mice per group. Mean±SEM shown.

Figure 23B:
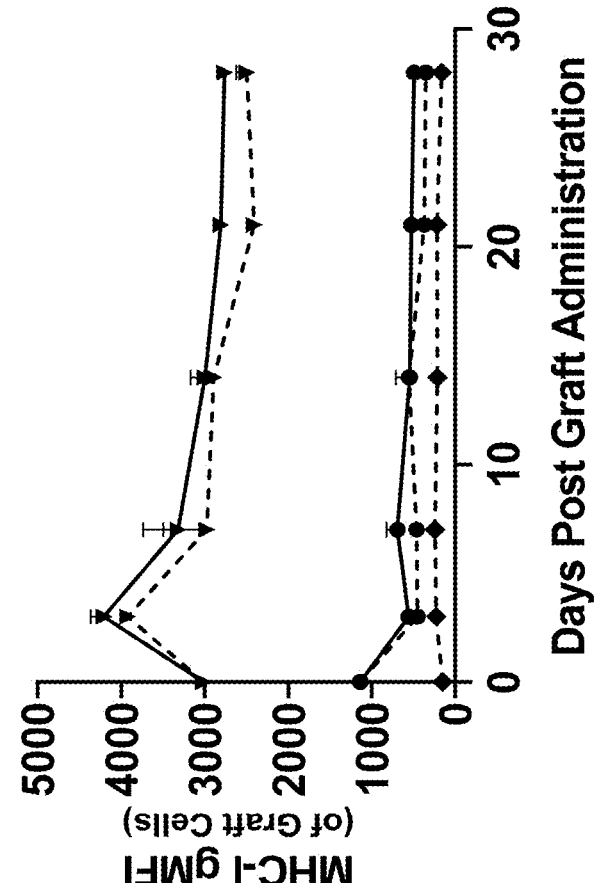
Figure 23C:
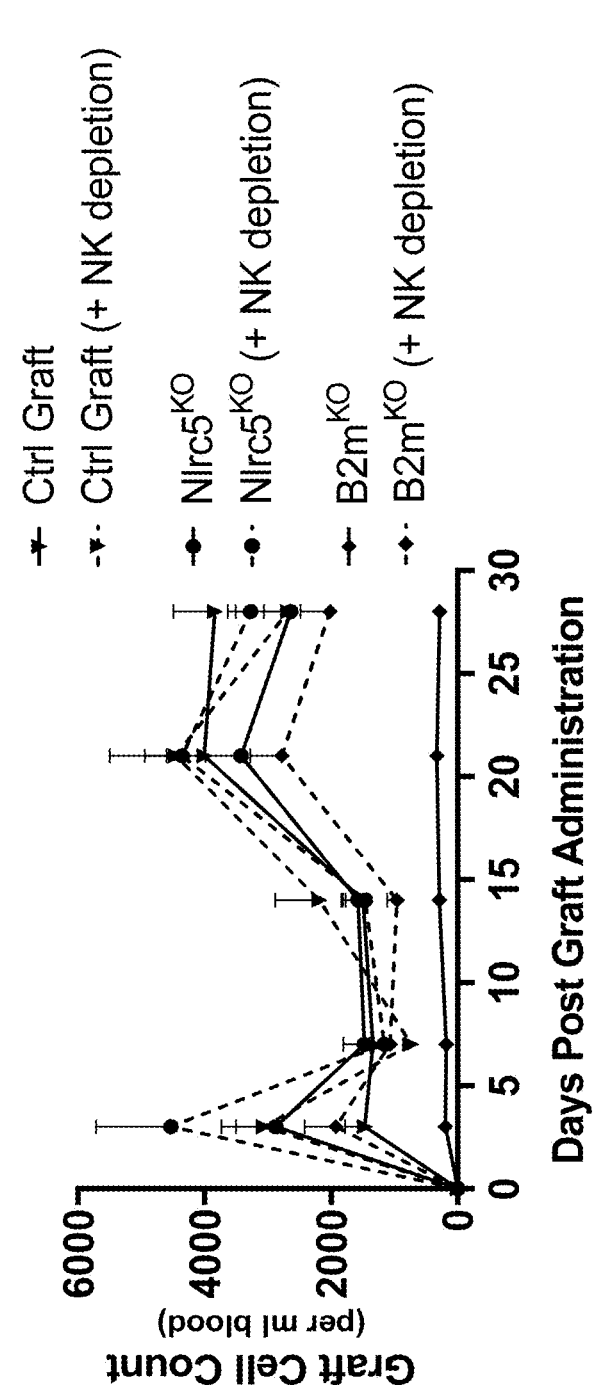

Sublethal irradiation was used to temporarily reduce host immune cells of C57BL/6 mice before graft dosing. Some mice also received NK depleting antibody to deeply deplete residual NK cells. Gene-edited (B2m or NLRC5 KO) or un-edited control graft T cells from syngeneic mice was then adoptively transferred to the host. Engraftment of the adoptive transferred T cells was tracked at various time points by flow cytometry. Grafted T cells with either B2m or Nlrc5 KO exhibited lower MHC-1 expression as determined using the anti-mouse H2-K$^b$ (BioLegend, cat. #116508) (FIG. 23B). Survival of graft T cells with NLRC5 KO was comparable to the control graft, with or without NK depletion, suggesting that knocking out Nlrc5 did not incur NK cell rejection in mice (FIG. 23C). On the contrary, B2m KO graft cells did not survive unless host NK cells were depleted, suggesting knocking out B2m rendered graft T cells sensitive to NK rejection (FIG. 23C).

All references cited herein, including patents, patent applications, papers, text books, and the like, and the references cited therein, to the extent that they are not already, are hereby incorporated by reference in their entirety.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

What is claimed is:

1. An engineered immune cell made by a method comprising altering an RFX5 gene with a CRISPR/Cas system having an sgRNA comprising SEQ ID NO: 4 so that the RFX5 gene is functionally expressed at a reduced level, wherein the cell exhibits a reduced level of expression of an MHC class I protein or complex and an MHC class II protein or complex at the cell surface.

2. The engineered immune cell of claim 1, wherein TRAC and optionally NLRC5 are functionally expressed at a reduced level.

3. The engineered immune cell of claim 1, which is further engineered so that one or more of a NLRC5, a TAP2, a B2m, a TRAC, a RFXAP, a CIITA and a RFXANK gene is functionally expressed at a reduced level.

4. The engineered immune cell of claim 1, wherein the cell is a T cell.

5. The engineered immune cell of claim 1, wherein the cell further expresses an antigen binding protein.

6. The engineered immune cell of claim 5, wherein the antigen binding protein is a chimeric antigen receptor (CAR) or a T cell receptor (TCR).

7. The engineered immune cell of claim 5, wherein the engineered immune cell comprises a nucleic acid encoding the antigen binding protein.

8. The engineered immune cell of claim 7, wherein the nucleic acid encoding the antigen binding protein is located within a disrupted locus selected from the group consisting of a RFX5, a NLRC5, a TAP2, a B2m, a TRAC, a RFXAP, a CIITA and a RFXANK locus.

9. The engineered immune cell of claim 1, wherein the engineered immune cell further comprises one or more genomic modifications of one or more of an endogenous TCRa gene and an endogenous CD52 gene.

10. The engineered immune cell of claim 1, wherein the engineered immune cell is, or is derived from, an immune cell obtained from a healthy volunteer or a patient, or is derived from an iPSC.

11. The engineered immune cell of claim 1, wherein the engineered immune cell functionally expresses one or both of a TAP2 gene and a NLRC5 gene at a reduced level.

12. The engineered immune cell of claim 11, wherein the engineered immune cell expresses one or both of the TAP2 gene and the NLRC5 gene at a level not greater than 90%, not greater than 75%, not greater than 50%, not greater than 25%, or not greater than 10% compared to expression in a non-engineered immune cell.

13. The engineered immune cell of claim 11, wherein the engineered immune cell is a T cell.

14. The engineered immune cell of claim 11, wherein the engineered immune cell further expresses an antigen binding protein.

15. The engineered immune cell of claim 14, wherein the antigen binding protein is a chimeric antigen receptor (CAR) or a T cell receptor (TCR).

16. The engineered immune cell of claim 14, wherein the engineered immune cell comprises a nucleic acid encoding the antigen binding protein.

17. The engineered immune cell of claim 16, wherein the nucleic acid encoding the antigen binding protein is located within a disrupted locus, or a locus selected from the group consisting of a TAP2, a NLRC5, a CIITA, a RFX5, a RFXANK and a RFXAP locus.

18. The engineered immune cell of claim 11, wherein the engineered immune cell further comprises one or more genomic modifications of one or more of an endogenous TCRa gene and an endogenous CD52 gene.

19. The engineered immune cell of claim 11, wherein the engineered immune cell is, or is derived from, an immune cell obtained from a healthy volunteer or a patient, or is derived from an iPSC.

20. A method of making the engineered immune cell of claim 11 comprising the use of a gene editing technology selected from the group consisting of TALENs, zinc fingers, Cas-CLOVER, and a CRISPR/Cas system to reduce the functional expression of one or both of the TAP2 and the NLRC5 genes in an immune cell, thereby producing the engineered immune cell.

21. The engineered immune cell of claim 11, wherein functional expression of the TAP2 gene and/or the NLRC5 gene is measured by determining HLA, B2m, or both HLA and B2m protein expression on the surface of the engineered immune cell, or wherein functional expression of the TAP2 gene and/or the NLRC5 gene is measured by detecting TAP2 protein and/or NLRC5 protein expression using flow cytometry.

22. The engineered immune cell of claim 1, wherein: (a) the engineered immune cell is further engineered to express one or more proteins selected from the group consisting of HLA-E, HLA-E single-chain trimer, HLA-G, HLA-G single-chain trimer, UL18, UL18 single-chain trimer, HLA-A2, HLA-A2 single-chain trimer, and human cytomegalovirus (HCMV) US11, and/or (b) the engineered immune cell is further engineered to not express, or to express at a reduced level, any one or more of a NLRC5, a TAP2, a B2m, a TRAC, a CIITA, a RFXANK, and a RFXAP gene.

23. A population of a plurality of the engineered immune cell of claim 1, wherein no more than 75% of the engineered immune cells functionally express RFX5 and wherein the engineered immune cells exhibit a reduced level of surface expression of an MHC class I protein or complex and an MHC class II protein or complex.

24. The population of engineered immune cells of claim 23, wherein at least 10%, at least 20%, at least 30%, at least 40%, at least 50%, at least 75%, or at least 90% of the engineered immune cells further express an antigen binding protein.

25. The population of engineered immune cells of claim 24, wherein the antigen binding protein is a chimeric antigen receptor (CAR) or a T cell receptor (TCR).

26. The population of engineered immune cells of claim 25, wherein a nucleic acid encoding the CAR or the TCR is inserted into a disrupted locus selected from the group consisting of a TAP2, a NLRC5, a CIITA, a RFX5, a RFXANK and a RFXAP locus.

27. The population of engineered immune cells of claim 23, wherein at least 10%, at least 20%, at least 30%, at least 40%, at least 50%, at least 75%, or at least 90% of the engineered immune cells further comprises one or more genomic modifications of one or more of an endogenous TCRa gene and an endogenous CD52 gene.

28. The population of engineered immune cells of claim 23, wherein functional expression of the RFX5 gene is measured by HLA, B2m, or both HLA and B2m protein expression on the surface of the engineered immune cell, or wherein functional expression of the RFX5 gene is measured by detecting RFX5 protein expression using flow cytometry.

29. A pharmaceutical composition comprising the engineered immune cell of claim 1, and further comprising at least one pharmaceutically acceptable carrier or excipient.

30. The pharmaceutical composition of claim 29, wherein the engineered immune cell further expresses one or more proteins selected from the group consisting of HLA-E, HLA-E single-chain trimer, HLA-G, HLA-G single-chain trimer, UL18, UL18 single-chain trimer, HLA-A2, HLA-A2 single-chain trimer, and human cytomegalovirus (HCMV) US11.

31. A method of treating a condition in a patient comprising administering to the patient the engineered immune cell of claim 1.

32. The method of claim 31, wherein the condition is a solid tumor or a liquid tumor.

33. The engineered immune cell of claim 1, wherein the engineered immune cell is engineered so that the RFX5 gene and a NLRC5 gene are functionally expressed at a reduced level.

34. The engineered immune cell of claim 1, wherein the engineered immune cell is engineered so that the RFX5 gene and a TRAC gene are functionally expressed at a reduced level.

35. The engineered immune cell of claim 1, wherein the engineered immune cell is engineered so that the RFX5 gene and a TAP2 gene are functionally expressed at a reduced level.

36. The engineered immune cell of claim 1, wherein the engineered immune cell is engineered so that the RFX5 gene and a B2m gene are functionally expressed at a reduced level.

37. The engineered immune cell of claim 1, wherein the engineered immune cell is engineered so that the RFX5 gene and a RFXAP gene are functionally expressed at a reduced level.

38. The engineered immune cell of claim 1, wherein the engineered immune cell is engineered so that the RFX5 gene and a CIITA gene are functionally expressed at a reduced level.

39. The engineered immune cell of claim 1, wherein the engineered immune cell is engineered so that the RFX5 gene and a RFXANK gene are functionally expressed at a reduced level.

* * * * *